(12) United States Patent
Beinat et al.

(10) Patent No.: US 7,337,121 B1
(45) Date of Patent: Feb. 26, 2008

(54) CLAIM ASSESSMENT MODEL

(75) Inventors: Paul Beinat, Sydney (AU); Barry Hornery, Sydney (AU); Graham Bartholomew, Sydney (AU); Nic Townsend, Sydney (AU)

(73) Assignee: ISO Claims Services, Inc., Wilmington, DE (US)

( * ) Notice: Subject to any disclaimer, the term of this patent is extended or adjusted under 35 U.S.C. 154(b) by 0 days.

(21) Appl. No.: 09/539,218

(22) Filed: Mar. 30, 2000

Related U.S. Application Data

(60) Provisional application No. 60/171,224, filed on Dec. 16, 1999, provisional application No. 60/137,037, filed on Jun. 1, 1999, provisional application No. 60/126,975, filed on Mar. 30, 1999.

(51) Int. Cl.
*G06Q 10/00* (2006.01)
(52) U.S. Cl. ............................................. 705/3
(58) Field of Classification Search ................ 705/2–4, 705/35; 128/920
See application file for complete search history.

(56) References Cited

U.S. PATENT DOCUMENTS

| | | | | |
|---|---|---|---|---|
| 4,839,822 A | * | 6/1989 | Dormond et al. ............. 706/45 |
| 4,975,840 A | * | 12/1990 | DeTore et al. ................ 705/4 |
| 5,441,047 A | * | 8/1995 | David et al. ................ 600/483 |
| 5,613,072 A | * | 3/1997 | Hammond et al. ............ 705/4 |
| 5,845,254 A | * | 12/1998 | Lockwood et al. ............ 705/2 |
| 6,032,678 A | * | 3/2000 | Rottem ....................... 600/437 |
| 6,126,690 A | * | 10/2000 | Ateshian et al. ........... 623/22.4 |
| 6,223,164 B1 | * | 4/2001 | Seare et al. ................... 705/2 |
| 6,283,761 B1 | * | 9/2001 | Joao ........................... 434/236 |
| 6,484,144 B2 | * | 11/2002 | Martin et al. ................. 705/2 |
| 6,604,080 B1 | * | 8/2003 | Kern ............................. 705/4 |

OTHER PUBLICATIONS

The Continuum Company, Inc., *Colossus: A Knowledge-Based System for Evaluating Personal Injury Claims* (1995).
Computer Sciences Corporation, *Colossus: Personal Injury Claims Staff Given a Permanent 'Second Opinion'* (Feb. 2001).

* cited by examiner

*Primary Examiner*—Andrew Joseph Rudy
*Assistant Examiner*—Vanel Frenel
(74) *Attorney, Agent, or Firm*—Walter G. Hanchuk; Chadbourne & Parke LLP

(57) ABSTRACT

A method for modeling medical conditions in a person includes providing a plurality of profiles relating predetermined medical conditions to human body parts. Each profile describes an estimated capacity of at least one body part, due to at least one condition, over time. One or more of the medical conditions are identified that affect the person. A profile corresponding to each medical condition is selected, and the selected profile's time dimension is related to the occurrence of the medical condition.

83 Claims, 22 Drawing Sheets

Internal Classes

1. Body Part
2. - Composite Body Part
3. - sight
4. - hearing
5. - soft Tissue Spine
6. - Whole Body Dysfunction
7. - Whole Body Trauma
8. Case Occupation
9. Case Activity
10. - DOT Case Activity
11. - DOT Case Occupation
12. Case Task
13. Conjunction
14. - Sided Conjunction
15. ICD9 Effects
16. ICD9 Profile
17. Prognosis
18. - Permanent Condition
19. - Occupation Incapacity
20. - Activity Incapacity
21. - Progress
22. - Psyche
23. - Temp. Codes

FIG. 2A

External Classes

17. Action Plan
18. Actual Return to Work Occupation
19. Actual Return to Work Task
20. Activity Capacity
21. Additional Jobs
22. Case Activity
23. Case Details
24. Case Task
25. CLA Criteria
26. CLA Plan
27. Claimant Occupation
28. Client
29. Client Address
30. Client Address Relation
31. DOT Codes
32. DOT Return To Work Plan
33. Future Economic
34. Future Treatment/Complication
35. Insured Template
36. Job
37. Job Activities
38. Job Tasks
39. Medical Codes
40. Medical Details
41. Medical Code Body Parts
42. Medical Code Profiles
43. Medical Symptoms
44. Permanent condition
45. Preamble
46. Prognosis Details
47. Recovery Progress
48. Return To Work Plan Criteria
49. Salary

COMPOSITE BODY PARTS

| | | | |
|---|---|---|---|
| thoracic | l ankle foot | face | cervical spine |
| lumbar | l leg | trunk | digestive |
| lumbosacral | sacral area | lower trunk | hematopoietic |
| thoracolumbar | r hand | upper trunk | reproductive |
| spine | l hand | station gait | respiratory |
| r foot | r wrist hand | use uppers | smell |
| r fore foot | l wrist hand | communication | speech |
| r ankle foot | r arm | infirmity | taste |
| r leg | l arm | head | whole body dysfunction |
| l foot | r eye | brain | whole body trauma |
| l fore foot | l eye | cardiovascular | |

HEARING
hearing

SIGHT
sight

SOFT TISSUE SPINE
cervical
thoracic
lumbosacral
sacral

ICD9 Code:         805.4.4
Instance:          L4 Vertebra
Class:             Body Part
Intermediate Code: tfrac (a bony injury)
Profile:

| Day | Dysfunction Level (%) |
|-----|----------------------|
| 0   | 100 |
| 14  | 100 |
| 28  | 50  |
| 42  | 20  |
| 56  | 10  |
| 70  | 0   |

FIG. 4

| Day    | Dysfunction Level (%) |
|--------|----------------------|
| 0      | 100 |
| 16.80  | 100 |
| 33.60  | 50  |
| 50.40  | 20  |
| 67.20  | 10  |
| 84     | 0   |

FIG. 5

| Day | Dysfunction Level (%) |
|---|---|
| 0 | 100 |
| 23.52 | 100 |
| 47.04 | 50 |
| 70.56 | 20 |
| 94.08 | 10 |
| 117.60 | 0 |

FIG. 6

| Day (original) | Day (Age/Sex) | Day (Age) | Dysfunction Level (%) |
|---|---|---|---|
| 0 | 0 | 0 | 100 |
| 35 | 42 | 58.80 | 100 |
| 42 | 50.40 | 70.56 | 80 |
| 49 | 58.80 | 82.32 | 70 |
| 56 | 67.20 | 94.08 | 65 |
| 63 | 75.60 | 105.84 | 60 |
| 70 | 84.00 | 117.60 | 55 |
| 77 | 92.40 | 129.36 | 50 |
| 84 | 100.80 | 141.12 | 45 |
| 91 | 109.20 | 152.88 | 40 |
| 98 | 117.60 | 164.64 | 35 |
| 105 | 126.00 | 176.40 | 30 |
| 112 | 134.40 | 188.16 | 25 |
| 126 | 176.40 | 246.96 | 20 |
| 140 | 168.00 | 235.20 | 15 |

FIG. 7

| PROGNOSIS | PUSH/PULL ACTIVITIES | | |
|---|---|---|---|
| | UP TO 50 POUNDS MODERATE PUSHING | UP TO 100 POUNDS HEAVY PUSHING | OVER 100 POUNDS VERY HEAVY PUSHING |
| 1. CAN DO NOW | 1, 2, 2 | 1, 1, 2 | 1, 1, 1 |
| 2. CAN DO INFREQUENTLY | 2, 3, 3 | 1, 2, 3 | 1, 1, 2 |
| 3. AVOID AT PRESENT | 3, 3, 3 | 2, 3, 3 | 1, 2, 3 |
| 4. CAN ONLY EVER DO INFREQUENTLY | 4, 5, 5 | 1, 4, 5 | 1, 2, 4 |
| 5. AVOID PERMANENTLY | 5, 5, 5 | 2, 5, 5 | 1, 4, 5 |

FIG. 11

| PROGNOSIS | LIFTING ACTIVITIES | | | | |
|---|---|---|---|---|---|
| | SMALL/LIGHT SEDENTARY | UP TO 50 LIGHT | UP TO 50 MODERATE | UP TO 100 HEAVY | OVER 100 VERY HEAVY |
| 1. CAN DO NOW | 1, 2, 2, 2, 2 | 1, 1, 2, 2, 2 | 1, 1, 1, 2, 2 | 1, 1, 1, 1, 2 | 1, 1, 1, 1, 1 |
| 2. CAN DO INFREQUENTLY | 2, 3, 3, 3, 3 | 1, 2, 3, 3, 3 | 1, 1, 2, 3, 3 | 1, 1, 1, 2, 3 | 1, 1, 1, 1, 2 |
| 3. AVOID AT PRESENT | 3, 3, 3, 3, 3 | 1, 1, 3, 3, 3 | 1, 1, 3, 3, 3 | 1, 1, 2, 3, 3 | 1, 1, 1, 2, 3 |
| 4. CAN ONLY EVER DO INFREQUENTLY | 4, 5, 5, 5, 5 | 1, 4, 5, 5, 5 | 1, 1, 4, 5, 5 | 1, 1, 1, 4, 5 | 1, 1, 1, 2, 4 |
| 5. AVOID PERMANENTLY | 5, 5, 5, 5, 5 | 1, 5, 5, 5, 5 | 1, 2, 5, 5, 5 | 1, 1, 2, 5, 5 | 1, 1, 1, 4, 5 |

FIG. 12

CLAIM ASSESSMENT MODEL

This application claims the benefit of U.S. Provisional Application 60/126,975, filed Mar. 30, 1999, U.S. Provisional Application 60/137,037, filed Jun. 1, 1999, and U.S. Provisional Application 60/171,224, filed Dec. 16, 1999.

Electronic ASCII text file appendices containing data for use in an embodiment of the invention is associated herewith. These appendices contain material subject to copyright protection.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

The present invention relates to claims adjustment, worker's compensation claims and common law claims. Traditionally, an adjuster in a workers' compensation case receives a claimant's medical information from a physician, employer, hospital or other medical provider, assesses whether the claimant will be able to return to work and, if so, assesses how long the claimant will be out of work. Based on this assessment, the adjuster assesses the potential cost to the insurer and employer. A similar process occurs where the claim, or potential claim, arises outside a workers' compensation system. There, the adjuster assesses the potential liability under "common law" recovery systems. The adjuster's decisions are based on experience, available historical medical reference data and available historical liability data, as should be understood in this art.

The claimant data and medical data may include the claimant's name, age, sex, occupation, injuries, preexisting conditions, treatments, complications and prognoses. In workers' compensation cases, the adjuster considers the claimant's job requirements in light of the medical data to determine if and when the claimant will return to work. In common law cases, the adjuster considers the claimant's medical conditions in light of historical liability data to assess the common law liability for those conditions.

SUMMARY OF THE INVENTION

The present invention recognizes and addresses disadvantages of prior art methods.

Accordingly, it is an object of the present invention to provide an improved method of assessing workers' compensation insurance claims and common law claims.

This and other objects are achieved by a computerized method for assessing medical conditions affecting a person. The method includes providing a plurality of profiles relating predetermined medical conditions to human body parts. Each profile describes an estimated capacity of at least one body part, due to at least one condition, over time. One or more of the predetermined medical conditions that affect the person are identified. A profile corresponding to each identified medical condition is selected, and each selected profile's time dimension is related to the occurrence of its medical condition.

In another embodiment, a computerized method for assessing the impact of medical conditions on a person includes providing a model of the human body. The model includes body parts that, in combination with each other, form the human body. For each medical condition of a plurality of predetermined medical conditions, a severity value is provided that describes the impact of the medical condition on at least one body part. One or more of the predetermined medical conditions that affect the person are identified. The severity values for the identified medical conditions are combined to a combined severity value.

The accompanying drawings, which are incorporated in and constitute a part of this specification, illustrate one or more embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which;

FIG. 2 is an exemplary table of data classes for use in an embodiment of the present invention;

FIG. 3 is a table of exemplary instance slots for exemplary data classes for use in an embodiment of the present invention;

FIG. 4 is a table illustrating an exemplary medical condition profile for use in an embodiment of the present invention;

FIG. 5 is a table illustrating an exemplary medical condition profile for use in an embodiment of the present invention;

FIG. 6 is a table illustrating an exemplary medical condition profile for use in an embodiment of the present invention;

FIG. 7 is a table illustrating an exemplary medical condition profile for use in an embodiment of the present invention;

FIG. 11 is an exemplary prognosis table for use in an embodiment of the present invention;

FIG. 12 is an exemplary prognosis table for use in an embodiment of the present invention;

Figure 1:
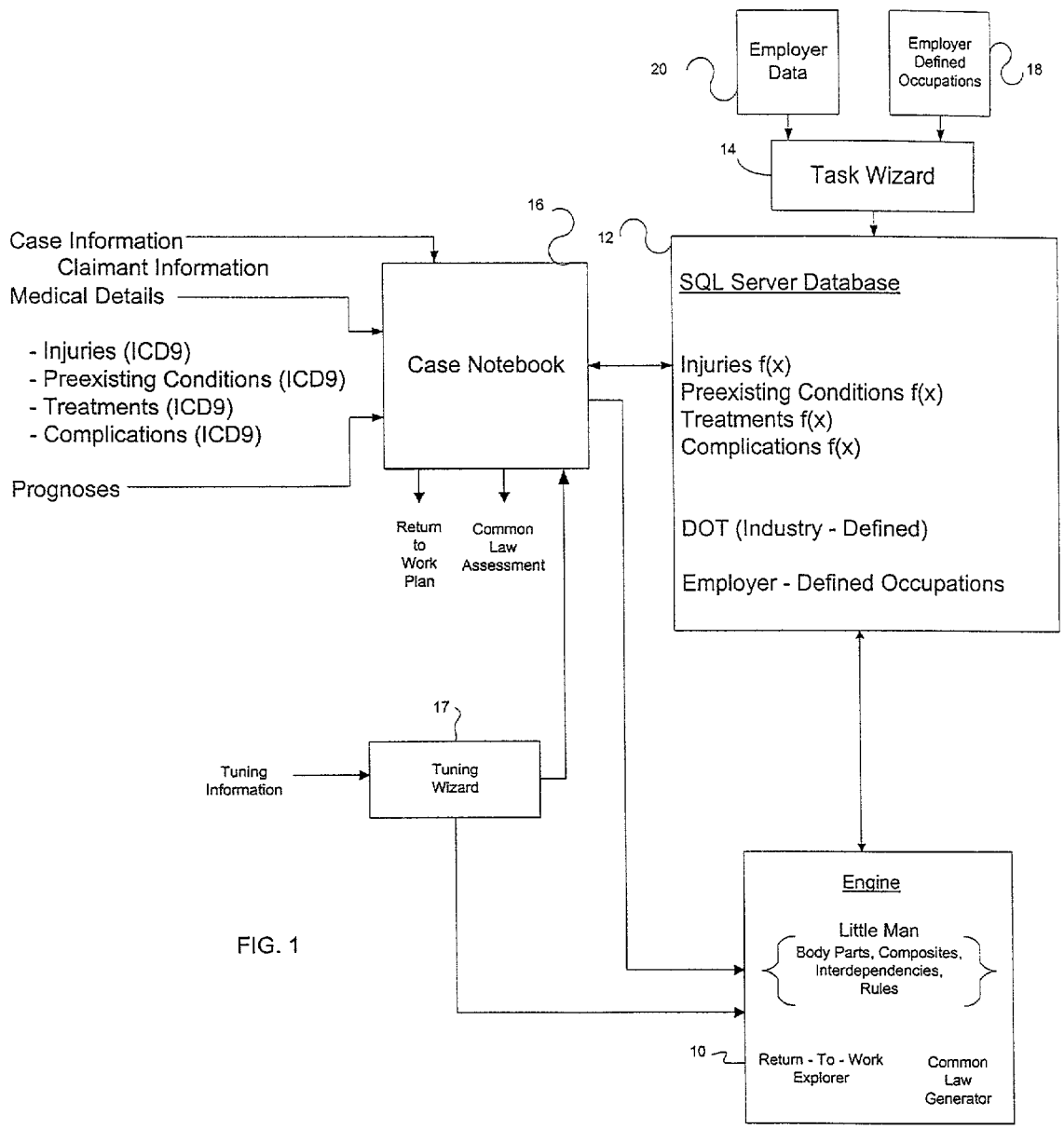
FIG. 1 is a block diagram of a claims assessment system in accordance with an embodiment of the present invention.

Repeat use of reference characters in the present specification and drawings is intended to represent same or analogous features or elements of the invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

I. The Model

The present invention relates to a model for assessing if and when an injured workers' compensation claimant can return to work and/or for assessing common law liability resulting from the claimant's injuries. As should be understood in the art of insurance adjustment, a workers' compensation claimant's cost to an insurance company and/or employer depends on the length of time the claimant is unable to perform his job. Thus, the model examines the claimant's injuries, and other medical conditions, with respect to the claimant's job requirements to model when such conditions will permit the claimant to meet the requirements. Common law liability depends on the severity of the claimant's injuries. Thus, in a common law scenario, the model examines the claimant's injuries, and other medical conditions, with respect to historical liability data to determine a common law liability assessment.

The model, illustrated in FIG. 1, is comprised of an engine 10, a database 12, and three front-end modules identified as "Task Wizard" 14, "Case Notebook" 16 and "Tuning Wizard" 17. The database (SQL Server Database) is an object orientated database that stores information regarding the effects of medical conditions such as injuries, pre-existing conditions, treatments, and complications on the parts of the human body. As is explained in more detail below, this information is stored in the form of profiles that relate each affected body part's dysfunction, due to the condition, to time. For example, assume that one of the stored injuries is a fracture to a particular vertebra. At time zero (i.e. the moment the injury occurs or is diagnosed), the dysfunction level for the vertebra is 100%. The vertebra heals over time, however, and the dysfunction level decreases accordingly. By day 28, for example, the dysfunction level may be 50%. By day 70, it may be 0%, indicating that the vertebra has entirely healed. Each day between 0 and 70 is assigned a dysfunction level value, resulting in a dysfunction level-v.-time profile for this particular injury. Since treatments and complications also affect body parts, profiles are provided for these conditions as well.

Database 12 also includes information about the claimant's job in one of two forms. The employer has the option of constructing a detailed description of all occupations at the employer's job sites. If the employer has not provided this information, however, pre-defined job templates may be provided in Task Wizard, or the engine may rely on the Dictionary of Occupational Titles (DOT), which lists occupations and general physical requirements for those occupations.

Engine 10 generally uses information provided by the SQL Database to generate return-to-work plans, common law assessments and action plans that are discussed below. To produce this information, the engine applies the profiles stored in database 12 to model the human body. This model, referred to herein as the "Little Man," is a plurality of human body parts that are described by the profiles, which may be modified according to predetermined rules. Thus, each body part is described in terms of its dysfunction level at present and into the future. The default for all body parts is a zero dysfunction level. That is, the Little Man is assumed to be entirely healthy.

Certain body parts combine to form composite body parts within the Little Man. For example, each vertebra is independently described by the dysfunction level of that vertebra. The vertebrae combine, however, to form the spine, and the model generates a profile describing the spine as a whole in terms of its dysfunction level.

The Little Man includes a set of rules that describe the interdependence among the body parts. For example, an injury to one body part may have an effect on several other body parts, even though those body parts are not injured.

To analyze a particular claimant's case, the engine retrieves data from database 12 that relates to a particular claimant's injuries or other conditions. That is, once the user has indicated through the Case Notebook the conditions that apply to the claimant, the engine retrieves the profiles that correspond to those conditions and places them into the appropriate positions in the Little Man. The engine may then determine the effects of these profiles on other body parts and composite body parts to achieve a medical description of the claimant as a whole. Since the profiles describe the claimant's condition over time, and since the engine also retrieves information about the claimant's job from the database, the engine can predict when a workers' compensation claimant should be able to return to work. Furthermore, each medical condition is associated with a severity level that can be translated into one or more common law damages categories. Thus, the model can predict common law liability when actual or potential claims fall outside a workers' compensation system.

As noted above, the user may set up employer-defined occupations through Task Wizard 14. Employer-defined occupations data 18 represents information provided by one or more employers, or by other sources, that describes occupations in terms of the tasks and activities the occupations require. For example, "bus driver" is an occupation that might include the tasks "driving," "taking tickets" and "loading luggage." The "loading luggage" task might, in turn, comprise the activities of "grasping," "reaching," and "medium lifting." Employer data 20 is specific to a given employer. It includes information identifying the employer and those occupations and tasks performed at its jobsite(s).

The user enters information about the claimant through Case Notebook 16. Injury, treatment, and complication information is entered for a particular claimant and triggers the engine to retrieve certain profiles stored in database 12. Profiles may also be provided for pre-existing conditions. In addition, a physician may enter one or more prognoses that may alter or override the return to work dates and common law severities that the engine would otherwise calculate.

A. Engine's Data Hierarchy

The engine is a computer program written in AION/DS, available from Platinum Technology. In another embodiment, it is written in C++. The front end modules are written in C++. The database management system is written in SQL SERVER. It should be understood, however, that other languages may be used. For example, the engine may be written in a suitable expert system, and any suitable database management system, such as ORACLE and DB2, may be used. Furthermore, the system may be operated on any suitable computer system, for example a personal computer having a PENTIUM II processor and 3 MB of memory.

Certain terms used herein, for example "instance," "classes" and "slots," are standard object-oriented terms. The data is organized into classes, some of which are internal (existing only in the engine) and some of which are external (either sent to or brought from the SQL database). Each class is defined by data "slots" and "methods." A data slot is simply a field into which data is input to describe a unique example of the class, referred to as an "instance." All instances in a class have the same slots but may have different data entered for those slots. The instances for the classes "composite body part", "sight," "hearing" and "soft tissue spine" are provided in FIG. 3. "Methods" are functions executed by the engine that require data from one or more slots in the instances.

Classes for one preferred embodiment are listed in FIGS. 2A and 2B. Each class includes one or more instances. For example, there are approximately 200 instances in an exemplary "body part" class. That is, the program divides the human body into approximately 200 body parts. The composite body parts and their component body parts are listed in the electronic appendices in the file Body_Part.rpt. Composites are listed in column 1. The components for each composite are listed in column 3.

As seen in FIGS. 2A and 2B, some classes are subclasses of other classes. A subclass is comprised of instances that are, in turn, comprised of one or more instances in the primary class. For example, the class "composite body part" is a subclass of the class "body part." The thoracic spine is an instance of the composite body part class and is comprised of 23 vertebrae and vertebrae joints that are, in turn, instances found in the body part class.

The object oriented database is constructed in accordance with the engine's data structure. For purposes of clarity, however, a detailed description of all the data definitions in the database and engine is not provided herein. It should be within the ability of one skilled in this art to create a suitable database and computer program in accordance with the present invention in view of the description of the present invention provided herein.

B. Setting Up a Case

Given the data structure described above, a user first inputs sufficient information into that structure through Case Notebook 16 (FIG. 1) to enable the engine to operate. The initial information identifies the case and the claimant. This includes the claimant's identity, age, gender and medical conditions, the employer's identity, the claimant's job, the tasks and activities (assuming the use of Task Wizard) for that job, whether those tasks and activities are frequently or infrequently performed, whether the tasks in each occupation are required or merely desired, whether the tasks in each occupation are useful in other occupations at the employer's jobsite(s), and the employer's insurance policy number.

Certain information may be omitted, depending on whether the case is workers' compensation or common law. For example, where there will be no common law economic loss assessment, certain employment information, for example salary, may not be needed.

The Case Notebook also receives medical details specific to the claimant. These are entered as codes (hereinafter referred to as ICD9 codes) found in revision 9 of the International Classification of Diseases—Clinical Modification. There are currently between 12,000 and 14,000 ICD9 codes. Each identifies a particular medical condition, including injuries, treatments, and complications. Complications are conditions that may arise from the first three conditions. For example, there is an ICD9 code for a fracture of the fourth lumbar vertebra. Thus, to describe a claimant's medical condition, a user simply enters all ICD9 codes that apply to that particular claimant as provided by medical reports.

As discussed in more detail below, the user, for example an adjuster, may enter prognosis information received from a physician. In general, this information can be entered at any time during the case, not only at start up. Prognosis information can indicate whether the claimant is healing slowly, quickly or is not expected to recover. It can also indicate whether the claimant has a permanent dysfunction level, is fully recovered, or can perform certain activities and tasks. This information triggers the engine to modify its previous projections.

An employer may set up one or more occupations through the Task Wizard that describe the jobs performed at its places of business, or "job sites." Employer data 20 includes the employer's identification and a list of occupations performed at each job site. Each employer may have one or more job sites. Employer data 20 points to one or more occupations that are already stored in the database from data 18 and that are performed at one or more of this particular employer's job sites.

If the user has not independently defined the employer's job sites and occupations through the Task Wizard, pre-defined DOT occupations may be identified.

As described above, job sites point to occupations; occupations point to tasks, and tasks point to activities. Activities are generic mental or physical actions, such as reasoning, sitting and bending, that might be required in performing a task. The user is free to name and define occupations and tasks as desired. In one embodiment of the present invention, however, the activities are pre-defined within the Task Wizard and the SQL database. Assuming that the user, working with the employer and risk manager, has created one or more job sites, one or more occupations falling within those job sites and one or more tasks comprising the occupations, he then identifies which of the predefined activities make up each task. In this way, all job sites, no matter how they are otherwise described by the user, are defined by the basic building blocks (i.e. the activities) with which the program is designed to function. In one preferred embodiment of the present invention, the predefined activities are:

| | | |
|---|---|---|
| sitting | kneeling | medium lifting |
| climbing ladders | squatting | light lifting |
| climbing stairs | crawling | very heavy pushing |
| bending | working heights | heavy pushing |
| running | standing | medium pushing |
| walking | very heavy lifting | twisting |
| crouching | heavy lifting | turning devices |

| | | |
|---|---|---|
| repetitive arm | driving | math |
| repetitive leg | traverse terrain | languages |
| using keyboards | grasping | reasoning |
| dexterity | | |

Similarly to the pushing and lifting activities, the math, language and reasoning activities are subdivided into categories by ability level, for example "minimal," "light," "moderate," "heavy" and "very heavy."

Four of these activities (light lifting, reaching, sight and hearing) require the use of a body part of which the human body has a pair. For example, an activity may require an arm. Because there are two arms, and only one is needed, an injury to one arm does not necessarily impair the claimant's ability to perform the activity. These activities are described herein as being "two-sided" and, as described in more detail below, are treated differently than the other activities.

Each task and each activity is identified as being either "key" or "non-key" and as being either "transferable" or "non-transferable." An occupation may have one or more key tasks and one or more transferable tasks. A task may have one or more key activities and one or more transferable activities. A key task is necessary to perform its occupation, but a non-key task is merely desirable. Thus, an injured employee may be able to return to work when able to perform all key tasks, even though he is unable to perform one or more non-key tasks. Activities are similarly described as "key" or "non-key" with respect to their tasks. Transferable tasks and activities may be applicable to occupations and tasks at the employer's jobsite(s) other than the occupations and tasks to which they are assigned through the Task Wizard. Thus, even if the model determines that an injured employee cannot return to his original occupation at a given time, an employer may be notified of any transferable tasks and activities. The employer might thereby be able to identify another job at his jobsite(s) suitable for the employee.

C. Building the Little Man

Referring to the flow charts in FIGS. 13A-13D and 16, after inputting the case information and medical details for a particular claimant, the user activates the engine through the Case Notebook (FIG. 1) at 22. Since the case information includes the employer's identity, and assuming a workers' compensation case at 31, the engine retrieves all the information in the SQL database relating to that employer at 24 (FIGS. 13A-13D). As noted above, assuming the user points to employer-defined data that was previously input through the Task Wizard at 26, this includes a description of the job sites, occupations, tasks and activities listed for that employer. The case information also indicates which occupation(s) is performed by the claimant. Where there are no Task Wizard occupations, the user may point to DOT occupations.

The engine uses the ICD9 codes entered through the Case Notebook to model the Little Man so that the Little Man describes the claimant. At 28, the engine retrieves profiles from the SQL database that correspond to the entered ICD9 codes. The codes apply to body parts, and each profile describes the level of dysfunction of a body part or composite body part over time. If there is no injury code, treatment code, complication code or prognosis for a given body part or composite body part, the profile is initially flat. That is, there is 0% dysfunction over time. If there are multiple codes, the resulting multiple profiles are combined as described below. Each ICD9 code is also associated with a severity. The use of severities is discussed in detail below with respect to common law assessments. Although there are certain exceptions, dysfunction values apply to workers' compensation, while severities apply to common law.

As an example, assume that a 62 year old female has suffered a fracture to the twenty-third vertebra (also known as the fourth lumbar vertebra). The engine first finds the profile that corresponds to the ICD9 injury code. Several ICD9 codes may share a common profile, and there are therefore many fewer profiles than codes. Thus, the SQL database may include a table in which each profile is identified by an intermediate code. In a second table, each intermediate code may be assigned to each ICD9 code to which it applies. Thus, upon finding the ICD9 code that corresponds to a fractured twenty-third vertebra), the engine finds the intermediate code associated with that ICD9 code and retrieves the dysfunction profile associated with the intermediate code.

FIG. 4 illustrates this example. The ICD9 code is 805.4.4. It applies to the L4 vertebrae, which is an instance of the class "body part." The intermediate code that identifies the profile for this ICD9 code is "tfrac." The intermediate codes are instances of a class "ICD9 Profile" in the SQL database. One of the slots in this class identifies whether the injury is a bony injury or a general injury. The significance of this distinction is described below. As indicated in parentheses in FIG. 4, "tfrac" is a bony injury.

Exemplary profiles and the ICD9 codes for which they correspond are provided in the electronic appendices in files Medical Body Parts.zip and Medical Profiles.rpt. Medical Body Parts.zip is compressed using WINZIP. The ICD9 codes are provided in column 1 of Medical Body Parts.zip. The next column identifies the body parts to which the codes apply, and column 5 lists the intermediate codes applicable to each ICD9 code. Severities are listed in column 8. The profiles are provided in Medical Profiles.rpt. Column 1 lists the intermediate codes. The values in column 2 are the profile days. The values in column 5 are the corresponding dysfunction values in percent. A fourth appendix file, Medical Attributes.zip, provides brief descriptions of the ICD9 codes at column 15.

Returning to the example, the injury profile extends from day 0, the day the injury occurs or is diagnosed, to day 70, the day at which maximum recovery is achieved. In this case, the dysfunction level for this injury on the day it occurs is 100%. It is an injury, however, from which the claimant is expected to fully recover, as indicated by the 0% dysfunction level at day 70.

At 30, the engine modifies the profiles according to predetermined rules, if applicable, that are triggered by the case information. For example, the indication that the injury is a "bony" injury triggers the application of rules based on the claimant's age and sex. Generally, bony injuries heal differently depending on the injured person's sex and age. Thus, the following rules apply:

SEX/AGE

1. If the claimant is female and between the ages of 60-69, each dysfunction profile day is multiplied by 1.2
2. If the claimant is female and between the ages of 70-79, each dysfunction profile day is multiplied by 1.3
3. If the claimant is a female beyond age 79, each dysfunction profile day is multiplied by 1.4

AGE

1. If the claimant is less than 13 years of age, each dysfunction profile day is multiplied by 0.8
2. If the claimant is between the ages of 50-59, each dysfunction profile day is multiplied by 1.2
3. If the claimant is between the ages of 60-69, each dysfunction profile day is multiplied by 1.4
4. If the claimant is between the ages of 70-79, each dysfunction profile day is multiplied by 1.6
5. If the claimant is greater than 79 years of age, each dysfunction profile day is multiplied by 1.8

The "SEX/AGE" rules apply only to bony injuries, while the "AGE" rules apply to all injuries.

If a claimant has a shoulder dislocation and is under the age of 40, the dysfunction profile is:

| Days | Dysfunction |
|------|-------------|
| 0    | 100         |
| 21   | 100         |
| 105  | 30          |
| 112  | 0           |

If, however, the claimant is 40 or older, additional treatment is assumed, and the profile becomes:

| Days | Dysfunction |
|------|-------------|
| 0    | 100         |
| 7    | 100         |
| 91   | 30          |
| 98   | 0           |

This rule applies to all shoulder dislocation codes, 831.xxx, except 831.04 and 831.14.

If a claimant has lost one tooth, the dysfunction curve is:

| Days | Dysfunction |
|------|-------------|
| 0    | 50          |
| 1    | 50          |
| 2    | 10          |
| 3    | 0           |

If the claimant loses multiple teeth, however, the dysfunction curve is determined from the following table:

| Teeth | Total Days | Min Return to Work | Max. Dys. | Residual | at Max For |
|-------|------------|--------------------|-----------|----------|------------|
| 1     | 3          | 1                  | 50        | 0        | 1          |
| 4     | 7          | 2                  | 50        | 0        | 2          |
| 8     | 14         | 4                  | 70        | 0        | 4          |
| 11    | 28         | 7                  | 75        | 5        | 4          |

Assuming the claimant has lost 11 teeth or more, the profile extends to 28 days. The maximum dysfunction, at day 0, is 75%. The residual dysfunction level, at day 28, is 5. The maximum dysfunction level, 75, extends for 4 days. The minimum return-to-work days, which is discussed below, is 4. Accordingly, the profile for 11 lost teeth

| Days | Dysfunction |
|------|-------------|
| 0    | 75          |
| 4    | 75          |
| 28   | 5           |

If a claimant loses a number of teeth between 1 and 4, 4 and 8 or 8 and 11, the corresponding values are determined by linear interpolation.

The rules above are provided for exemplary purposes only and are not intended to limit the present invention. Thus, it should be understood that rules may be used as suitable for a given environment.

Applying the sex/age rules to the FIG. 4 example, each dysfunction profile day is multiplied by 1.2, resulting in the profile shown in FIG. 5. Applying the age rule set, each dysfunction profile day is multiplied by 1.4. This further stretches the profile so that claimant is expected to reach full recovery in 117.6 days, as shown in FIG. 6. Assuming that the injury start date is June 1, the case projection date is 117.6 days after June 1, or September 27.

Assume now that this claimant has been treated by a lumbosacral fusion between the fourth and fifth lumber vertebrae. FIG. 7 illustrates the treatment's profile. The age/sex and age rules apply here as well. Thus, while the original treatment profile extends from day 0 to day 140, the claimant's age and sex stretch the profile to 235.2 days.

The day the treatment occurs (i.e. its "effective" date) is June 20. Thus, the profile extends 235.2 days beyond June 20, or February 10 of the next calendar year. Since this profile ends later than the injury profile, the case projection date is the ending date of the treatment profile, or February 10. Generally, each profile has an ending, or "residual," date, upon which maximum medical improvement occurs. The case projection date is the latest of all residual dates in a given case. Each profile also has a medical start date—the date upon which the diagnosis is given that identifies the corresponding condition. For treatments and injuries, this is typically, but not necessarily, the occurrence date. It should be understood, however, that occurrence dates can be used.

The minimum dysfunction level at the end of the profile is 15%. This indicates that there will be a permanent 15% dysfunction level to the fourth and fifth lumbar vertebrae.

II. Workers' Compensation

Figure 16:
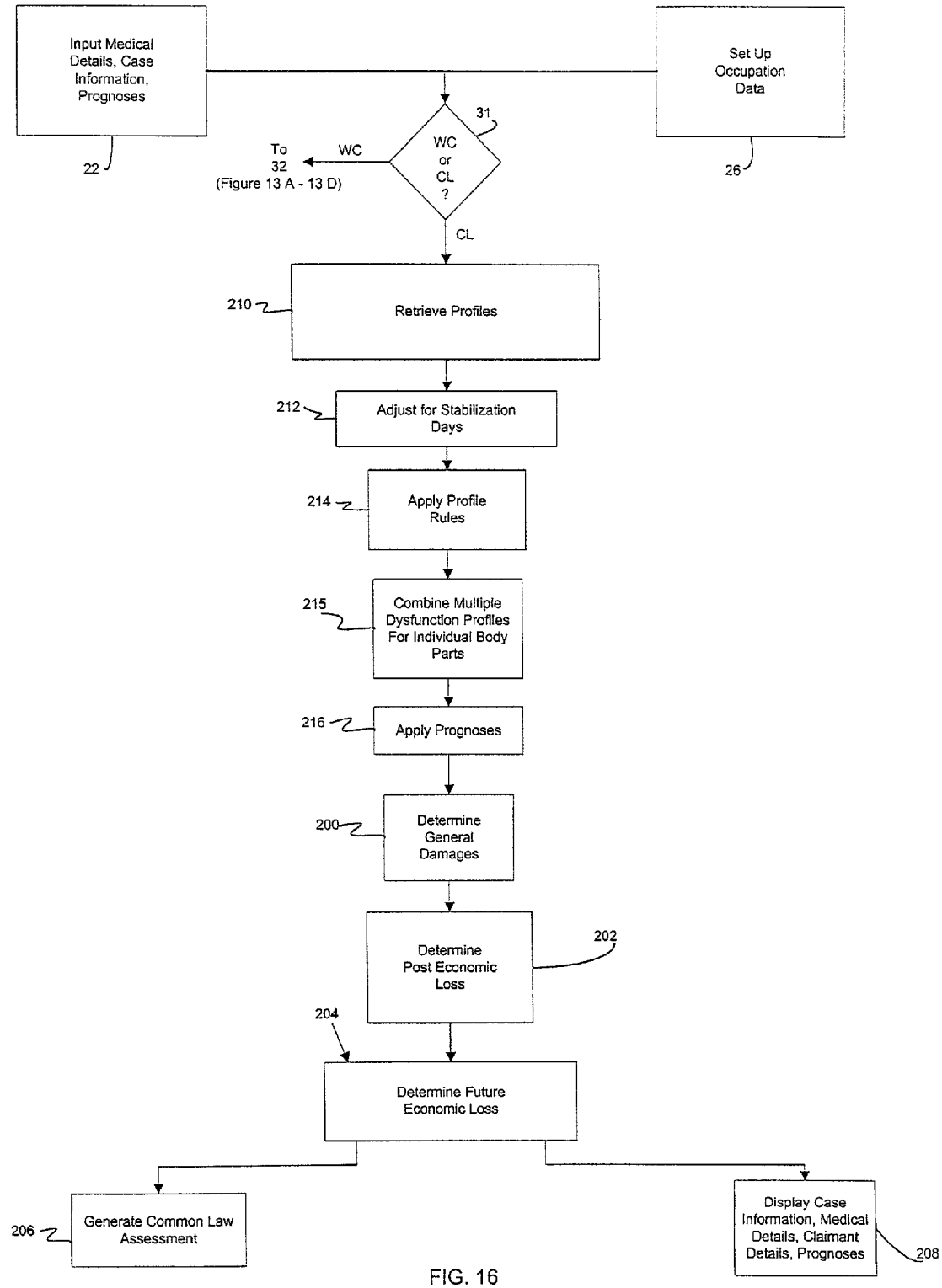
FIG. 16 is a flow chart illustrating a common law assessment method according to an embodiment of the present invention.

If the model determines that a workers' compensation assessment is needed, it executes the procedure described in FIGS. 13A-13D. FIG. 16 describes the procedure for common law assessments.

Assuming a workers' compensation case at 31 in FIGS. 13A-13D, the model has created profiles for each medical condition for each applicable body part. Before modeling for the case projection date, however, the engine allocates the effects of medical conditions on composites to their components and vice versa. For example, a diagnosis may be provided for a composite body part, such as the spine, without diagnoses specific to its components, the vertebrae. Obviously, however, an injury to the composite will most likely affect its components, and an analysis that addresses the components may take this into account. Thus, at least where it is necessary to examine the components to determine a case projection date, the engine preferably allocates a composite's medical condition profiles to its components. This is generally referred to herein as "inheritance."

Conversely, where one or more diagnoses are provided for components, but no diagnosis is provided for their composite, it is preferable to allocate the effect of the components' conditions on the composite. This is generally referred to herein as "build-up."

Figure 15A:
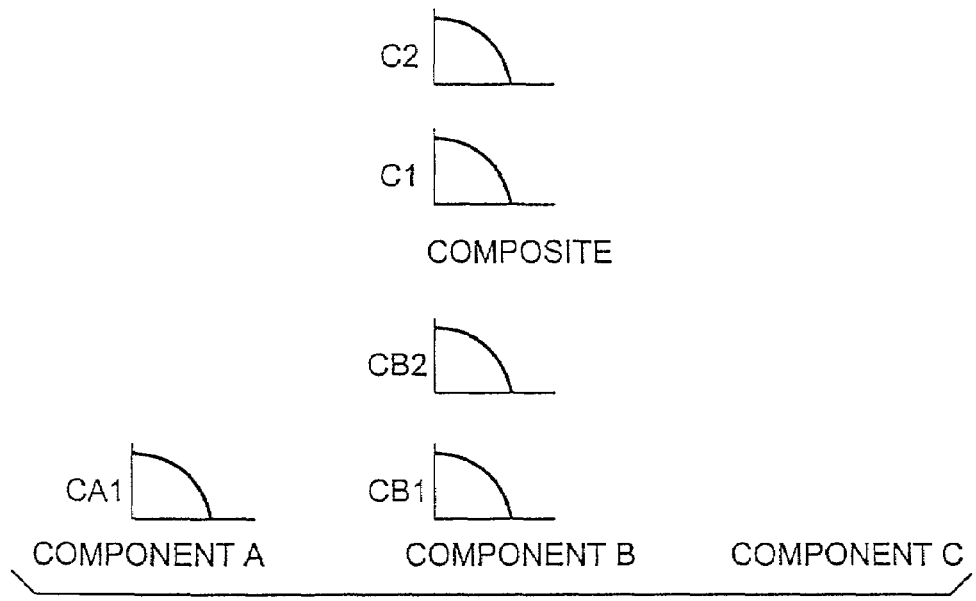
FIGS. 15A-15E is a graphical representation of inheritance and build-up routines.

FIGS. 15A-15E provide a general illustration of the inheritance and build-up procedures. Referring to FIG. 15A, assume that two diagnoses are applied to a composite body part. After adjustment for any applicable rules, therefore, the composite has two profiles, C1 and C2. The composite has three components, A, B and C. Components A and B have diagnoses that apply specifically to them, resulting in profiles CA1 for component A and CB1 and CB2 for component B.

Figure 15B:
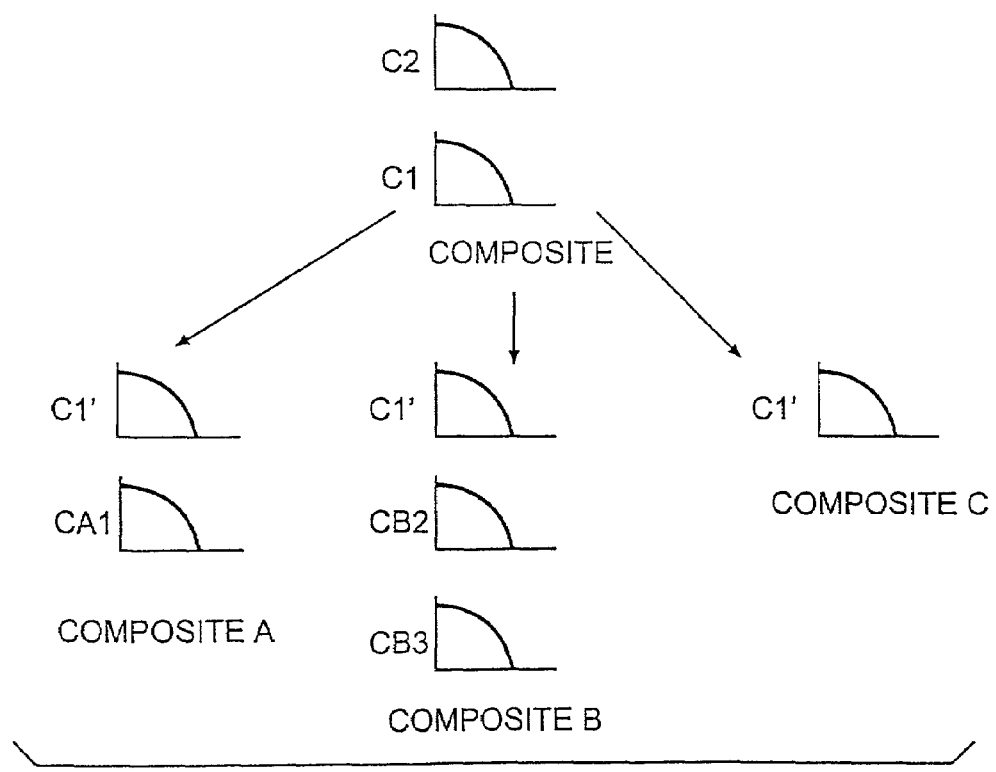
Figure 15C:
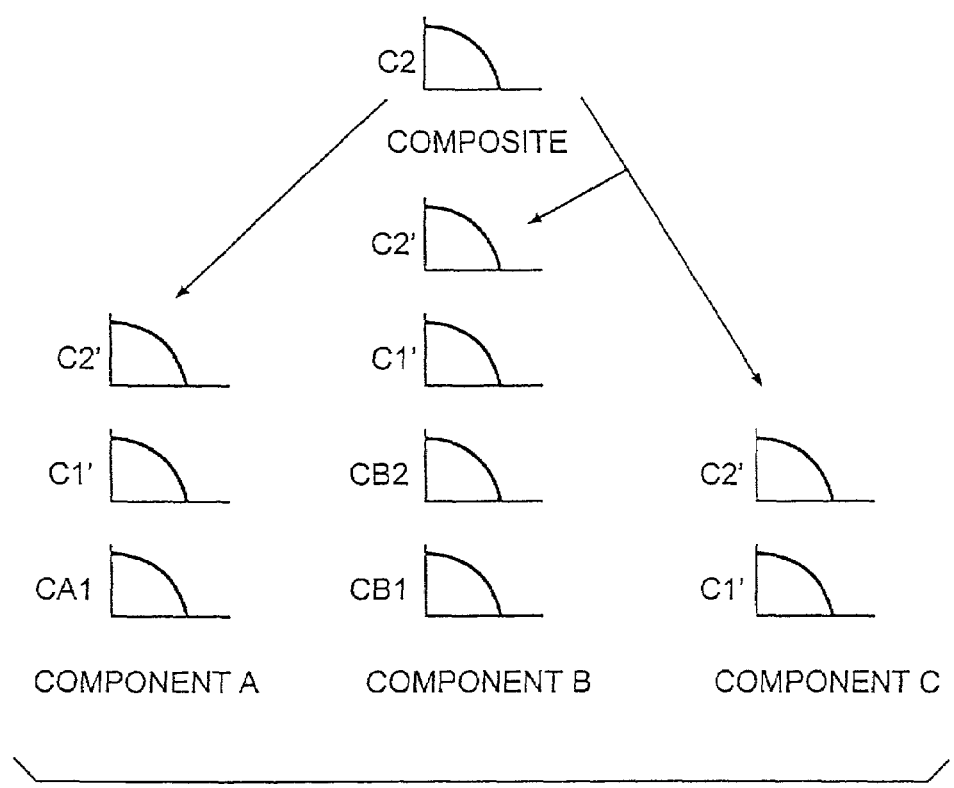

FIGS. 15B and 15C illustrate the inheritance procedure. Referring to FIG. 15B, profile C1 is allocated to a profile C1 that applies to each component. In FIG. 15C, the same procedure is applied to profile C2.

Figure 15D:
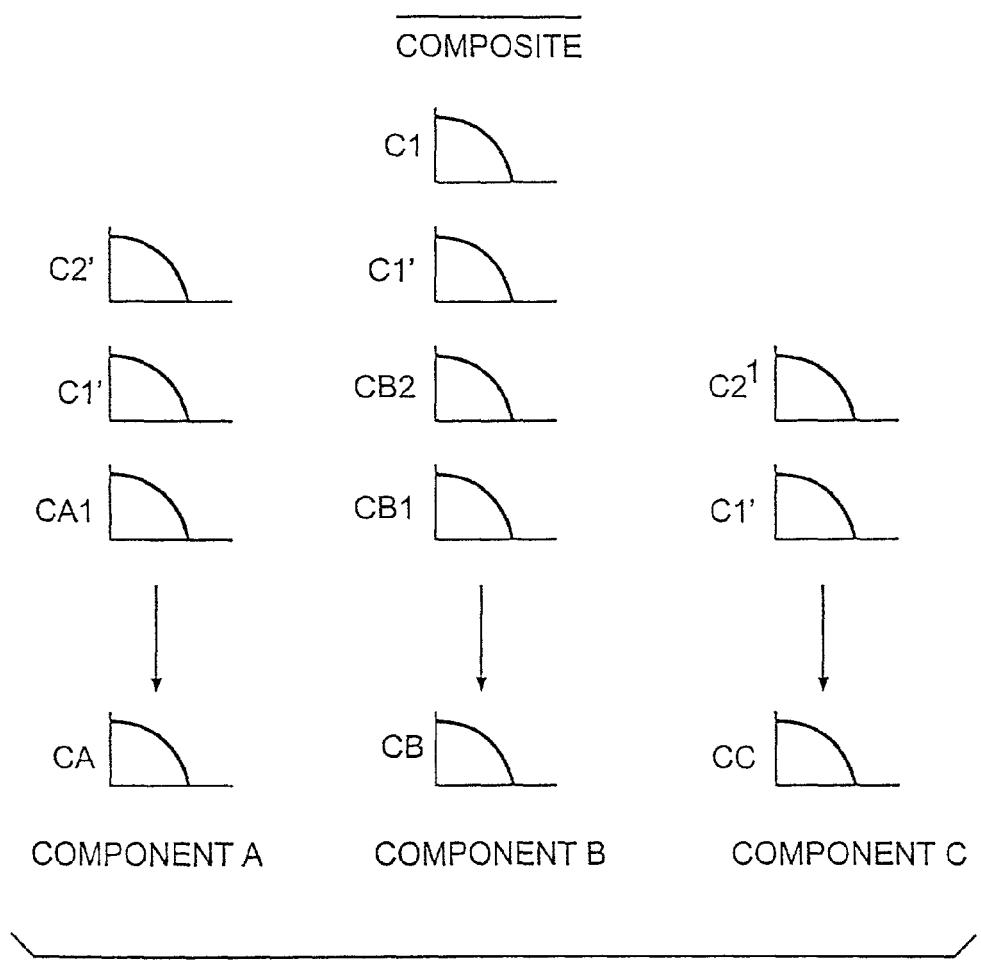
Figure 15E:
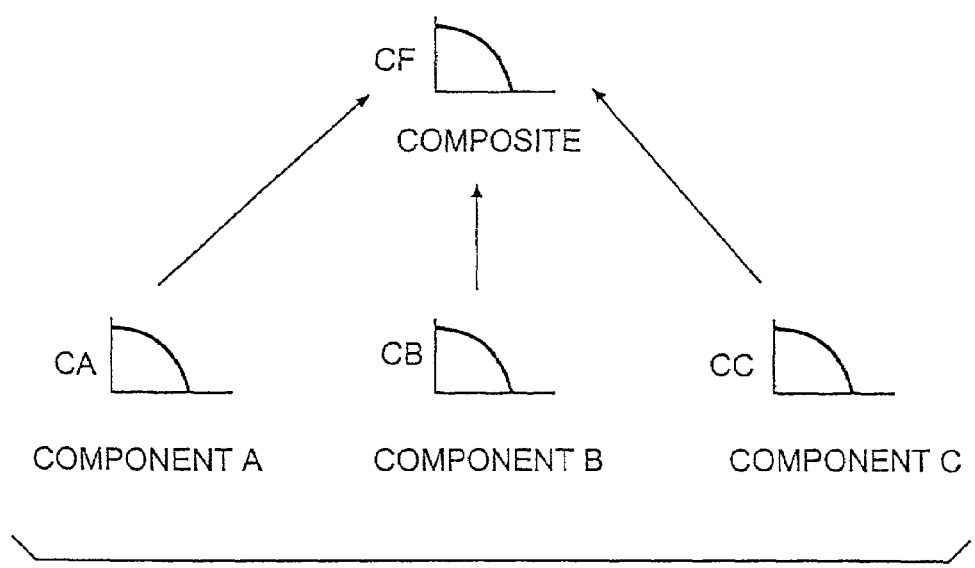

Once all the composite profiles have been allocated to the component level, as shown in FIG. 15D, the multiple profiles are combined to a single profile for each component, profiles CA, CB and CC. Finally, as shown in FIG. 15E, the final component profiles are allocated back to the composite, resulting in a final composite profile CF.

A. Inheritance

In one presently preferred embodiment, the engine may inherit a composite profile down to its components by one of two methods. Under a first option, the engine considers the effect of medical conditions in one component on neighboring components based on the components' proximity to each other. These effects are generally ignored in the second option. In the present embodiment, the interrelationships among neighboring body parts under the first option are considered only for components within the same composite body part, although it should be understood that this is but one preferred embodiment and that interrelationships may be defined among body parts from different composites and among different composites. It should also be understood that the engine may consider interrelationships other than proximity.

The choice between the options is determined at the composite body part level, specifically by activation of either of two switches in a composite body part's database record. These switches trigger rules that determine whether the first or second option will be performed with respect to a given composite.

The first switch is the "use super gravity" slot in the composite's record. If this switch is on, and if either (1) one of the composite's component body parts is injured or (2) any of the composite's component body parts is used in one of the claimant's activities, the first option is used. The second switch is the "push down past here" slot. If this switch is on and the super gravity switch is off, and if either (1) one of the composite's component body parts is injured or (2) any of the composite's component body parts are used in the claimant's activities, the second option will be performed. If both switches are on, and if either of the secondary conditions are met, the first option is used.

FIGS. 13A-13D provides a flow chart illustrating an exemplary embodiment of the inheritance routine. It should be understood that the flow chart is provided only to illustrate the model's general operation and is not intended at a literal procedural description. It should be within the skill of one of ordinary skill in this art to create a suitable program to effect the operation as described in FIGS. 13A-13D.

After constructing the profiles, the engine moves to the first composite body part at 32 and determines which option applies, according to the rules described above, at 34. The engine begins at the highest-level composite and moves down. That is, it inherits composite profiles to components only after the composite itself receives any inherited profiles from higher-level composites in the body part hierarchy.

Assuming option 1, the engine moves to the first profile for composite M at 36 and 38. Before allocating a composite's profile down to its components, the engine performs a test at 68 to determine whether the inheritance routine described at steps 42-56 below can provide a solution. The test relies on the "grouping value" for each component. The grouping value is the degree to which groups of components contribute to the functionality of the composite. That is, a composite has one or more components that are grouped into one or more component groups. Assuming that all of the composite's components have some dysfunction level, the dysfunction level for each component is multiplied by the grouping value for its group before building the component dysfunctions up to the composite level. Each component, in turn, has a "component value" that represents the degree to which the component contributes to the functionality of the group. This is a percentage that is multiplied against the component's dysfunction value before applying the grouping values. The component value and grouping value for each component and component group in one preferred embodiment are listed at columns 5 and 6 of the Body_Part.rpt file in the electronic appendices. A second copy of this file, in MS WORD 97 format, is included with the appendices at Body_Part.doc.

For example, suppose a bone in the little finger and a bone in the thumb are broken. Both the thumb and the little finger are 100% dysfunctional. Both are in the same group, but the dysfunction of the thumb may have a greater effect on the functionality of the hand than does the dysfunction of the little finger. The component and grouping values describe this relative impact in that they indicate the percentages of the dysfunction of their respective components that are to be considered in combining component profiles into a composite profile. In this case, the component value of the little finger is 10%, while the component value of the thumb is 40%. The grouping value for the group to which the little finger and thumb belong is 100%.

As a further example, assume that a composite body part includes two injured components, that each component forms its own group, that the component value for each component is 100%, that the grouping value is 50% for the first component and that the grouping value is 60% for the second component. When combining the components' profiles to determine the composite's profile, the dysfunction values in the first component's profile are scaled to 50%, and the dysfunction values in the second component's profile are scaled to 60%.

At 68, the engine retrieves the grouping value for each component in the composite and assumes that each component's grouping value is its dysfunction level for each day in its profile. The engine then builds the composite profile up from the assumed component profiles. If any of the calculated composite dysfunction values are less than the dysfunction values in the composite's original profile on their respective days, the engine will be unable to calculate component dysfunction values that would result in composite dysfunction values that approximate the original profile on those days. If this occurs, the engine assigns the composite's profile to each component and moves to the next composite at 94.

If the components pass the test at 68, the engine inherits the composite's profile down to the components. The goal is to assign a dysfunction level to each component each day in such a way that if the dysfunction levels of all the components on a given day are combined, they would result in the dysfunction level for the composite for that day in the composite's original profile. The engine performs this analysis one day at a time, or in groups of consecutive days if those days have the same dysfunction level. It starts at the first day or first group of days, goes through the routine described below until finding a suitable result for that day or group, and then moves on to the next day.

The algorithm for each day or day group is iterative. The engine makes an assumption regarding what the dysfunction level should be for each component. It then uses a build-up routine to determine, based on the assumption for the components, what the composite's dysfunction level would be for that day. The engine then compares the calculated result with the composite's actual dysfunction level on that day. If the difference between the calculated dysfunction and the dysfunction in the original profile is more than a predetermined amount, the engine adjusts the guess and repeats the process until the calculated dysfunction is within the predetermined range.

The engine starts with the composite's profile. Referring to the example above, the initial profile for the thoracic spine treatment 93.51 is:

| Days | Dysfunction Level (%) |
| --- | --- |
| 0 | 50 |
| 112 | 50 |
| 126 | 25 |
| 140 | 10 |
| 147 | 0 |

Since the claimant is between the ages of 50 and 59, the age rules discussed above multiply each day in the profile by 1.2:

| Days | Dysfunction Level (%) |
| --- | --- |
| 0 | 50 |
| 134.4 | 50 |
| 151.2 | 25 |
| 168 | 10 |
| 176.4 | 0 |

The engine may round the day values to whole numbers. Optionally, it may also interpolate the profile to provide dysfunction levels for each day. Whether or not interpolated, the profile is referred to below as the "original" profile. It is the dysfunction profile for the particular treatment identified by ICD9 code 93.51.

Since days 1 through 134 have the same dysfunction level, the engine solves for these days as a group. At 72, the first guess for the days in this group is simply the dysfunction level in the original profile for days 1 through 134 divided by the number of component body parts, 23. This results in a first component dysfunction level of 2.1739130434783 for all components. In another preferred embodiment, the first guess is the dysfunction level itself, in this case 50.

The engine next builds a composite profile from the component values, assuming the first guess. That is, it calculates what the composite's dysfunction level on days 1 through 134 would be if all the components had a dysfunction level equal to the first guess. Several 9 parameters are involved. The first, at 42, is the component's "absolute mass", in terms of its ability to function. Since the dysfunction level for each component is 2.174%, each functions at 97.826%, or 0.97826. The equation for a given component j having a dysfunction level greater than zero is:

$$Abs\ Mass(j) = ((100 - valuelist(j))/100)^{**}kvalue,$$

where valuelist(j) is the current dysfunction level guess for component j and where kvalue is equal to 1. If at 74 the component's dysfunction level is zero, the component is not considered, and the routine moves on to the next component. In this "inheritance" procedure, however, all components have a dysfunction level—the dysfunction guess.

At 44 the next parameter, "mass difference," measures the ratio of the dysfunction value mass of component j and of each other component. The equation for two components j and k is:

$$Mass\ Diff(j,k) = (min(valuelist(j),$$

valuelist(k))/(max(valuelist(j), valuelist(k)))$^{**}$G where G=1, valuelist(j) is the dysfunction guess for component j and valuelist(k) is the dysfunction guess for component k. This is performed for component j with each other component k in the composite. In the inheritance procedure, the dysfunction guesses are the same for all components, and the result of this equation is always 1. Thus, in the thoracic spine example, the mass difference for each of the 22 "other" components k is 1.

At 46, the engine determines the location of each component. In one embodiment, the routine considers each component's position as defined with respect to the composite. For example, the spine comprises a tandem arrangement of vertebrae, and each vertebra's location is described as its position in the line. Thus, vertebra T1 is position 8 in the spine, while vertebra T2 is position 9.

In another embodiment, the engine determines each component's location, as defined by "x," "y" and "z" position slots in the component's database record. These position numbers are based on a Cartesian space centered at an arbitrary origin, for example the beginning of the spine. The position of each body part may then be described in Cartesian coordinates with respect to this origin, based on some predefined unit system.

At 48, the "distance" between two functionality masses is the difference in their locations. The routine determines the distance between component j and each other component k according to the equation:

$$distance(j,k) = abs(location(j) - location(k))$$

For example, the distance (T1,T2) is abs(8-9)=1. In the present example, the routine determines 22 distance numbers. It should be understood that the routine could be configured to determine euclidean distance where location is defined by Cartesian coordinates.

At 50, the routine begins to determine the impact of each other component k on component j. This is inversely proportional to the distance between components j and k. The "distance effect" relates to the degree to which the distance between two components affects their impact on each other:

Distance Effect$(j,k)=(1/\text{Max}(\text{distance}(j,k)+1),2)**d$,

Where d=2. Thus, the distance effect cannot be less than 0.25. Distance Effect(T1,T2) is $(0.5)**2=0.25$.

At 52, the impact of a component k on component j is given by the following equation:

Impact$(j,k)=(1-(\text{Mass Diff}(j,k)*Abs \text{ Mass}(j)*\text{Distance Effect}(j,k)))2$ Here, using the numbers determined above, the impact of vertebra T2 on vertebra T1** is:

Impact$(T1,T2)=(1-(1*0.97826*0.25))**2=0.57068$

Since there is an impact of each component on component j, this part of the routine generates 22 impact numbers for component j—one for the impact of each of the 22 other thoracic components. At 54, the routine finds a "new mass" number for component j. This is the dysfunction level for the component j, considering the impact of the other components. The routine first sorts the impact numbers for the other components from smallest to highest and assigns each number an index k, beginning at the smallest impact number, sequentially from 1 to M, where k is an integer and where M is the number of other components. To determine "new mass" for component j, the routine executes the following function:

Loc New Mass$(j,k)$=Loc New Mass$(j,k-1)*(1-((1-\text{Impact}(j,k))/k)$ for k=1 to M, where loc new mass(j,0) is valuelist(j) and where New Mass(j)=Loc New Mass(j,M).

Once the routine determines New Mass for a component j at 54, it determines at 76 whether this is the last component in the composite. If not, the routine moves to the next component at 74 and repeats the procedure. If the final component is reached, the routine amalgamates the New Mass values for the components at 56. The amalgamate function is:

$x(n)=x(n-1)+((1-x(n-1))*Y(n))$, for n=1 to M, where M is the number of values Y being combined, where Y(1) is the first of those values and where x(0)=0. Thus, to combine the New Mass values for the thoracic's 23 components, the routine divides each New Mass value by 100 and executes the equation:

$x(n)=x(n-1)+((1-x(n-1))*New Mass(n))$, for components n=1 to 23. Thus, the combined dysfunction value for day, or day group, N is X(23).

In the present example, the amalgamated result, x(23), is the calculated dysfunction value for the composite body part for days 1 through 134 based on the first dysfunction guess. At 78, the routine compares this value with the value for days 1 through 134 in the composite's original profile. If the difference between the two numbers is within a predetermined tolerance, for example +/−0.1, the guess is assumed valid, and at 80, the routine assigns the guess as the inherited dysfunction value for each component for days 1 through 134. Assuming that the final day has not been reached at 82, the routine moves on to the next day or group of days at 72.

If the calculated value is outside the acceptable range at 78, the engine revises its guess at 84 by adding or subtracting a predefined increment to the first guess and returns to 74 to repeat the procedure with the revised guess. In one embodiment, the routine increases the initial guess by 0.1 if the calculated dysfunction value is too low and decreases the initial guess by 0.1 if it is too high. If the next calculated value is still outside the range and is between the original value and the prior calculated value, the engine revises the guess by the same increment. If the next calculated value is outside the range, and the original value is between the next calculated value and the prior calculated value, the increment is halved. For example, if the calculated value after the first guess is beyond the tolerance and is too high, the routine subtracts 0.1 from the first guess to reach the second guess. If the next calculated value is still beyond the tolerance and too high, the routine again subtracts 0.1. However, if the calculated value after the second guess is beyond the tolerance but too low, the engine adds 0.05 to the second guess to reach the third guess. This process repeats until the calculated value is within the tolerance.

In another preferred embodiment, if the first guess or any subsequent guess is too low, the new guess is determined as follows:

new guess=old guess+50(1−(old guess/100))

If the first guess or any subsequent guess is too high, the new guess is determined as follows:

new guess=2(old guess−50)

In the example above, the guess that provided a result within the tolerance was 9.59579. That number, therefore, is the dysfunction level (in %) for each component due to the 50% dysfunction level resulting from the treatment to the thoracic spine on days 1 through 134. If the routine is continued for the rest of the days so that the final day is reached at 82, each component in the thoracic spine has the following profile:

| Days | Dysfunction Level (%) |
|---|---|
| 0 | 9.6 |
| 134 | 9.6 |
| 151 | 4.31 |
| 168 | 1.65 |
| 176 | 0 |

If the build-up routine is performed for these 23 identical component profiles, the result will approximate the original dysfunction profile for the thoracic spine.

If there is another profile at 83 that is applicable to the composite, the routine returns to 38 to inherit that profile as well.

After the last profile has been allocated for composite M, the engine determines at 99 whether the last composite has been analyzed. If not, the engine returns to 34 and determines whether the first or second option applies to the next composite. If the "push down from here" slot is activated in the composite's database record, if one or more of the composite's components is used in one of the claimant's activities, and if the conditions described above are not met to apply the first option, the engine applies the second option. Moving to the composite's first profile at 94 and 95, the engine moves to the first day/day group N at 96. As with the first option, the engine assigns a dysfunction level for day/day group N for each component such that if the dysfunction level of all components on day N are combined, they approximately result in the dysfunction level for the composite for that day in the composite's original profile.

Assuming the same original profile (dysfunction level 50% at day 0 and dysfunction level 0% at day 176.4), days 1-134 have the same dysfunction level and are therefore treated as a group. At 98, the first guess for the days in this group is the dysfunction level in the original profile for days 1-134 divided by the number of component body parts, 23. This results in a first component dysfunction level 2.1739130434783 for all components. In another preferred embodiment, the first guess is the dysfunction level itself.

The engine next builds a composite profile from the component values, assuming the first guess. That is, it calculates what the composite's dysfunction level on days 1-134 would be if all the components had a dysfunction level equal to the first guess. At 199, the engine multiplies the dysfunction value over days 1-134 (the first guess) for each component by the component's grouping value. The result is referred to below as the component's "component value." At 100, the engine combines the component values for days 1-134 using the amalgamate function described above. That is, for each day, $$X(i)=X(i-1)+((1-X(i-1))*D(i)),$$

for i=1 to M, where M is the number of components, where D(i) is the dysfunction level in decimal form on that day for profile i, where X(0)=0, and where the composite's dysfunction level for that day in the new composite profile is X(M).

The amalgamated result is the calculated dysfunction value for the composite body part for days 1-134 based on the first dysfunction guess. At 101, the routine compares this value with the values for days 1-134 in the composite's original profile. If the difference between the two numbers is within a predetermined tolerance, for example +/−0.1, the guess is assumed valid, and at 102 the routine assigns the guess as the inherited dysfunction value for each component for days 1-134. Assuming that the final day has not been reached at 103, the routine moves on to the next day or group of days at 98.

If the calculated value is outside the acceptable range at 101, the engine revises its guess at 103 by adding or subtracting a predefined increment to the first guess and returns to 199 to repeat the procedure with the revised guess. In one embodiment, the routine increases the initial guess by 0.1 if the calculated dysfunction level is too low and decreases the initial guess by 0.1 if it is too high. If the next calculated value is still outside the range and is between the original value and the prior calculated value, the engine revises the guess by the same increment. If the next calculated value is outside the range, and the original value is between the next calculated value and the prior calculated value, the increment is halved. This process repeats until the calculated value is within the tolerance. In an alternate embodiment, the engine determines each new guess by the equations described above with respect to the first option's exemplary alternate embodiment.

Once the last day for the composite's original profile is completed at 103, the profile has been allocated to a component profile for each of the composite's components.

If the build-up routine is performed for these identical component profiles, the result will approximate the original function profile for the composite. If there is another profile at 104 that is applicable to the composite, the routine returns to 95 to inherit that profile as well.

When the last profile is reached at 104, the engine returns to 99 to determine whether the last composite has been analyzed. If not, the engine moves to the next composite at 34. If so, the engine has concluded the inheritance routine and moves to the build-up routine.

B. Build-Up

At this point, all composite profiles for which inheritance was activated have been allocated down to the components. Where the conditions for inheritance were not met as described above, the engine does not allocate composite profiles. The engine now, for each composite, combines the component profiles to determine a composite profile that replaces the composite's original profile(s). Moving to the first composite at 70, the engine checks at 71 to determine whether the first or second option applies to composite P.

Assuming the first option, the model determines at 73 the dysfunction levels for each day in each component profile for composite P by a straightforward interpolation. As an example, the dysfunction value for day 58.8 in the profile in FIG. 7 is 100%. The dysfunction value for the next day listed in the profile, day 70.56, is 80%. Rounding each day number to the nearest day (59 and 71, respectively), the program performs an interpolation to determine the dysfunction value for the interim days 60-70. For day 60, the dysfunction level X is defined according to the following relation:

$$(60-59)/(71-59)=(X-100)/(80-100).$$

Solving for X yields 98.33. This procedure is repeated for each interim day and each profile for each component applicable to the composite.

The engine now moves to each component for composite P and combines multiple profiles that may exist for the component. Referring again to the thoracic spine example discussed above and with respect to FIG. 14, the composite's profile 58 will have been allocated to all the components T1-T12. Furthermore, injury and treatment profiles apply to components T10, T9-10 and T10-11.

The manner in which profiles are combined depends upon the profile type. As noted above, there are three types of profiles in the present embodiment: injuries, complications and treatments. Preexisting conditions may also be considered. The profiles are identified as type A or type B. Type A profiles are combined at 88 using the build-up routine described by steps 75, 42, 44, 46, 48, 50, 52, 54, 76 and 56 above, where Q refers to the component profiles of a single component, rather than the several components. This results in a single profile that is then combined with the type B profiles at 90 by selecting the highest dysfunction level for each day among the resulting type A profile and the type B profiles.

Preferably, injury profiles are always type A, and treatment and complication profiles are always type B. In one preferred embodiment, preexisting conditions are type A. Profiles inherited from a composite retain their type from the composite.

Figure 14:
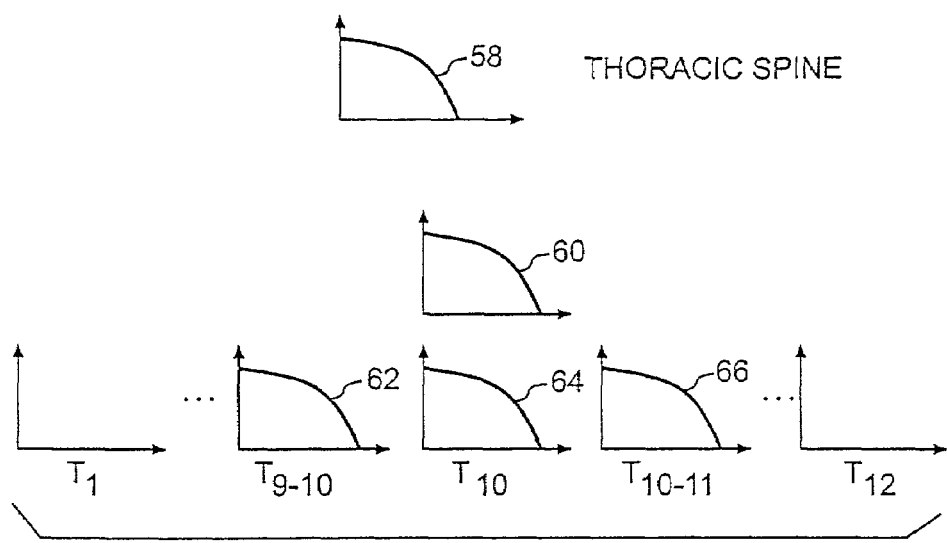
FIG. 14 is a graphical representation of medical condition profiles applicable to a composite body part and its component body parts for use in an embodiment of the present invention.

Referring to FIG. 14, assume that a 52 year old male has endured a treatment to his thoracic spine. The treatment profile is represented by a curve 58. The thoracic spine is a composite body part made up of 23 components. The components are twelve vertebrae (T1 through T12) in the spine and the 11 joints (T1-2 through T11-12) between these vertebrae. Assume also that there is an injury to one of the thoracic vertebrae (T10) and a treatment to the T10 and to joints T9-10 and T10-11. The injury profile is indicated at curve 60, and the treatment profiles are indicated at curves 62, 64 and 66.

Also, assume that the first option is chosen in that the "use super gravity" switch is turned on for the thoracic spine. Since this switch is turned on, and since one of the components is injured, the engine uses the first option. Note that if there was no injury to the T10 vertebra, the first option may still have applied if the component body parts (the vertebrae and their joints) were associated with any of the claimant's activities.

Referring to the T10 vertebra, for example, there are three curves: the inherited treatment profile, the injury profile 60 (FIG. 14) and the treatment profile 64 (FIG. 14). The build-up routine of steps 75 through 56 would be used at 88 to combine any multiple injury profiles that might exist, where Q refers to the multiple profiles. Since there is only one of these type A profiles, however, the routine combines the three profiles at 90 by choosing the highest dysfunction level among the profiles for each profile day. In this case, the component's inherited profile is treated as a type B profile since the original profile was a type B profile. If, however, the composite's original profile was, or included, a type A profile, its inherited profiles are considered to be type A profiles.

The routine will also detect the multiple curves for the T9-10 and T10-11 components at 86. Since profiles 62 and 66 are treatment profiles, they are combined with the inherited treatment profiles for their respective components at 90.

The engine repeats this procedure for each of the composite's components, and each component therefore has at most a single profile. At 92, the engine combines these profiles to determine a new profile for the composite. For each day, the engine executes the gravity routine described above with respect to steps 75 through 56. The result is the composite's new dysfunction level for that day. After repeating the procedure for all profile days, the engine has determined a new dysfunction profile for the composite that accounts for the profiles applied to its components.

The engine has now allocated the effects of the composite's profiles with those of its components using the first option. If the engine has not completed the final composite at 197, it moves to the next composite at 71 and determines whether the first or second option applies. If the first option applies, the engine executes the routine for the next composite as described above, beginning at 73. However, if the first option does not apply and the second option does apply, the engine then executes the second option, interpolating the profiles for each component of composite P at 111 so that the profiles have a dysfunction value for each integer day. The routine then moves to the first of the composite's profiles at 113 and determines at 115 whether multiple profiles exist for that component. If not, the routine moves to the next component through 117 to 115.

If a component has multiple profiles, they are combined using the amalgamate algorithm. Moving to the first profile day at 129 and 119, the combined profile value X is:

$$X(i)=X(i-1)+(1-X(i-1))*D(i),$$

For i+1 to M, where M is the number of profiles for the component, where $D(i)$ is the dysfunction level in decimal form on that day for profile i, where $X(0)=0$, and where the component's dysfunction level for that day is $X(M)$.

Once the routine determines the component's combined dysfunction level for a given day at 119, it moves to the next day N at 121 and 123 and repeats the procedure until all the days in the component's profiles have been combined. If this is not the last component at 117, the routine moves to the next component at 115.

When the routine completes the combination of the component profiles at 117, each component has a single profile, and the engine combines these profiles to provide a composite profile. First, at 125, the routine determines a final component dysfunction value for each component for each day. Similarly to the procedure described above with respect to first option inheritance, the routine multiplies the combined dysfunction value for each day for each component by the component's component value and grouping value. That is, each component's combined profile is scaled by the applicable component and grouping values. At 127, the routine determines the composite profile by amalgamating the final component dysfunction values for each day. That is, the composite's profile dysfunction value X for each day is:

$$X(i)=X(i-1)+(1-X(i-1))*D(i),$$

For i=1 to M, where M is the number of component profiles, where $D(i)$ is the dysfunction level in decimal form on that day for profile i, where $X(0)=0$, and where the composite's dysfunction level for that day in the new composite profile is $X(M)$. The routine then returns to 197 to determine whether the last composite has been analyzed. The engine first combines component profiles for those composites that do not have components that are themselves composites. It then sequentially proceeds to higher-level composites. When the routine completes this procedure for all composites for which inheritance is triggered, those composites and their components each have at most one profile.

C. Medical Prognoses

As described above, the engine relies upon predefined profiles, as modified by predefined rules that might apply. Preferably, these profiles are derived by one or more individuals experienced in the art of claims adjusting from their knowledge and experience and from historical medical reference data found in publications as should be understood by those skilled in the art of insurance adjusting.

The predefined profiles are therefore estimates based on general experience. Each individual claimant, however, may have unique healing characteristics. Thus, the engine accepts physician prognoses and expands or shrinks the dysfunction profiles based thereon. These prognoses are referred to as "medical" prognoses as opposed to "activity" and "occupation" prognoses discussed below.

Medical prognoses are divided into two groups: (1) recovery prognoses, and (2) impairment prognoses. There are 10 recovery options and 3 impairment type options. The physician may be requested to provide a prognosis in accordance with this format, or the adjuster may translate a physician's medical report.

The adjuster enters the prognoses by activating the options that apply. The recovery prognosis options are:
1. Has reached MMI—has impairment/disability—may worsen in the future.
2. Has reached MMI—has impairment/disability—should not have problems in the future.
3. Has reached MMI—has no impairment/disability-could have problems in the future.
4. Has reached MMI—has no impairment/disability—likely to have problems in the future.
5. Has reached MMI—has no impairment/disability.
6. Is healing satisfactorily.
7. Is healing slowly.
8. Will heal in weeks.
9. Will heal in months.
10. Will heal eventually.

"MMI" is an abbreviation for "maximum medical improvement."

The impairment prognosis options are: (1) AMA impairment rating, (2) disability rating, and (3) loss of function. The following discussion addresses the effect of each prognosis option.

The engine accepts only one preferred prognosis per body part. If multiple prognoses are entered for the same body part, the engine uses the one that is identified as the "preferred" prognosis.

Figure 8:
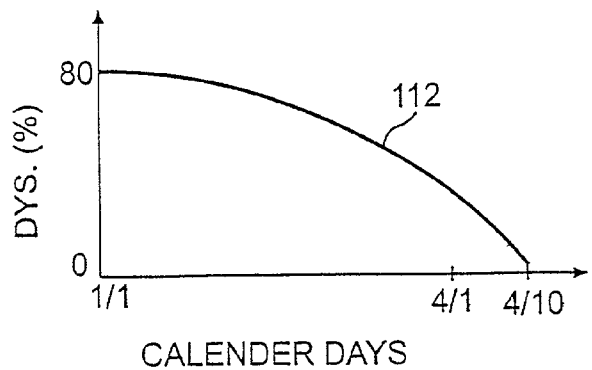
FIG. 8 is an exemplary graphical representation of a medical condition profile for use in an embodiment of the present invention.

The effect of a prognosis depends on when it is given. Referring to FIG. 8, for example, an injury profile 112 is defined for a body part over a one hundred day period. Since the injury occurred, and was diagnosed, on January 1, the projected residual date is April 10. The residual date is the day upon which maximum medical improvement (MMI) occurs. In this case, the injury completely heals. Thus, MMI is 0% dysfunction. Some profiles, however, may never reach 0%. In those cases, MMI is the final dysfunction level, and the residual date is the day that this dysfunction level is achieved.

1. Has Reached MMI—Has Impairment/Disability

The first two recovery prognoses ("has reached MMI—has impairment/disability—may worsen in the future" and "has reached MMI—has impairment/disability-should not have problems in the future") indicate that MMI has been achieved as of the effective date of the prognosis (hereinafter the "prognosis date"). Preferably, for all prognoses indicating MMI has been reached, the prognosis date is entered by the user as the day on which the physician indicated MMI was reached. Alternatively, the user may enter a number representing the number of weeks after the injury, or before the prognosis date, that MMI was reached. If no such date is provided, the prognosis date is the date the prognosis was made.

The engine compares the prognosis date to the residual date and the injury start date. If the difference between the injury start date and the residual date is greater than 21 days, and if the prognosis date is less than a date halfway between the injury start date and the residual date, the engine displays a message to the final report indicating that the body part has stabilized very quickly and requesting that the user review the medical data. Nevertheless, the engine applies the prognosis to the profile.

Each of these prognoses requires that the user enter an impairment level. If no impairment level is entered, the engine prompts the user for a residual impairment level. If an impairment is entered, the engine executes the impairment routine described below to adjust the profile. That is, the effect of these two prognoses to a return-to-work plan is, generally, the same as if the user had simply entered an impairment rating. The prognoses are retained as separate options, however, in part because a physician's report might include such statements. Also, in one embodiment, the prognosis allows the user to establish an MMI date that is different from the prognosis date, whereas an impairment date is the prognosis date.

The user has nine "literal value" options in entering an impairment value:

| Severity | Value |
|---|---|
| minor, trivial, insignificant | 5 |
| mild | 10 |
| moderate | 25 |
| significant | 30 |
| considerable | 40 |
| moderately severe | 50 |
| severe | 70 |
| gross | 80 |
| profound, total | 100 |

However, the user also has the option to directly input a numeric value. The numeric value can be any impairment value, not just those listed in the second column above.

The engine then converts the impairment rating to a dysfunction level. "Impairment" refers to damage to the body part. "Dysfunction" refers to the inability of the body part to function as a result of the damage. As noted above, the user must identify the impairment rating as an "AMA impairment rating," a "disability rating" or a "loss of function rating," each of which should be understood by those skilled in this art. Disability ratings and loss of function ratings actually refer to dysfunction levels rather than impairment levels. Thus, if an impairment rating is identified under either of these categories, no conversion is performed, and the engine treats the entered impairment rating as a dysfunction level.

On the other hand, an AMA impairment rating reflects an impairment value and must be converted. The relationship between impairment level and dysfunction level varies from body part to body part. Thus, for each body part and composite body part, a "maximum dysfunction value" and a "maximum impairment value" are defined. The maximum dysfunction value is the maximum dysfunction level, typically 100%, that the program will recognize for that body part. The maximum impairment value is the impairment level that results in the maximum dysfunction level. For example, a 70% impairment of a knee results in 100% dysfunction. The knee can certainly be impaired to a greater degree, but this will not result in additional dysfunction since the maximum is already achieved.

The engine uses the ratio of the maximum dysfunction value to the maximum impairment value to convert the entered impairment value to a dysfunction level. For example, assume that the user inputs a 60% impairment level for the right knee under one of the two prognoses discussed above. Since the maximum dysfunction value is 100%, and the maximum impairment value is 70%, the ratio of these two values is 1.439. Applying this ratio to the entered impairment value of 60%, the dysfunction value is 85.74%.

If the AMA impairment rating is assigned to any part of the spine, however, the engine compares the entered impairment value against the Maximum Impairment Value for that body part and uses the lower of the two. If the entered value is greater than the maximum value, the program so notifies the user.

Once the dysfunction level is obtained from the entered impairment value, the engine adjusts the profile for the applicable body part or composite body part. As noted above, the adjustment depends on the relation between the residual date and the prognosis date or a specified MMI date.

Figure 9:
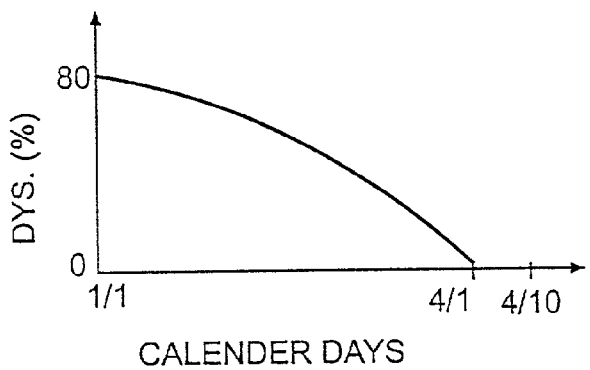
FIG. 9 is a graphical illustration of an exemplary modification to the profile in FIG. 8 according to a recovery prognosis.

If the impairment date (the prognosis date if the impairment is entered as part of a prognosis), is prior to the residual date, the profile is compressed to move the residual date to the impairment date. For example, referring to the one hundred day curve shown in FIG. 8, the residual date is April 10. Assume that an impairment is entered having an effective date of April 1. Assuming that the impairment period is the impairment date (April 1) minus the injury start date (January 1) plus 1, and that the residual period is the residual date (April 10) minus the injury start date (January 1) plus 1, the compression factor is equal to the impairment period divided by the residual period, in this case 0.91. Thus, the X-axis position of each point on profile 112 is multiplied by 0.91 so that the profile is compressed to the profile shown in FIG. 9. As an example, assume that in the original profile shown in FIG. 8, the dysfunction level at day 25 was 97.83. From the compression, the 97.83 dysfunction level is moved to day 22.75 (25*0.91). Rounding to the nearest day, day 23 in the profile curve shown in FIG. 9 has a dysfunction level of 97.83%.

Figure 10:
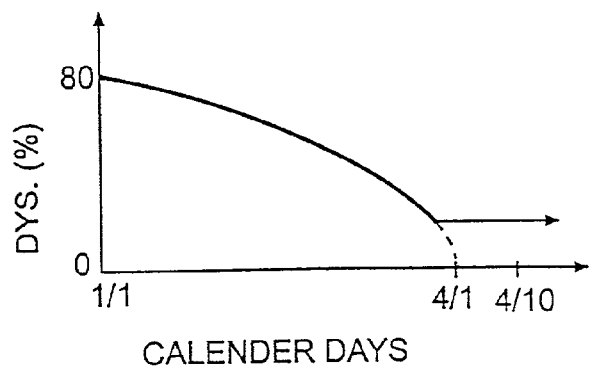
FIG. 10 is a graphical illustration of an exemplary modification to the profile in FIG. 8 according to a recovery prognosis.
Figure 13:
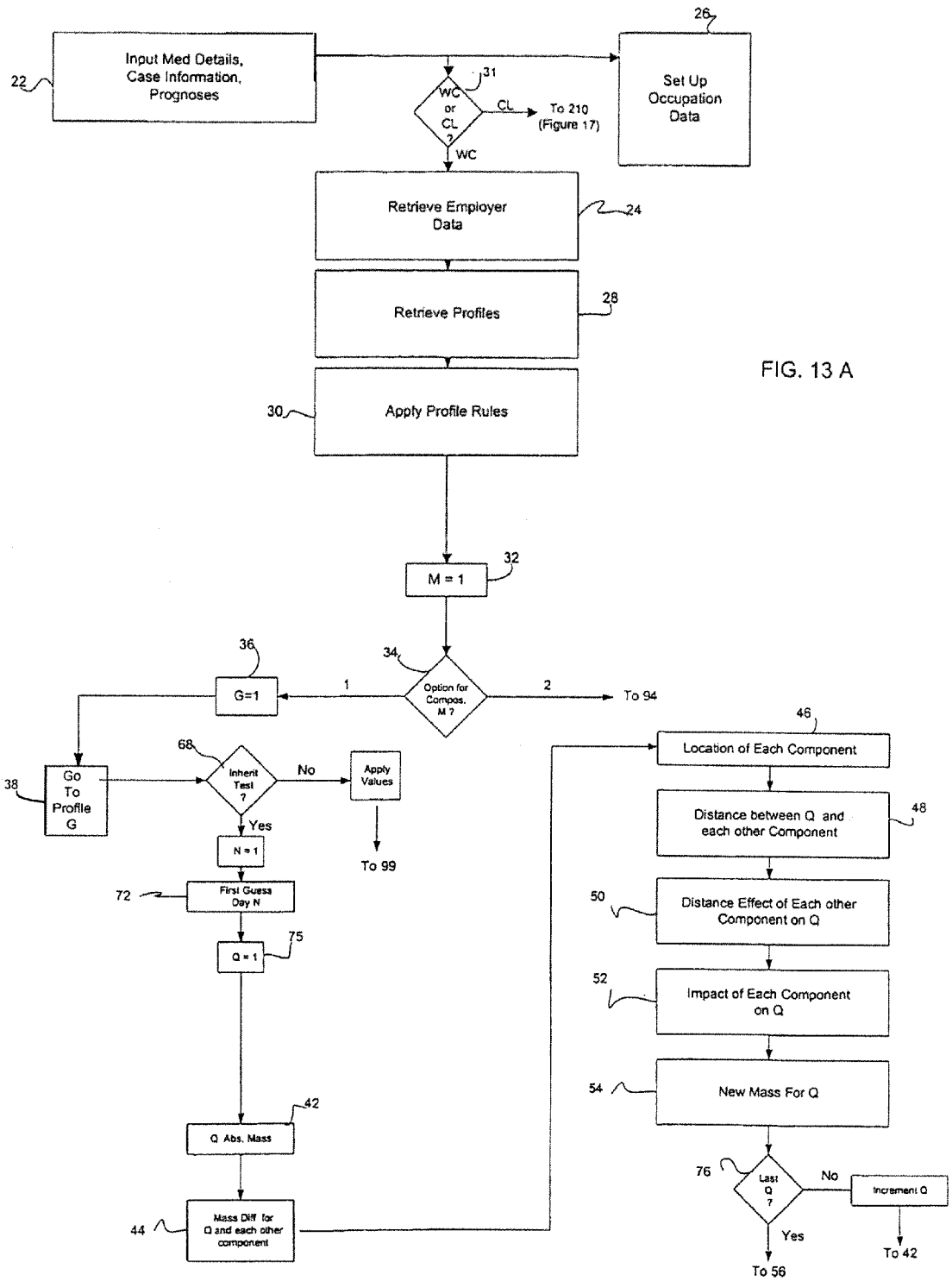
FIGS. 13A-13D is a flow chart illustrating a workers' compensation assessment method according to an embodiment of the present invention.
Figure 13:
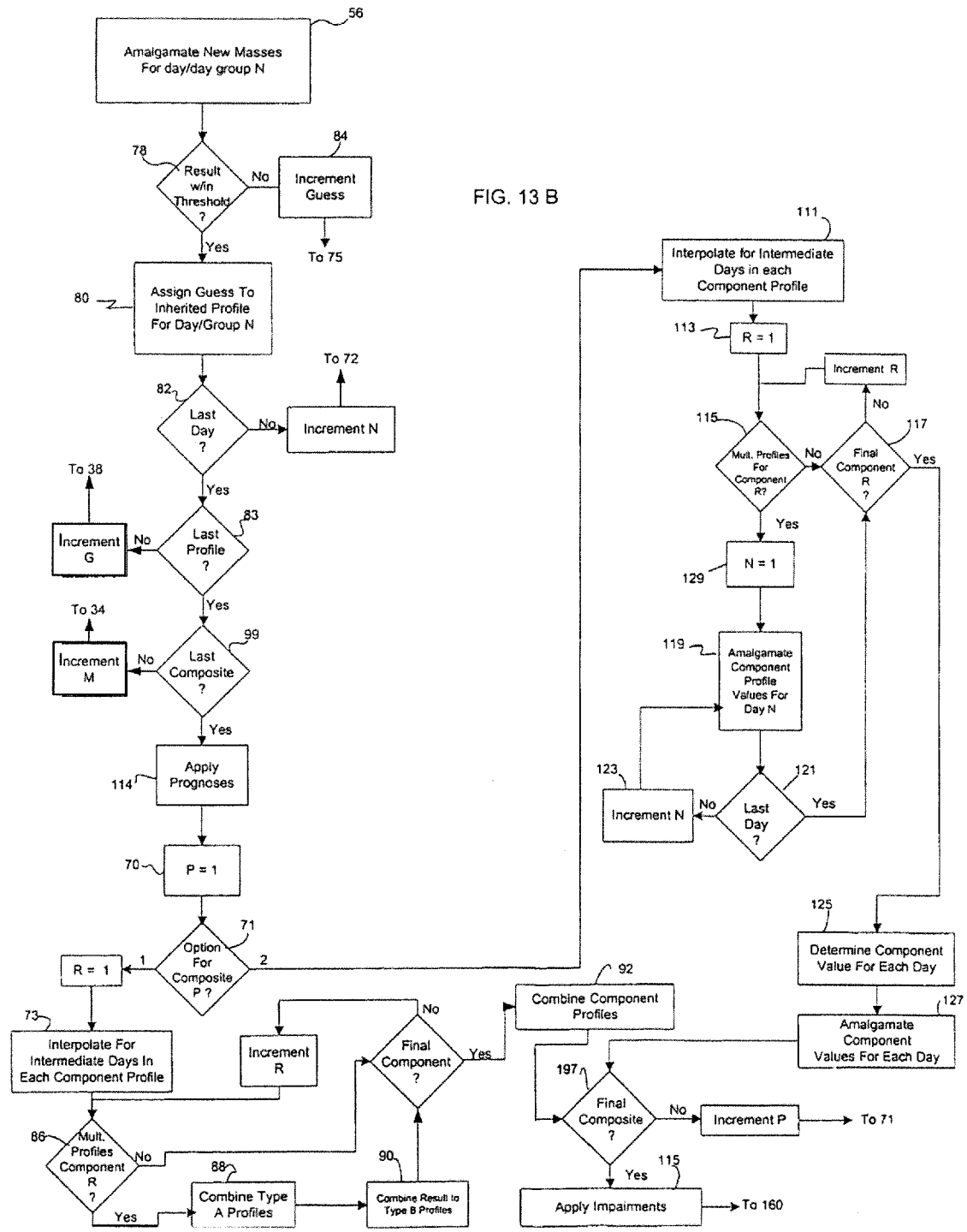
Figure 13:
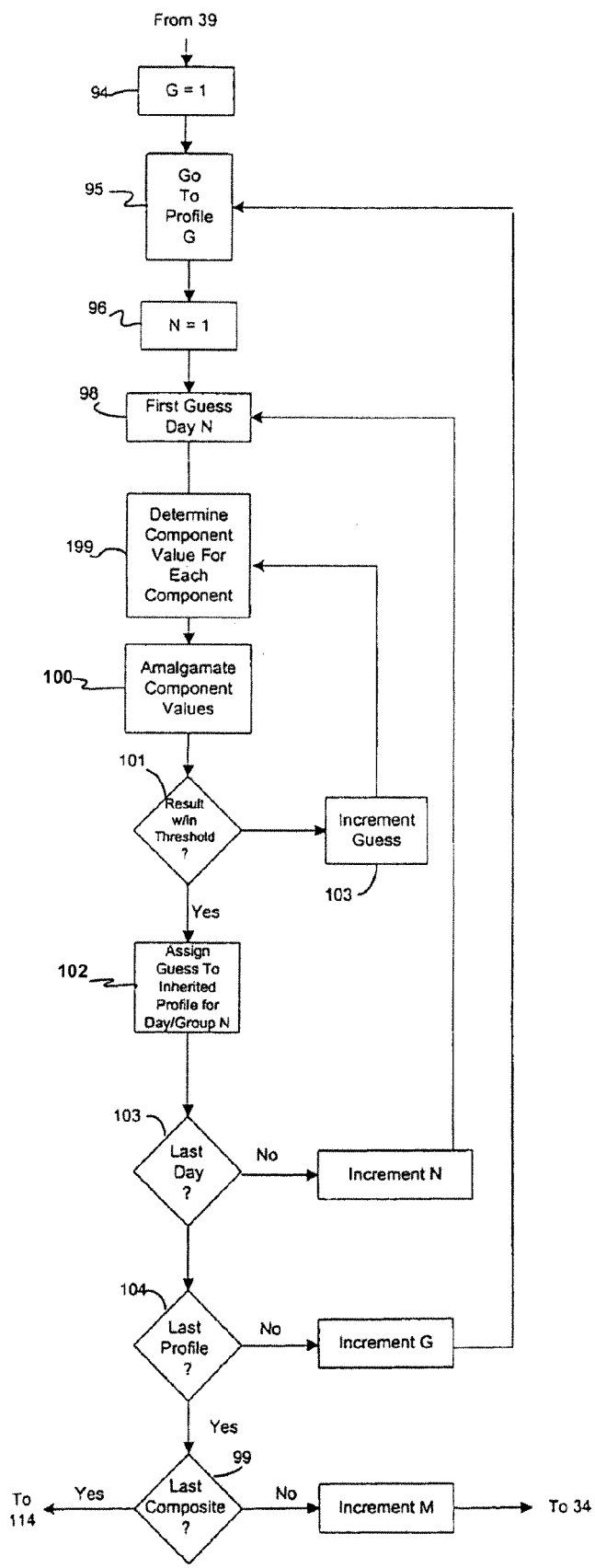
Figure 13:
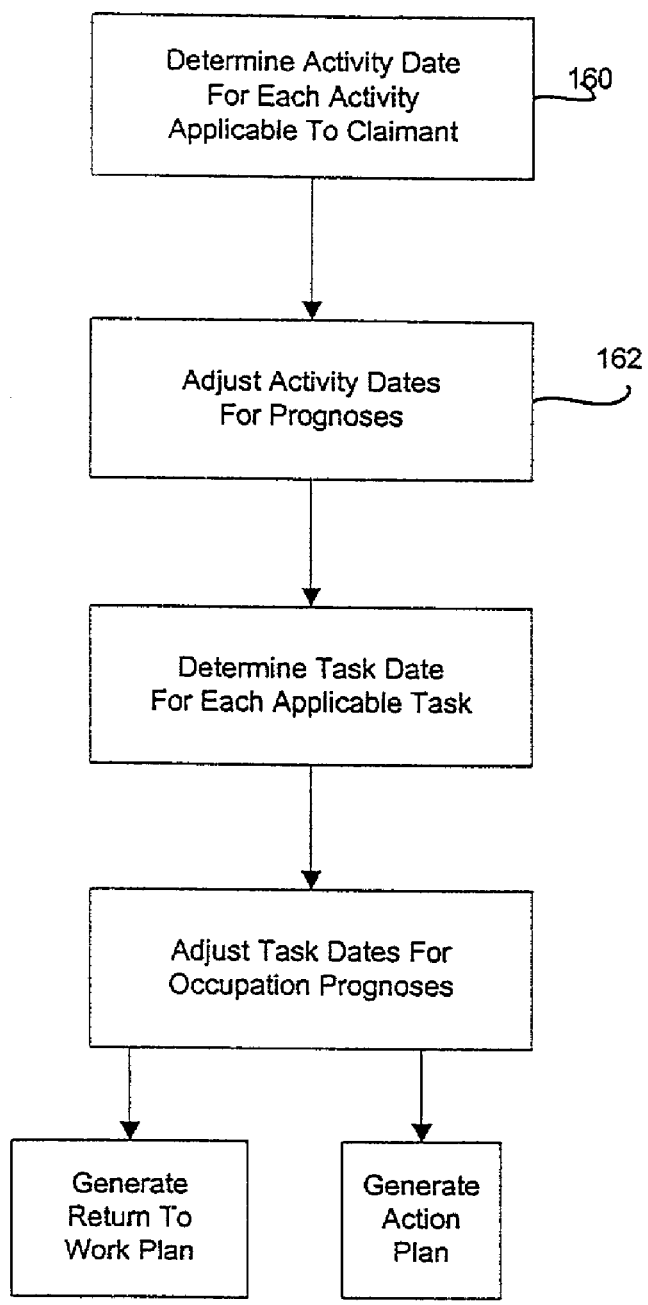

Referring now to FIG. 10, assume that the impairment level entered for this body part on April 1 corresponds to a 15% dysfunction level. The engine applies the 15% level at April 1 and every day thereafter. Since the profile went to 0 at the residual date, the engine applies the 15% level to every day prior to the residual date until reaching the first date upon which the dysfunction level is 15% or higher. If the dysfunction level at the residual date were greater than 15%, the profile would simply drop to 15% on that day.

2. Has Reached MMI—Has No Impairment

If one of the third, fourth and fifth prognoses ("has reached MMI—has no impairment/disability—could have problems in the future," "has reached MMI—has no impairment/disability—likely to have problems in the future" or "has reached MMI—has no impairment/disability") is entered, the user has indicated that the claimant's dysfunction level for that body part has gone to 0 as of the prognosis date or a specified MMI date. If the prognosis date is prior to the halfway date between the injury start date and the residual date, the engine displays a message to the user that the recovery is earlier than expected. The engine will, however, adjust the profile. If the prognosis date is prior to the original residual date, the profile is compressed as discussed above with respect to impairment values. If the dysfunction level on the original residual date is greater than 0 (i.e. the profile ends in a permanent dysfunction), the engine notifies the user that a prognosis has been entered indicating that complete healing has occurred for a condition expected to result in permanent dysfunction. The user is then prompted to confirm this result.

If the prognosis is added after the residual date, and the dysfunction level on the original residual date is 0, the profile is not adjusted. If the dysfunction level at the residual date was greater than 0, the dysfunction level is brought to 0 on the prognosis date, and the user is prompted to confirm the result.

3. Healing Satisfactorily

If the user enters the "healing satisfactorily" prognosis, the engine again determines a response based on the prognosis date. If this prognosis is entered relatively early in the profile, the prognosis indicates that the physician and the original profile are in agreement as of that date. However, if the prognosis date is near to or beyond the original residual date, the prognosis indicates that the patient continues to heal, and is therefore still dysfunctional, even though the original profile indicates the patient should be at or near MMI. Thus, in the latter case, the engine extends the profile.

Assume that the prognosis period is equal to the prognosis date minus the injury start date plus 1. If the prognosis period multiplied by 1.11, or the prognosis period plus 7, is less than the number of days in the original profile, the engine assumes that the prognosis date is early enough to indicate that the prognosis agrees with the profile. In this case, the profile is not adjusted.

If either of these calculations is greater than the number of days in the original profile, the prognosis date is late enough so that the profile should be extended. To extend the profile, the engine multiplies each day number by a stretch factor. The stretch factor is equal to the greater of the following two functions:

$$1.11*A/B$$

or $$(7+A)/B,$$

where A is the prognosis period, and B is the number of days in the original profile.

For example, assume that the original profile extends one hundred days, from January 1 to April 10. Assume that the "healing satisfactorily" prognosis is entered on April 20. Since the prognosis date is beyond the residual date, both 1.11*A and (7+A) are greater than the number of days in the original profile, and the engine therefore determines a stretch factor. The prognosis period is 110, and the number of days in the original profile is 100. Applying these numbers to the two functions above, the results are 1.221 and 1.17, respectively. Thus, the stretch factor is 1.221. If the dysfunction level at the original residual date (day 100, April 10) is zero, this dysfunction level is moved to day 122.1. The days are rounded to the nearest day. Thus, the new residual date is May 2. Assuming that the dysfunction level at day 25 is 97.83%, the stretch factor expands the curve so that this dysfunction level now occurs at day 31 (25*1.221=30.525).

If the prognosis period for this prognosis is equal to or greater than twice the number of days in the original profile, and the original profile was greater than 14 days, the engine notifies the user that this prognosis was added well after the body part should have stabilized. Nevertheless, the program applies the stretch factor as described above.

As discussed in more detail below, the program reports to the user when the claimant will be able to perform the tasks identified for his job. If the "healing satisfactorily" prognosis is entered after the last of these "task" dates, the program issues an action item instructing the user to obtain physician confirmation that the claimant can return to work.

4. Healing Slowly, Will Heal in Weeks, Will Heal in Months and Will Heal Eventually The last four prognoses ("healing slowly," "will heal in weeks," "will heal in months" and "will heal eventually") can also adjust a body part's profile, again depending upon when the prognosis is entered. Except for "healing slowly," the profile in each case ends in a 0% dysfunction value.

If "healing slowly" is entered before the original residual date, the engine determines a stretch factor equal to:

$$1+(0.33*(A/B)),$$

where A is the prognosis period, and B is the number of days in the original profile. The stretch factor is applied to the days in the original profile as described above with respect to the "healing satisfactorily" prognosis. As should be apparent from the stretch factor formula, the later the prognosis date, the greater the stretch factor. That is, a later "healing slowly" prognosis has a greater impact on the expected recovery than does an earlier prognosis.

For example, assume that the injury start date is January 1, the residual day is March 11 (day 70) and that the prognosis date is March 1 (day 60). The stretch factor is 1+(0.33*60/70), or 1.2829. Assume that the dysfunction level on day 25 is 97.83. Since day 25 is stretched by a factor of 1.2829, the 97.83 dysfunction level occurs at day 32 in the adjusted profile.

If the prognosis is "will heal in weeks," and the prognosis date is fourteen days before the residual date, the prognosis essentially agrees with the original curve, and no adjustment is made.

If the prognosis is "will heal in months," and the prognosis date is 61 days before the residual date, the prognosis essentially agrees with the profile, and no adjustment is made. If the user enters the number of months, the corresponding number of days is used instead of 61.

If the prognosis is "will heal eventually" and the prognosis date is 182 days prior to the original residual date, the prognosis essentially agrees with the profile, and no adjustment is made.

If the prognosis date for a "healing slowly" prognosis is after the original residual date, the engine calculates a stretch factor equal to the larger of the results of the two functions below:

$$1.33(A/B)$$

or $$(14+A)/B$$

If the prognosis is "will heal in weeks," and the prognosis date plus 14 days is before or beyond the original residual date, the stretch factor is (14+A/B).

If the prognosis is "will heal in months," and the prognosis date plus 61 is greater than the residual date, the stretch factor is (61+A/B). The user can enter the number of months, thereby overriding the 61.

If the prognosis is "will heal eventually," and the prognosis date plus 182 is before the residual date, the stretch factor is the lesser result of the following equations:

$$(182+\text{Residual Day Number})/\text{Residual Day Number, and}$$

$$(\text{Residual Day Number}+\text{Prognosis Period})/\text{Residual Day Number.}$$

If the prognosis date plus 182 is beyond the residual date, the stretch factor is the lesser result of the following equations:

$$(182+\text{Prognosis Period})/\text{Residual Day Number}$$

$$2(\text{Prognosis Period})/\text{Residual Day Number.}$$

For example, assume that the number of days in the original profile is 70 and that the prognosis "healing slowly" was entered on day 79. The first stretch factor function for this prognosis is 1.33*79/70=1.501. The second stretch factor function is (14+79)/70=1.329. The stretch factor is, therefore, 1.501.

The stretch factor is used differently for these prognoses than in the prior example. If a prognosis is applied directly to the day number, it is possible that the task dates and activity dates could fall before the prognosis date, particularly where the prognosis date is significantly beyond the original residual date. Thus, for these prognoses, the dysfunction level day (D) is moved to a day equal to D+E*(F−1)*(((D−G)/(E−G))**0.25), where E is the original residual date, F is the stretch factor calculated above, and G is the start date for the latest medical condition.

For example, assume that the injury start date is January 1 (day 1), that the original residual date is day 70 and that the dysfunction level on day 25 is 97.83. Applying the above function, day 25 becomes day 52:

$$25+70(1.501-1)(((25-1)/(70-1))**0.25).$$

The result of the equation is rounded to the nearest day. The equation is applied to each day in the original profile.

If, when the "task" dates are calculated, the prognosis date is greater than the latest task date, the engine issues an action item to the user for physician confirmation that the claimant may return to work.

5. Impairments

Impairments may be entered individually or as part of the first two recovery prognoses discussed above.

Regardless how the impairment is entered, the engine adjusts the applicable profile under the same routine.

6. Allocation of Prognoses and Impairments

Referring again to FIGS. 13A-13D, the engine allocates the effects of medical prognoses at 114 between the inheritance and build-up routines. Thus, if a user enters a prognosis after the program has run, the program executes another run.

Medical prognoses are always tied to a body part and relate to prior or concurrent medical conditions. If a medical prognosis is assigned (1) to a body part that is not injured and that has no medical component with medical conditions (i.e. with profiles), or (2) to a body part that has medical conditions applicable to itself or its components where all medical conditions start dates are later than the prognosis date, the prognosis is not applied to the body part. If a prognosis is assigned to a body part that has one or more medical conditions with start dates before the prognosis date, but that also has a treatment after the prognosis date, the model prompts the user to confirm that the prognosis should be applied despite the later treatment. Where no later treatments exist, the prognosis is applied without a prompt.

If a prognosis applies to a composite body part, the manner in which it is applied depends on the relationship between the composite and its components. If there are no composite profiles, but profiles exist for one or more components, the prognosis is applied to those components. If medical conditions apply both to the composite and one or more components, if any of the components are members of conjunction records, and if the composite's profiles are inherited to the components, the prognosis is applied only to those components having their own medical conditions. If, however, none of the components have their own medical conditions, the prognosis is applied to all components. In either case, the prognosis is applied to the composite's inherited profile(s) at the component level and is, therefore, applied to the composite by the subsequent build-up routine. If none of the components are members of conjunction records, the prognosis applies only to the composite. If the composite has medical conditions and those conditions are not inherited down, the prognosis is applied directly to the composite.

Impairments are applied at 115 following the build-up procedure. Impairments applied to composites are not passed down to the composite's children unless there is only one component. In the later case, the impairment value is divided by the component's grouping value prior to being applied to the component.

Only prognoses identified as "preferred" are applied. Generally, there could be only one preferred prognosis for a body part as the program executes.

D. Determining Activity Dates

As noted above, the engine predicts when the claimant can return to work. In general, and assuming use of the Task Wizard, the engine compares the employer's job requirements entered in the Task Wizard with the dysfunction levels established for the Little Man to estimate when those dysfunctions will allow the claimant to perform those tasks.

As discussed briefly above, body parts are related to activities in conjunction records, an example of which is provided below:

| Activity name | bending |
|---|---|
| body part | right hip, left hip, thoracic spine, lumbosacral spine |
| frequent dysfunction | 18%, 17%, 22%, 14% |
| infrequent dysfunction | 40%, 40%, 45%, 50% |
| frequent date | (derived by program) |
| infrequent date | (derived by program) |

This conjunction record identifies those body parts (right hip, left hip, thoracic spine and lumbosacral spine) that are used in the activity (bending) to which the conjunction record applies. There is a conjunction record for each activity listed in the Task Wizard.

The "frequent dysfunction" level is the maximum dysfunction level for the body part that will still allow the claimant to frequently perform the activity. This slot includes a "frequent dysfunction" value for each body part listed in the conjunction record. If the actual dysfunction level for any of the listed body parts is greater than or equal to its frequent dysfunction level, the claimant cannot frequently perform the activity. Similarly, the "infrequent dysfunction" levels are the maximum dysfunction levels that permit the claimant to perform the activity infrequently. The "frequent" and "infrequent" dates are the dates calculated by the engine, based on the Little Man, upon which the claimant will be able to frequently and infrequently perform the activity. Once the engine has generated profiles for all body parts and composites, including any medical prognoses, the engine determines at 160 the frequent and infrequent dates for each activity identified as part of claimant's occupation. For each activity, the engine examines the profile for each body part listed in the activity's conjunction record and identifies the dates upon which the frequent and infrequent dysfunction levels listed in the conjunction record are achieved in the profile for that body part. The frequent date for the activity is the latest frequent date found for the body parts. The activity's infrequent date is the latest infrequent date for the body parts.

For example, referring to the conjunction record shown above, if the 40% dysfunction level was reached for the right hip on March 1, the 17% dysfunction level for the left hip on March 1, the 22% dysfunction level for the thoracic spine on March 5 and the 14% dysfunction level for the lumbosacral spine on March 3, the infrequent date is March 5.

Conjunction records for two-sided activities include slots for non-sided and sided body parts. For example, the spine may be a non-sided body part listed in the conjunction record for "light lifting." "Arm" might be a two-sided body part, indicating that either the right or left arm could be used. To determine the activity date for this activity, the engine builds the profiles for the non-sided body parts as described above. It then builds profiles for each of the two body parts possible for the sided body parts. In the case of "arm," it builds profiles for the right arm and the left arm. In determining activity dates for each pair of sided body parts, the engine selects the lesser dysfunction value in the two original profiles for each day.

E. Activity Prognoses

Medical prognoses relate to particular body parts or composite body parts and may therefore be applied directly to the appropriate dysfunction profiles. In some cases, however, a physician submits a more general prognosis that addresses when the claimant may be able to perform certain activities. Accordingly, the engine uses these prognoses at 162 to adjust the activity dates (i.e. the frequent and infrequent dates) rather than the dysfunction profiles. Again, the user inputs activity prognoses through the Case Notebook as shown in FIG. 1.

The available activity prognoses are:
1. Avoid—at present
2. Avoid—permanently
3. Can do now
4. Can do infrequently at present
5. Can only ever do infrequently In one preferred embodiment, if activity prognoses are entered in a case in which recovery prognoses are present, the activity prognoses must be entered as part of, or added to, the "preferred" prognosis.

Since activity prognoses apply to activities rather than dysfunction curves, the prognosis period for a given activity prognosis is the number of days between the case start date and the effective date of the prognosis. In one embodiment, the case start date is the date of the earliest ICD9 code diagnosis, but in other embodiments it could be the earliest occurrence of the medical conditions to which the ICD9 codes apply.

If the "avoid at present" prognosis is entered, the engine first compares the prognosis date to the activity's infrequent date. If the prognosis date is significantly prior to the infrequent date, the prognosis essentially agrees with the calculated infrequent date, and no change is made to the infrequent or frequent dates. If the prognosis date is later than, or earlier than but close to, the infrequent date, then the prognosis indicates that the infrequent date may be inaccurate, and the engine changes both the infrequent and frequent dates.

To determine whether the activity dates should be changed, the engine increases the prognosis date by 33% and determines whether the new date is beyond the infrequent date. That is, is 1.33*(prognosis period) greater than the number of days between the case start date and the infrequent date? If it is, a new infrequent date is calculated according to the following rule:

new infrequent date=case start date+1.33* (prognosis period)

For example, if the case start date is January 1, and the prognosis date is March 6, the new infrequent date is January 1+1.33*(64)=March 27, provided the original infrequent date is before March 27. If the original infrequent date is after March 27, it is not changed. The frequent date is changed to a date equal to the new infrequent date plus the difference between the original frequent and infrequent dates. For example, if the activity's original infrequent and frequent dates are January 22 and January 26, respectively, the difference is four days. Since the new infrequent date calculated above is March 27, the new frequent date is March 31.

In some cases, a body part or a composite body part needed for an activity has a dysfunction profile that never reaches the frequent dysfunction level or that never reaches either the frequent or infrequent levels. Whenever this occurs, with or without activity prognoses, the engine inserts Dec. 31, 9999, for the appropriate date or dates. The engine reports "can never perform" in the return-to-work plan as appropriate.

In the above example, if the original infrequent date is Dec. 31, 9999, the prognosis date will not be close enough to the infrequent date to effect a change. If the activity has an infrequent date, but the frequent date is Dec. 31, 9999, the engine does not adjust the frequent date.

The program may notify the user when an activity prognosis changes the activity dates to indicate the claimant can perform an activity the engine had determined the claimant was presently unable to perform.

If the "avoid permanently" prognosis is entered, the engine changes both activity dates to Dec. 31, 9999. Again, a message may be produced for those activities that the engine had determined the claimant would be able to perform.

If the "can do now" prognosis is entered, and if the prognosis date is earlier than the infrequent date, the infrequent date is changed to the prognosis date. If the prognosis date is earlier than the frequent date, the frequent date is changed to the prognosis date. If either of the frequent or infrequent dates is earlier than the prognosis date, that date is not changed, since the program has already predicted that the claimant can do the activity. The program will notify the user, however, if this prognosis is entered for an activity where the frequent date, or both the infrequent and frequent dates, are Dec. 31, 9999.

If the "can do infrequently at present" prognosis is entered, and if the prognosis date is after the infrequent date, the infrequent date is unchanged since the program has already predicted that the claimant can do the activity infrequently. If the prognosis date is earlier than the infrequent date, the infrequent date is changed to the prognosis date. If the infrequent date is changed, the frequent date is changed by the same number of days. However, if the frequent date is Dec. 31, 9999, it is not changed. If the prognosis date is later than both the infrequent and frequent dates, the program changes the frequent date according to the following formula:

$$\text{new frequent date} = \text{infrequent date} + 1.5 * (\text{prognosis date} - \text{infrequent date})$$

For example, if the prognosis date is February 5, the infrequent date is January 29, and the frequent date is February 2, the new frequent date is January 29+1.5* (February 5 minus January 29)=January 29+10.5=February 9.

If the prognosis date falls between the frequent and infrequent dates, the engine makes no change to either date.

Before completing this part of the routine, however, the engine ensures that the frequent date does not follow the prognosis date too closely. It is possible, for example, that the frequent date resulting from the part of the routine described above may follow the prognosis date by only one or two days. It is unlikely that a physician would provide a "can do infrequently at present" prognosis if the patient were expected to perform the activity frequently in one to two days.

Thus, once the engine has determined a frequent date, whether it is changed or unchanged, according to any of the above-described rules, it compares that date with the result of the following function:

$$\text{case start date} + 1.33 * (\text{prognosis date} - \text{case start date}).$$

Assume the example set forth above wherein the new frequent date is February 9. The case start date is January 1, and the prognosis date is February 5. Applying the function, January 1+1.33*(February 5-January 1)=January 1+46.55=February 17. Since February 17 is later than February 9, the new frequent date is February 17. If the "can only ever do infrequently" prognosis is entered, and if the prognosis date is earlier than the infrequent date, the infrequent date is changed to the prognosis date. If the prognosis date is later than the infrequent date, the infrequent date is not changed since the program has already predicted that the claimant can perform the activity infrequently. The frequent date is changed to Dec. 31, 9999.

1. Pushing/Pulling and Lifting Activities

Additional rules apply to activity prognoses for pushing/pulling and lifting activities. These are actually groups of activities based on the weight of the object being lifted, pulled or pushed. For example, there are three pushing/pulling activities:

1. Pushing/pulling up to 50 pounds
2. Pushing/pulling up to 100 pounds
3. Pushing/pulling over 100 pounds These activities are hereinafter referred to as "pushing" activities.

There are five lifting activities:
1. Lifting small/light
2. Lifting up to 20 pounds
3. Lifting up to 50 pounds
4. Lifting up to 100 pounds
5. Lifting over 100 pounds It is possible that a physician might provide an activity prognosis for one of the pushing or lifting activities, but not the others. For example, a user may provide a "can only ever do infrequently" activity prognosis for lifting up to 50 pounds but provide no prognosis for lifting up to 100 pounds and lifting over 100 pounds, even though it is clear that those activities must have some restriction. Accordingly, the engine relates the activities within each of these groups so that an activity prognosis to one can affect others where no prognosis is otherwise entered.

The engine maintains tables, shown in FIGS. 11 and 12, that relate the pushing and lifting activities to the activity prognoses. Referring to FIG. 11, each row represents one of the five activity prognoses, and each column represents one of the three pushing activities. Three numbers are listed in each cell in the table. The numbers range from one to five and represent the activity prognoses as numbered at the left hand side of the table.

The numbers reflect activity prognoses that may be applied to activities above and/or below an activity to which a given prognosis is assigned if no activity prognosis is assigned to those other activities. Each number corresponds to the activity prognosis for the activity in the number's position. For example, "can do now" is the first prognosis. Thus, in the cells on its row, a "1" is placed in the first position in the first cell, in the second position in the second cell and in the third position in the third cell. The other positions in each of the three cells indicate the prognoses that should be applied to the activities represented by the respective positions. For example, assume that the prognosis "can do now" is assigned to the "up to 100 pounds" activity. The number list for this cell is "1, 1, 2." The "1" in the second position represents the given prognosis. A "1" is in the first position in the cell, and a "2" is in the third position. Thus, if the user has applied no prognoses to the "up to 50 pounds" and to the "over 100 pounds" activities, the engine applies a "can do now" prognosis to the "up to 50 pounds" activity and "can do infrequently" prognosis to the "over 100 pound" activity.

As an additional example, assume that a "can only ever do infrequently" prognosis is applied to the "over 100 pounds" activity. The applicable cell contains the numbers "1, 2, 4," where the "4" represents the "can only ever do infrequently" prognosis applied to the activity. If the user has entered no prognoses for the earlier two activities, the "1" indicates that a "can do now" prognosis is applied to the "up to 50 pounds" activity, and the "2" indicates that a "can do infrequently" prognosis is applied to the "up to 100 pounds" activity.

The same analysis applies to FIG. 12 regarding the lifting activities. As an example, assume that "can do infrequently" is assigned to "lifting up to 20 pounds" and that "avoid permanently" is assigned to "lifting over 100 pounds." Referring to the first activity, the appropriate cell is "1, 2, 3, 3, 3." The "2" in the second position refers to the prognosis applied to this activity. Referring to the second activity, the appropriate cell is "1, 1, 1, 4, 5." The "5" refers to the given prognosis.

As is clear from the figure, the estimated prognoses in the two cells do not match. For example, if the "avoid permanently" prognosis had not been given, the "can do infrequently" prognosis would have applied an "avoid at present" prognosis for each of the "up to 50" and "up to 100" activities. Had the "can do infrequently" prognosis not been given, however, the "avoid permanently" prognosis would have provided a "can do now" prognosis to the "up to 50" activity and a "can only ever do infrequently" prognosis to the "up to 100" activity. To reconcile the prognoses, the engine begins with the prognosis provided for the lowest activity. If there are no prognoses entered for activities below the given activity, the engine applies the prognoses for those activities as indicated in the cell. If there are no prognoses applied to activities higher than the given activity, the engine applies prognoses to those activities as indicated in the cell.

If there is a prognosis for one of the lower activities, then the prognoses for those activities will have been established by the routine as described below. Thus, the routine looks to the higher activities. If there is a prognosis for one of the higher activities, the engine determines the prognosis for the next higher activity by incrementally increasing the prognosis for each successive activity, until such prognosis conflicts with the next given prognosis. At that point, the prognosis level is maintained.

Taking the above example, there is a "can do infrequently" prognosis for "lifting up to 20 pounds." Since there is no prognosis for "light lifting," the prognosis for that activity is determined by the number in the appropriate position in the cell, in this case a "1." Thus, "can do now" is applied to "light lifting." The cell values are not applied to the higher activities, however, because a prognosis has been given for one of them—"avoid permanently" to "lifting over 100 pounds." To determine prognoses for "up to 50 pounds" and "up to 100 pounds," the engine incrementally increases the prognosis from that given to "up to 20 pounds." Since "can do infrequently" is given for "up to 20 pounds," "avoid at present" is assigned to "lifting up to 50 pounds." Since this prognosis is at or below the prognosis given for "over 100 pounds," the prognoses do not conflict. Thus, for "up to 100 pounds," the engine applies the next higher prognosis, "can only ever do infrequently," to "up to 100 pounds." This prognosis also agrees with the prognosis given for "over 100 pounds." Each of the activities now has a prognosis.

Changing this example, assume the same prognosis for "up to 20 pounds" but that "avoid at present" is given for "over 100 pounds." "Can do now" is still assigned to "light lifting," and "avoid at present" is again assigned to "up to 50 pounds." However, "can only ever do infrequently" would conflict with the prognosis given to "over 100 pounds" and is therefore not applied to "up to 100 pounds." It conflicts because a lesser activity cannot have a more severe prognosis than a greater activity. Thus, "avoid at present" is also applied to "up to 100 pounds."

2. Reasoning, Math and Language Activities

Each of these three activities is divided into five sub-activities, for example "minimal math," "light math," "moderate math," "heavy math" and "very heavy math." The prognosis table for each of these three activity groups is the same as for the lifting activity group as shown in FIG. 12.

If the user enters conflicting prognoses, for example "avoid at present" to "lifting up to 20 pounds" and "can do now" to "lifting up to 100 pounds," the engine does not apply either prognosis and notifies the user of the conflict.

3. Foot Amputations

If the claimant has suffered a partial foot amputation, the activity dates for climbing ladders and running, if applicable, are changed to Dec. 31, 9999. If a claimant has suffered a complete foot amputation, the activity dates for climbing ladders, climbing stairs, driving, lifting up to and over 100 lbs., repetitive leg movement, running, traversing difficult terrain and working at heights, if applicable, are changed to Dec. 31, 9999.

4. Embolisms

If a claimant has suffered an embolism, the engine assigns a frequent date for the sitting and standing activities, if applicable, equal to the greater of the frequent date as derived above and the end date of the embolism profile.

5. Above-the-Knee Amputation

If a claimant has suffered an above-the-knee amputation, the activity dates for climbing ladders, climbing stairs, crawling, driving, kneeling, lifting up to and over 100 lbs., pushing up to and over 100 lbs., repetitive leg movements, running, squatting, traversing difficult terrain and working at heights, if applicable, are changed to Dec. 31, 9999.

F. Task Dates

After defining the activity dates and applying the activity prognoses, the engine derives the task dates. Each task is comprised of one or more activities. The user may identify the activities applicable to each task through the Task Wizard, and the database contains a record for each task that identifies these activities. There are two slots in this record that respectively indicate whether the activity is key or transferable and whether it is frequently or infrequently required. The frequent/infrequent slot indicates to which date the engine refers in determining when that activity is available for the task. That is, if an activity is indicated as an infrequent activity for the task, its activity date is the activity's "infrequent date" as described above. A "key" task date is the latest of the activity dates for the activities defined in the task record as being key. An "all activities" task date is the latest activity date from all the activities, whether or not they are key. If the "key" and "all activities" dates are different, the engine reports both to the return-to-work plan. If they are the same, the engine reports a single date.

Before generating the return-to-work plan, however, the user has the opportunity to enter prognoses that apply to the occupations rather than the activities. Again, in one preferred embodiment, the prognosis should be entered with other prognoses as "preferred" prognoses. The available occupation prognoses are:

1. Currently unfit for any duties
2. Fit to resume full duties
3. Fit to resume for reduced hours
4. Fit to resume with restricted activities
5. Permanently unfit for full duties If the "currently unfit for any duties" prognosis is entered, the user can also enter the number of weeks that the claimant will be unfit for duty. If the prognosis date is later than the task date(s)+7, the task date (there will only be one, since the essential task date and the all activities date will now be the same) will be changed to the maximum of the following two functions:

prognosis date+7 or case start date+7*(number of weeks entered with prognosis)

The program will not change activity dates since the prognosis does not indicate what activities the claimant can and cannot do. The engine notifies the user if there are any tasks that the engine has predicted the claimant could already do at the time the prognosis was entered.

The "fit to resume full duties" prognosis indicates that the claimant should be able to perform all tasks as of the prognosis date. Thus, it is appropriate to change all activity dates later than the prognosis date to the prognosis date. It is not necessary to change activity dates prior to the prognosis dates since those dates already agree with the prognosis.

However, the engine does not change any activity dates that were established due to an activity prognosis as described above. That is, the activity prognoses take precedence over the occupation prognosis. It is therefore possible that, even after the "fit to resume full duties" prognosis, some activity dates may remain beyond the prognosis date so that the return-to-work plan reports one or more tasks dates that are also beyond the prognosis date. The engine reports to the user all activity dates that were changed as a result of this prognosis. It also reports any conflicts with activity prognoses.

If the user enters a "fit to resume on reduced hours" prognosis, the program again changes all activity dates beyond the prognosis date to the prognosis date, as long as the activity dates were not established by an activity prognosis. The program also reports activity changes and activity prognosis conflicts. The "fit to resume with restricted duties" prognosis requires that the user identify those duties that are to be restricted. To do this, the user must enter one or more activity prognoses that apply to the restricted activity(ies). If the user fails to enter activity prognoses with this occupation prognosis, the engine notifies the user that the occupation prognosis will be ignored.

For those activities not having an activity prognosis, either entered independently as described above or with this occupation prognosis, the model changes all activity dates that fall beyond the prognosis date to the prognosis date.

Again, the engine notifies the user of all activity date changes and activity prognosis conflicts.

If the "permanently unfit for full duties" prognosis is entered, all task dates are changed to "can never do." The model does not change activity dates, since the prognosis does not indicate which activities the claimant cannot perform. The engine notifies the user if it had otherwise predicted that the claimant could perform certain tasks.

G. Return-to-work Plan

Once the engine accounts for the occupation prognoses, it reports the task dates to the user as a return-to-work plan. The return-to-work plan identifies all the activity dates and task dates for activities and tasks listed under the claimant's occupation(s). If any of the tasks have different "key" and "all activities" dates, these are indicated.

Thus, the plan indicates when the claimant will be available to perform his former occupation, in whole or including only the key tasks.

Furthermore, all task dates must be beyond the latest "minimum return-to-work" date in the case. The database contains a minimum return-to-work days value, see column 6 of the Medical Body Parts.zip file in the electronic appendices, for each ICD9 code. For each code applicable to the case, the engine determines the date equal to the code's effective date plus the code's minimum return-to-work days. The latest of these dates is the latest minimum return-to-work date for the case. If any task date is before this date, the engine changes such task date to the latest minimum return-to-work date. Alternatively, the engine may print a warning to the final report, without changing task dates.

Of course, the engine may indicate that the claimant will never be able to perform his former occupation. Accordingly, the user may input alternate occupations that the engine processes simultaneously with the primary occupation. If the engine determines that the claimant should be able to perform one of the alternate occupations before the primary occupation, particularly if the claimant will never be able to perform the primary occupation, the employer may choose to move the claimant into the alternate job.

Alternatively, the user may wish simply to determine what tasks the claimant may be able to perform. In this case, the user identifies all the occupations to be used from the employer's database to create a constructed return-to-work plan. The engine provides a return-to-work plan with task dates for all applicable tasks so that the employer may choose among those tasks to which the claimant can return within a desirable period, thereby creating a new job for the claimant.

H. Dictionary of Occupational Titles

An employer not wishing to set up a database of its own tasks and activities may rely on the Dictionary of Occupational Titles (DOT) stored in the SQL server database. The DOT includes a list of occupations, for example "construction worker." For each occupation, it lists four "attributes": "lifting," "reasoning," "language ability" and "math ability." For each attribute, in turn, the DOT lists ability ratings. For example, for the "lifting" attribute, strength ratings might be "small," "light," "medium" and "heavy."

To construct a return-to-work plan using the DOT, the user identifies the claimant's occupation through the Case Notebook. The DOT ability ratings are a subset of the activities available through the Task Wizard. Thus, each ability rating is an activity that has a corresponding conjunction record. Since each DOT occupation is tied to respective attributes and ability ratings, identification of the DOT occupation identifies the conjunction records used to determine the return-to-work plan.

The DOT occupations do not distinguish among ability ratings as being frequent or infrequent. Thus, the engine calculates only frequent dates. Otherwise, the engine determines activity dates based on conjunction records identified by DOT occupations in the manner as described above for any other occupation.

If the DOT is used, the engine reports the activity dates for each ability rating of lower magnitude than those applicable to the occupation. For example, if a job requires "up to 100 pounds" lifting ability, the model also determines the activity dates for the lesser lifting abilities. The employer may thereby determine if a claimant can return to work earlier on lighter duties.

The engine outputs several prompts to the user encouraging the user to take further action. Some of these are described above. For example, the engine may prompt the user to verify medical data if a prognosis disagrees significantly with the engine's predicted results. Furthermore, if a prognosis changes one or more task dates so that the claimant is out of work much longer than otherwise expected, the engine prompts the user to verify the prognosis and to check the effect of the change on the insurance company's reserves. Additionally, assume a task includes two activities, and the engine determines that the claimant will be able to return to the first activity in two weeks but must wait six weeks to return to the second activity. The engine prompts the user to request that the employer decide whether the employer would like the claimant to return to work part time in two weeks.

All such prompts are displayed to the user as part of an action plan—i.e. a list of requests to the user to take steps beyond program activities. The triggers for any action plan prompt may be tailored to a given environment. In addition to the return-to-work plan and action plan, the engine displays case information, medical details, claimant details and prognosis information to confirm the information upon which the return-to-work and action plans are based.

III. Common Law

FIG. 16 describes the assessment process for common law cases. In common law assessments, the focus moves, generally, from dysfunction associated with medical conditions to medical condition severity. "Severity" as used herein refers to the magnitude of a medical condition's impact on an individual. In the presently-described embodiment, it is a unitless magnitude on a predefined scale. The model includes transition variables that correlate severity values to monetary amounts. Thus, a user may modify the variables to reflect changes in liability trends, or to allow the model's use in a different area, without requiring modification of each severity value.

SQL server database 12 (FIG. 1) includes a table that assigns a severity to each ICD9 code. The severities used for one preferred embodiment of the present invention are provided in column 8 of the Medical Body Parts.zip file in the electronic appendices. Thus, each medical condition represented by the ICD9 codes has its own severity value. The database additionally includes severities for conditions and events that may result from the ICD9 code medical conditions, for example hospital and convalescent care, future treatments and complications, loss of amenities and permanent and temporary dysfunction. The development of these severity measures is discussed in detail below.

If common law processing is selected at 31, the model determines an assessment of general damages at 200 and assesses a claimant's past and future lost income at 202 and 204, respectively. The model outputs these results in a common law assessment report at 206 and also displays an action plan, case information, medical details, claimant details and prognosis information at 208 to confirm the information upon which the assessment is based.

A. Medical Code Profiles

Upon starting a common law case, the engine again builds the Little Man. The procedure is similar to that described above with respect to workers' compensation, but there are differences. At 210, the model retrieves the dysfunction-v-time profiles associated with the ICD9 codes entered for the case. Thus, as in workers' compensation cases, each body part is described in terms of its dysfunction level at present and into the future. The default for all body parts is a zero dysfunction level. That is, the Little Man is assumed to be entirely healthy.

In the embodiment described herein, however, the profiles are based on workers' compensation assumptions. For example, the objective in a workers' compensation case is to assess when the claimant will be able to return to work. A common law case, on the other hand, assesses when the claimant will reach complete health. Accordingly, common law processing typically requires extension of the dysfunction profiles applicable to the common law case at 212.

To determine the adjustment for a given profile, the model relies on the ICD9 code's assumed stabilization days. Assumed stabilization days is a number assigned to each ICD9 code (see column 7 in the Medical Body Parts.zip file of the electronic appendices) that identifies the number of days in which the medical condition to which the code corresponds should reach its final resolution of symptoms. Once the model retrieves the profile for a given ICD9 code, it compares the profile's original period (i.e. the number of days in the original profile from the profile's beginning to the point at which MMI occurs) to the stabilization days for that ICD9 code. If the profile period is less than the stabilization days, and if the profile has a residual dysfunction, the engine adds a row to the profile to extend the profile to the stabilization days. For example, assume that an ICD9 code points to the following original profile:

| Profile Days | Percent Dysfunction |
|---|---|
| 0 | 100 |
| 14 | 100 |
| 21 | 60 |
| 28 | 40 |
| 35 | 30 |
| 42 | 20 |
| 49 | 10 |
| 56 | 5 |

The engine adds 0.1% to the dysfunction value at the profile's original end date (day 56) and extends the profile to the stabilization days at the original dysfunction value for the original end profile day. Thus, assuming that the stabilization days for this ICD9 code is 112, the model changes the dysfunction level at day 56 to 5.1 and adds a row to the profile listing day 112 at a 5% dysfunction.

If, however, the original profile ends with a 0% residual dysfunction, each day value $X_1$ in the original profile following the end of the initial plateau is changed to a day value $X_A$ according to the following equation:

$$(X_1-X_0)/(SD-X_0)=(X_A-X_0)(SD-X_0)$$

where $X_0$ is the last day of the initial profile and SD is the stabilization days value. In the above example, the initial plateau is a 100% dysfunction extending from day 0 to day 14. Accordingly, day 21 is the first day value that will be adjusted. In terms of the above equation, $X_1=21$, $X_0=14$ and SD=112. Thus, $X_A=((21-14)\(56-14))(112-14)+14=30.33$.

Rounding to the nearest whole day value, day 21 in the original profile is changed to 30. The dysfunction value, 60, does not change.

The engine repeats this process for each subsequent day value in the profile. $X_O$ and SD remain the same for each equation. Thus, to adjust day 28, $X_A=((28-14)\backslash(56-14))(112-14)+14=46.66$. Rounding to the nearest whole day value, day 56 becomes day 112.

It should be understood, however, that the profile may be adjusted in any suitable manner. For example, each profile day value may be multiplied by the ratio of the assumed stabilization days to the profile's original residual period.

If the assumed stabilization days is less than the profile's original residual period, the profile is not changed.

1. Inheritance

The inheritance routine described above with respect to workers' compensation cases is used to allocate the day-to-day dysfunction values from a composite body part to its component body parts. Common law cases, however, generally do not rely on dysfunction values. Accordingly, the common law routine does not execute an inheritance procedure.

2. Apply Profile Rules

Profile rules, for example the age/sex and age rules described above, are applied to the profiles at 214 as in workers' compensation cases.

3. Combining Multiple Profiles

The engine combines multiple profiles that exist for any individual body part through the procedure described above in workers' compensation cases. In workers' compensation, the manner in which multiple profiles are combined depends on the inheritance method. For example, if super gravity applies to a composite, multiple profiles for a component of that composite are combined using a combination of gravity and the selection of the highest dysfunction value for each day, depending on the type of profile being combined. If gravity does not apply, multiple profiles are amalgamated. In common law cases, however, there is no inheritance. At 215, multiple profiles that may exist for an individual body part are combined using the "type A/type B" procedure described above with respect to workers' compensation at 88 and 90 in FIGS. 13A-13D.

B. Prognoses

The engine applies prognoses to body part profiles at 216. In general, recovery prognoses and impairments are applied in a common law case as they would be applied in a workers' compensation case, with exceptions as set forth below. Where a common law case assesses economic loss, discussed in detail below, activity and occupation prognoses are also considered.

The common law processing also permits the user to enter future treatments and complications that the claimant may suffer. That is, as part of the prognosis data, the user may enter ICD9 codes relating to treatments and complications that a medical practitioner indicates may occur in the future. For each future treatment and complication, the user enters a code that reflects the probability that it will occur. In one embodiment, a future treatment or complication may be associated with one of three probabilities: "definite," "probable" and "possible." The definite probability indicates that the practitioner is confident the claimant will experience the treatment or complication. Accordingly, the engine applies 100% of the severity associated with the ICD9 code. The engine applies 60% and 25% of the severities associated with probable and possible treatments/complications, respectively.

The application of future treatment and complication prognoses is described in detail below. Preliminarily, however, the engine only considers an impairment or future treatment/complication prognosis if it is marked as preferred. Furthermore, in one embodiment, only one impairment prognosis, and only one future treatment/complication prognosis, may be marked as preferred. The user may, however, create a master prognosis that includes multiple other prognoses that are deemed necessary. Thus, by marking the master prognosis as preferred, the user allows the engine to consider multiple prognoses.

1. Recovery Prognoses

In contrast to workers' compensation cases, common law cases consider multiple recovery prognoses. Common law cases are more likely than workers' compensation cases to involve multiple injuries to multiple body parts or systems. It is, accordingly, more appropriate to consider multiple recovery prognoses.

The engine applies recovery prognoses based on rules that defer to certain medical practitioners and to more time-specific prognoses. Medical practitioners are classified into two general categories: physicians (specialists and general practitioners) and physiotherapists (chiropractors, physical therapists and osteopaths). For a given body part, the engine accepts those recovery prognoses, whether or not marked as preferred, that are assigned by a physician and that have a prognosis date greater than the latest medical occurrence date (i.e. dysfunction profile start date) for that body part. If a physician's recovery prognosis is applied to a body part having a medical condition with a start date later than the prognosis date, the prognosis is applied unless it is marked as preferred and has a severity greater than 500. In that case, the engine prompts the user to indicate whether the prognosis should be applied. The engine applies the prognosis only if the user affirmatively responds.

The engine also accepts those recovery prognoses provided by physiotherapists that are marked as preferred and that have a prognosis date greater than the latest medical occurrence date for the body part. If a preferred physiotherapist recovery prognosis has a start date that precedes a medical condition start date, the engine prompts the user to indicate whether the prognosis should be applied. The engine applies the prognosis only if the user affirmatively responds. Physiotherapist recovery prognoses not marked as preferred are not applied.

If the body part is a composite, each of its prognoses is applied to its components rather than to the composite, depending on the medical conditions applicable to each component. Specifically, the engine applies a composite's recovery prognosis to each of the composite's components that has a medical condition with a start date earlier than the recovery prognosis date. The engine assumes that a later medical condition invalidates the earlier prognosis. If none of the components have medical conditions, the prognosis is applied only to the composite. If the composite does not have its own medical conditions, the engine applies the prognosis to the components.

If an impairment is applied to a composite, and more than one of the composite's components have medical conditions, the engine applies the impairment only to the composite. If the composite, and only one of its components, are injured, the impairment applies only to the injured component. If no components are injured, the prognosis applies only to the composite.

If a body part has multiple prognoses, the engine applies the prognoses chronologically. That is, the engine modifies the body part profile for the first prognosis, modifies the resulting profile for the second prognosis, and so on. If the engine detects a conflict between two prognoses, it applies the later prognosis but notifies the user that the conflict has occurred. In the present embodiment, a conflict occurs where any prognosis follows an earlier prognosis indicating that MMI has been reached. For example, if a recovery prognosis indicates an injury is still healing for a body part that has already received a recovery prognosis indicating MMI has occurred, the engine applies the second prognosis and notifies the user. If the body part is a composite, the engine applies the second prognosis to the composite but not to its components.

As noted above, the algorithms for application of recovery prognoses are generally the same as described above with respect to workers' compensation processing. Certain of the compression and stretching algorithms are modified, however, to account for the possibility that multiple prognoses may be provided. Accordingly, a brief overview of the adjustment algorithms for the recovery prognoses is provided below.

Each recovery prognosis algorithm below is presented with an example based on the following assumptions. The case start date is January 1. For certain examples, where the prognosis date is before the residual date, the prognosis date is March 20. For other examples, where the prognosis date is beyond the residual date, the prognosis date is April 20. The residual date is April 10.

Accordingly, the residual period is 100 days, and the prognosis period is either 79 days or 110 days.

a. "Has Reached MMI" Recovery Prognoses

There is no change from the workers' compensation algorithm. For the five recovery prognoses indicating that the claimant has reached MMI, if the prognosis date is prior to the original residual date, the engine applies a compression factor equal to the prognosis period divided by the residual period. In the above example, the compression factor is 0.79.

b. "Healing Satisfactorily" Recovery Prognosis

This algorithm is unchanged from workers' compensation. If the prognosis date meets the requirements to stretch the profile, the engine multiplies each day number by a stretch factor. The stretch factor is equal to the greater of the following two functions:

$$1.11 * A/B$$

OR $$(7+A)/B,$$

where A is the prognosis period and B is the number of days in the original profile (residual period). In the example above, the results are 1.221 and 1.17, respectively, resulting in a stretch factor of 1.221.

c. "Will Heal in Weeks" Recovery Prognosis

This algorithm is unchanged from workers' compensation. If the prognosis date plus 14 days is before or beyond the original residual date, the stretch factor is $(14+A/B)$, where A is the prognosis period and B is the residual period. Assuming a March 20 prognosis date in the above example, the stretch factor is 0.93.

d. "Will Heal in Months" Recovery Prognosis

This algorithm is unchanged from workers' compensation. If the prognosis date plus 61 is greater than the residual date, the stretch factor is $(61+A/B)$, where A is the prognosis period and B is the residual period. The user can enter the number of months, thereby overriding the 61. Assuming a prognosis date of Mar. 20, 1998, and the default of 61 days, the stretch factor is 1.4.

e. "Will Heal Eventually" Recovery Prognosis

This algorithm is unchanged from workers' compensation. If the prognosis date plus 182 is before the residual date, the stretch factor is the lesser result of the following equations:

$$(182+B)/B \text{ and}$$

$$(B+A)/B,$$

where A is the prognosis period and B is the residual period.

If the prognosis date plus 182 is beyond the residual date, the stretch factor is the lesser result of the following equations:

$$(182+A)/B \text{ and}$$

$$2A/B,$$

where A is the prognosis period and B is the residual period.

f. "Healing Slowly" Recovery Prognosis

This algorithm has changed from workers' compensation. In the workers' compensation processing, if the prognosis date for a "healing slowly" prognosis is after the original residual date, the engine calculates a stretch factor equal to the larger of the results of the two equations below:

$$1.33(A/B) \text{ and}$$

$$(14+A)/B,$$

where A is the prognosis period and B is the residual period.

If there are multiple "healing slowly" prognoses in a common law case, this algorithm overly stretches the residual date. Accordingly, it is applied only if the prognosis is the last "healing slowly" prognosis. For earlier "healing slowly" prognoses, the model determines if (prognosis date/ residual date) is greater than two. If (1) this value is greater than two, the residual date is greater than the qualifying time (discussed below) and the prognosis has not yet been processed or (2) if the profile has a residual date greater than zero and the prognosis date is less than the residual date, the profile is not changed. Otherwise, the engine shrinks or stretches the curve by a factor equal to the maximum of:

$$1.11(A)/B \text{ and}$$

$$(7+A)/B,$$

where A is the prognosis period and B is the residual period.

The qualifying time is a measure of the residual date. It is set at the composite level to be equal to 21 days or the longest residual period among the composite and its components.

C. Determine General Damages

As indicated above, general damages assessments are based on severities and stabilization days for ICD9 code medical conditions and subsequent conditions and events resulting from such medical conditions. For each ICD9 code, the database assigns a severity between 0 and 300,000 and a stabilization day value. For example, a dislocated elbow has a severity of 8,000 with an assumed stabilization period of 84 days. That is, a claimant's dislocated elbow is expected to reach maximum medical improvement in 84 days with a pain and suffering severity of 8,000. In the presently described embodiment, the 0 to 300,000 scale is used for computational efficiency. As discussed in detail below, severities are converted to a 0 to 100 scale in converting to a monetary value.

Figure 17:
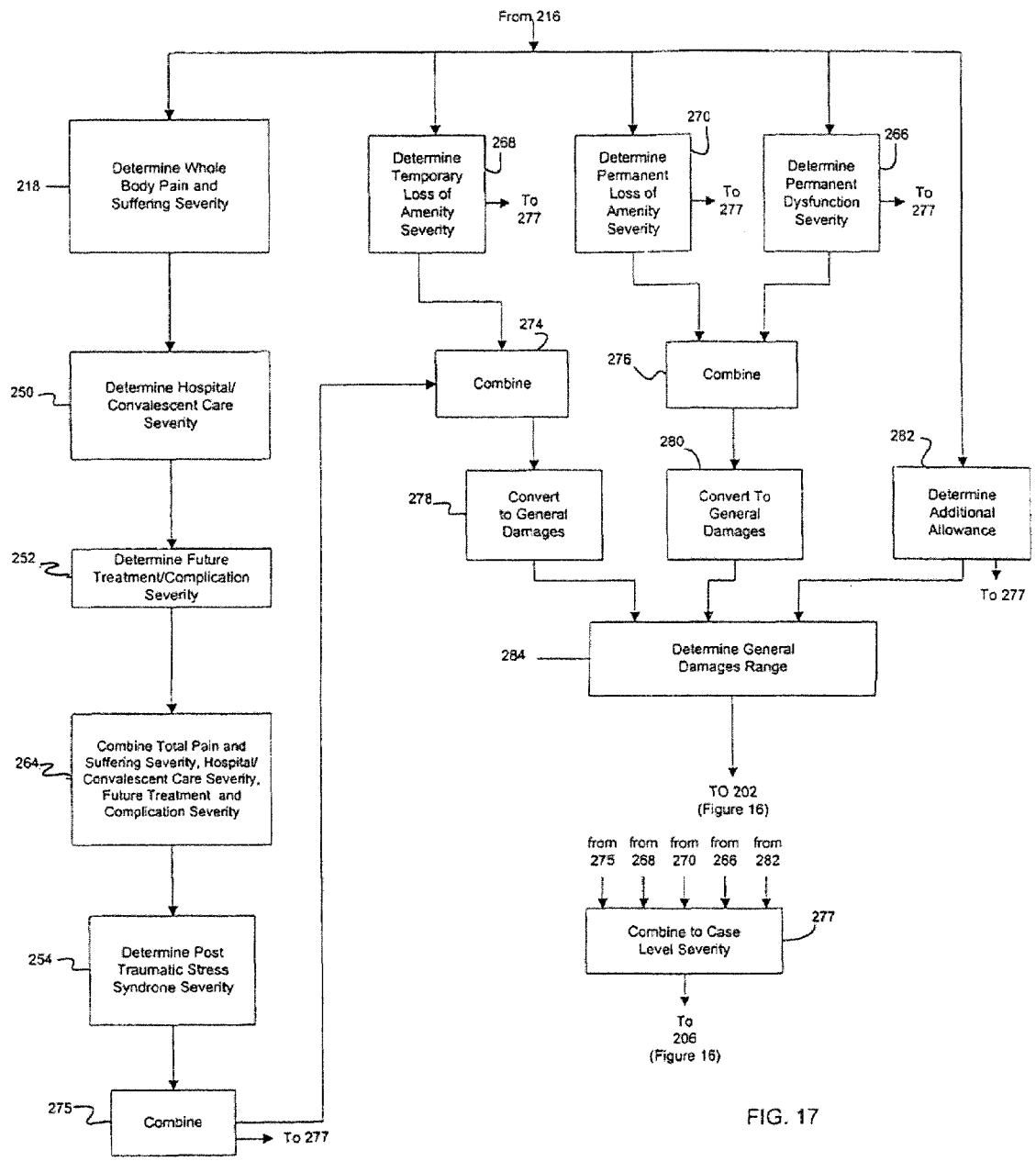
FIG. 17 is a flow chart illustrating the general damages step of FIG. 16.
Figure 18:
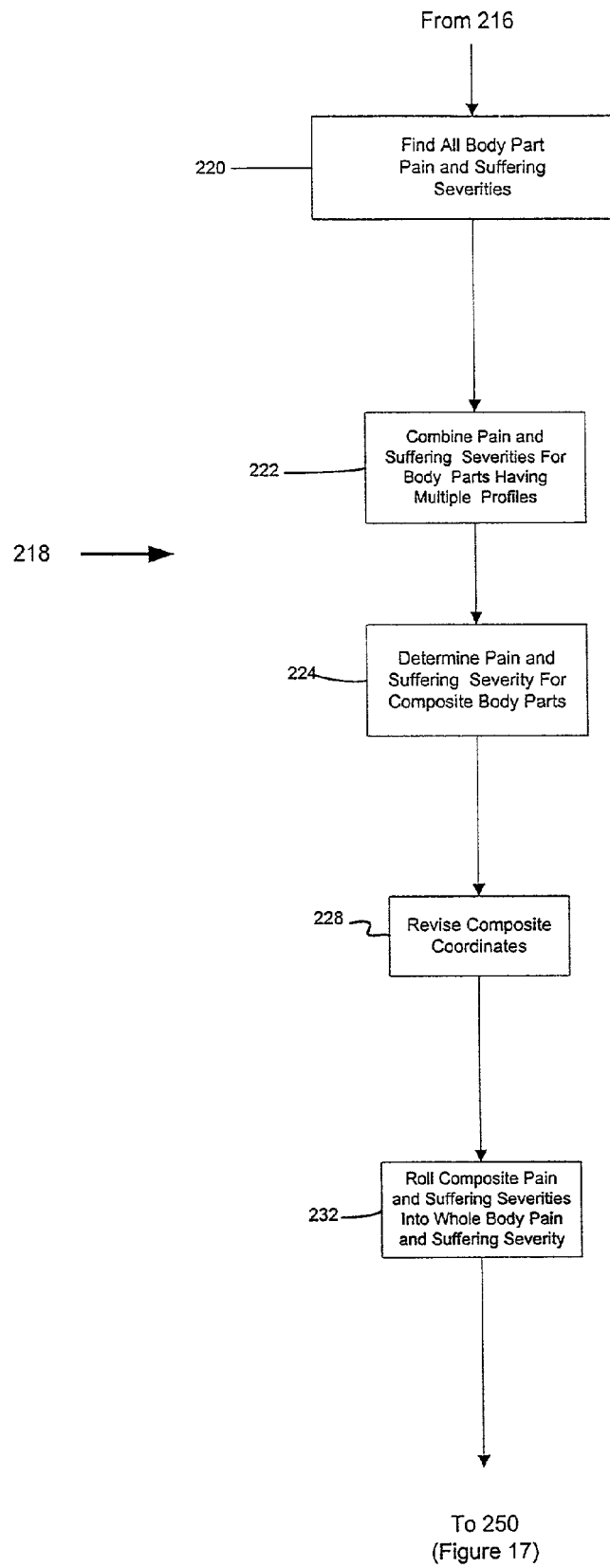
FIG. 18 is a flow chart illustrating the whole body pain and suffering step of FIG. 17.

1. Determine Whole Body Pain and Suffering a. Find Pain and Suffering Severity for Each Body Part FIG. 17 illustrates general damages step 200. Following application of prognoses at step 216 (FIG. 16), the model determines whole body pain and suffering severity at 218. This procedure is more specifically illustrated in FIG. 18. At this point, the engine has determined a single dysfunction profile, adjusted for stabilization days and to account for any prognoses that may apply, for each body part to which a medical condition (i.e. profile) applies. The residual period of the resulting profile is now considered the body part's "actual stabilization days."

The profile combination did not, however, combine severity values. Thus, at 220, a body part with multiple medical conditions still has multiple severity values, even though it now has a single profile. The first step in determining the severity for the whole body is, therefore, to determine at 222 a total severity for each body part. This procedure employs the gravity algorithm discussed above with respect to workers' compensation cases.

As an example, assume that a claimant's left elbow has suffered a dislocation injury, a villonodular synovitis complication and a reduction treatment. The injury dates, stabilization days and severities for these medical conditions are provided below:

Left Elbow Dislocation Injury
(832.01.L)
Injury Date Jan. 1, 1998
Stabilization Days: 84
Severity: 8000
Left Elbow Villonodular Synovitis
Complication (719.22.bL)
Complication Date May 15, 1998
Stabilization Days: 21
Severity: 2000
Left Elbow Reduction Treatment
(79.82.L)
Treatment Date Jan. 1, 1998
Stabilization Days: 98
Severity: 2500

As discussed above with respect to workers' compensation, the gravity algorithm combines a given aspect, such as dysfunction or severity, of coexisting conditions for a given entity, or for multiple entities, such as body parts, composite body parts or the whole body, taking into consideration the effect of the conditions on each other. The determinative relationship among the aspects being combined may vary with the aspect but is reflected in the gravity algorithm by the location and distance values. For example, workers' compensation cases focus on body part dysfunction resulting from medical conditions. The effect of one dysfunction on another depends on the spatial relationship of the dysfunctions, i.e. how far apart they are from each other in the Little Man. Thus, the determinative relationship among medical conditions in workers' compensation is their spatial separation. For example, the dysfunction effects of two injuries at opposite ends of the body may be nearly additive, whereas two injuries close together may more nearly approach the effect of a single injury. Accordingly, the "location" and "distance" values in workers' compensation gravity calculations relate to the spacial position of medical conditions in the body.

In contrast, common law cases generally focus on severity. For multiple medical conditions applicable to a single body part, time is the determinative relationship with respect to severity. For example, the cumulative body part severity of injuries that occur at different times is more nearly additive, whereas the severity of simultaneous medical conditions is closer to the severity of a single condition. Accordingly, the location value used in the gravity routine for combining multiple severities for a body part is based on stabilization time. More specifically, the location value is proportional to the start date of the medical condition:

5(effective date−case start date)/included stabilization time, where included stabilization time is the stabilization days for the first-occurring medical condition, typically an injury or treatment occurring at the beginning of the case. Accordingly, the location of each medical condition is its time ratio to the first-occurring condition.

Referring to the above example, the dislocation injury and reduction treatment occur on January 1. Both of these conditions could be considered the first-occurring condition. To determine included stabilization, the engine chooses the condition having the maximum assumed stabilization days, in this case the treatment. Accordingly, included stabilization time is 98 days. Using the above equation, the location for the injury is 0, and the location for the complication is 6.837.

The location for the reduction treatment, and for all treatments, is 1. As described in detail below, treatments are combined separately from complications and injuries. That is, the engine applies gravity for all complications and injuries as a group, then applies gravity for all treatments. The result of the complication/injury combination is then combined with the treatment result.

The gravity algorithm employs the following variables.

Local Absolute Mass$(j)=((100-\text{valuelist}(j))/100)^k$,
where valuelist$(j)$ is the severity value, divided by 3,000, for medical condition $j$.

Mass difference$(j,k)=(\min(\text{valuelist}(j), \text{valuelist}(k)/\max(\text{valuelist}(j), \text{valuelist}(k))^g$, where valuelist(j) is the severity, divided by 3,000, of medical condition j, valuelist(k) is the severity, divided by 3,000, of medical condition k, and g is equal to 1. The local absolute mass variable applies to each medical condition individually, whereas the mass difference variable applies to medical condition pairs. Thus, assuming there are four medical conditions, there are four local absolute mass values and six mass difference values.

The engine then determines the "distance" between two severity masses as the difference in their locations. The routine determines the distance between severity j and each other severity k according to the equation:

Distance$(j,k)=abs(\text{location}(j)-\text{location}(k))$, where location(j) is the location of medical condition j, and location(k) is the location of medical condition k.

The routine then begins to determine the impact of each other medical condition k on medical condition j. This is inversely proportional to the distance between medical conditions j and k. The "distance effect" relates to the degree to which the distance between two medical conditions affects their impact on each other:

Distance Effect$(j,k)=(1/\text{Max}(\text{Distance}(j,k)+5),2)^d$, where d is 2. Since the smallest possible value for distance is 0, this equation will always be $(1/\text{distance}(j,k)+5)^d$, and therefore cannot be less than 0.04.

The routine then determines the impact of a medical condition k on medical condition j by the following equation:

Impact(j,k)=(1−(Mass Diff(j,k)*Loc Abs Mass(j)*
  Distance Effect(j,k) 2.

Since there is an impact of each medical condition on medical condition j, the routine generates an impact number for medical condition j for each of the other medical conditions.

The routine finds a "new mass" number for medical condition j. This is the severity for medical condition j, considering the impact of the other medical conditions. The routine first sorts the impact numbers for the other medical conditions from smallest to highest and assigns each number an index k, beginning at the smallest impact number, sequentially from 1 to M, where k is an integer and where M is the number of other medical conditions. To determine "new mass" for medical condition j, the routine executes the following function:

Loc New Mass(j,k)=Loc New Mass(j,k−1)*(1−((1−
  Impact(j,k))/k)), for k=1 to M, where Loc New Mass(j,0) is valuelist(j), and where New Mass(j)=Loc New Mass (j,M).

The routine determines a Loc New Mass value for each medical condition. It then manipulates this value according to the following equation:

New Mass(j)=Loc New Mass(j)*100/Bound, where Bound is a value determined by the following equation:

Bound=2Σ$_{j=1}^{M}$, valuelist(j), where valuelist(j) is the severity value, divided by 3,000, for medical condition j and where M is the total number of medical conditions. As indicated above, injuries and complications are combined separately from treatments. Accordingly, a Bound value is determined for the injury and complication conditions, without consideration of treatments. The engine also determines a Bound value for treatments.

Following the manipulation of the Loc New Mass values, the routine has a New Mass value for each medical condition, including injuries, complications and treatments. The routine now amalgamates the New Mass values for (1) injuries and complications and (2) treatments.

The amalgamate function is:

X(n)=X(n−1)+((1−x(n−1))New Mass(n)), for n=1 to M, where M is the number of New Mass values being combined, New Mass(1) is the first of those values and X(0)=0. The result, X(M), is the combined severity value. New Mass values are converted to a decimal format prior to amalgamation. The routine then modifies the amalgamate results to back out the bound factor and the decimal conversion and to convert the severity values back to a 0 to 300,000 scale:

Z(I/C)=(X(I/C)Bound(I/C)/100)3000 and

Z(T)=(X(T)Bound(T)/100)3000, where X(I/C) and X(T) are the amalgamate results for the injuries/complications and for the treatments, and Bound(I/C) and Bound(T) are the bound values for the injuries/complications and for the treatments, respectively. The results, Z(I/C) and Z(T), are summed to arrive at a single severity value, on a 0 to 300,000 scale, for the body part.

Referring to the left elbow injury, complication and treatment described above, the determination of the left elbow's total body part severity is set forth below. As discussed above, the injury/complication calculation parallels the treatment calculation. In this example, since there is only one treatment, the treatment severity is brought directly down to the final treatment severity, Z(T). The final injury/complication severity, Z(I\C), is 8,860. Thus, the total body part severity is 11,360.

|  | Injury | Complication | Treatment |
|---|---|---|---|
| Valuelist | 2.667 | 0.667 | 0.833 |
| Location | 0 | 6.84 | 1.0 |

Loc Abs Mass(I)=(100−2.667)/100=0.973

Loc Abs Mass(C)=(100−0.667)/100=0.993

Loc Abs Mass(T)=(100−0.833)/100=0.992

Mass Diff(I,C)=min(2.667,0.667)/max(2.667,0.667)
  =0.25

Mass Diff(T,_)=N/A

Distance(I,C)=Distance(C,I)=Abs(0−6.84)=6.84

Distance(T,_)=N/A

Distance Effect(I,C)=1/max(6.84+5,2)=0.084

Distance Effect(T,_)=N/A

Impact(I,C)=(1−(0.25*0.973*0.084))$^2$=0.960

Impact(C,I)=(1−(0.25*0.993*0.084))$^2$=0.959

Impact(T,_)=N/A

Loc New Mass(I)=2.667(1−((1−0.960)/1))=2.560

Loc New Mass(C)=0.667(1−((1−0.959)/1))=0.640

Loc New Mass(T)=N/A

Bound(I/C)=2(2.667+0.667)=6.667

Bound(T)=2(0.833)=1.667

New Mass(I)=2.560*100/6.667=38.398

New Mass(C)=0.640*100/6.667=9.585

New Mass(T)=N/A

X(1)=0+(1−0)(38.398/100)=0.38398

X(2)=X(I/C)/100=0.38398+(1−0.38398)(9.585/100)
  =0.443

X(I/C)=44.3

X(T)=N/A

Z(I/C)=(44.3*6.667/100)3000=8860

Z(T)=2500

Total Body Part Severity=8860+2500=11,360

The routine stretches the body part severity if circumstances indicate that the assumed stabilization days for any of the medical codes is too short. This occurs where the effective date of a treatment or complication is beyond the date at which all prior injuries, complications and treatments should have stabilized. In this case, one or more of the earlier injuries, treatments and complications has failed to stabilize at least as late as the effective date of the new treatment or complication. Thus, the claimant has suffered some medical condition during the interim period for which no severity has been included.

If there are more than one of the earlier medical conditions, the routine does not know which has extended beyond its assumed stabilization time. Accordingly, the routine determines the severity to be applied to the interim period based on the following severity curve:

| Days | Severity |
|------|----------|
| 0    | 0        |
| 1100 | Total Body Part Severity |

To determine the added severity, the routine determines the severities for the assumed stabilization period and the actual stabilization period from the above curve. The difference between these severities is then added to the body part severity. Referring again to the above example, the stabilization days for the left elbow injury and treatment are 84 and 98, respectively. Both start on January 1. Thus, both the injury and treatment are expected to have stabilized by the 98th day. The complication's stabilization days is 21 and does not overlap the injury or treatment. Thus, the assumed stabilization period is the total number of non-overlapping stabilization days, or 119.

The complication is diagnosed on May 15, 134 days after the case start date of January 1. Since its stabilization days is 21, the length of the case is 155 days. To determine the body part's severity adjustment, the routine determines the severities for 119 and 155 day periods on a linear curve extending 1100 days between severities of 0 and 11,360 (the total body part severity determined above) and finds the difference between those severities. If the total body part severity is greater than 14,000, the curve is capped at 14,000. Solving the following equations for $X_1$ and $X_2$:

$$(1100-0)/11,360-0)=(155-0)/(X_1-0)$$

$$(1100-0)/11,360-0)=(119-0)/(X_2-0),$$

the severity for day 155, $X_1$, is 1601, and the severity for day 119, $X_2$, is 1,229. The difference between these severities is 372. Thus, the total body part severity is changed from 11,362 to 11,734.

Finally, the above example did not include prognoses. Prognoses may change the length of the medical condition profiles, thereby changing the assumed stabilization days. Where this occurs, the assumed stabilization days is not the stabilization days associated with the ICD9 code as in the database, but is instead the period of the medical condition's profile as affected by the prognoses. Recall, however, that while the engine modified body part profiles at 216, it did not modify severities. Severity adjustments are discussed below.

B. Determine Pain and Suffering Severity For Each Composite, Including Effect of Component Pain and Suffering Severities.

Referring again to FIG. 18, the engine has found all body part pain and suffering severities at 220 and combined multiple profiles for all body parts at 222. At 224, the engine rolls component severities into their composites. If a composite is itself a component of a higher-order composite, the engine rolls its components' severities up before rolling the composite up to the higher-order severity. The engine again employs a gravity algorithm. Here, however, the time relationship among severities has been accounted for at the body part level, and the determinative relationship is the spatial relation among the body parts. Accordingly, the location and distance values reflect body part positions within the Little Man.

As an example, assume that, in addition to the dislocation injury, villonodular synovitis complication and reduction treatment to the left elbow, the left arm receives a nerve decompression treatment on January 1 and the left forearm suffers an ulnar nerve compression injury on January 1. The start dates, stabilization days and severities for each of these medical conditions is set forth below.

Left arm (composite)
Nerve Decompression Treatment (04.49.Bcl)
Start Date Jan. 1, 1998
Stabilization Days: 112
Severity: 1000
Left Elbow (component)
Dislocation Injury (832.01.L)
Start Date Jan. 1, 1998
Stabilization Days: 84
Severity: 8000
Villonodular Synovitis Complication (719.22.bl)
Start Date May 15, 1998
Stabilization Days: 21
Severity: 2000
Reduction Treatment (79.82L)
Start Date Jan. 1, 1998
Stabilization Days: 98
Severity: 2500
Left Forearm (component)
Ulna Nerve Compression Injury (955.2.Lcl)
Start Date Jan. 1, 1998
Stabilization Days: 182
Severity: 12,500

Assume also that there is a "healing slowly" prognosis applied to the left arm on May 1, 1998. Assuming that the left elbow and left forearm are the only left arm components having medical conditions, the prognosis is passed only to them. The left elbow, however, has a treatment with an effective date beyond the prognosis date. Thus, the prognosis is only passed to the forearm. Accordingly, the stabilization days for the left arm and for the left forearm reflect an adjustment due to the prognosis.

The left elbow medical conditions are the same as given in the body part combination example above. Thus, as explained in the example, the total left elbow severity is 11,734. There is only one medical condition applicable to the left forearm, with a severity of 12,500. Since it is the only medical condition, the total severity for this body part remains 12,500. The severity is adjusted, however, because of the "healing slowly" prognosis.

The adjustment is based on the residual date adjustment made at 216. Since the prognosis date is before the medical condition's residual date, the residual date stretch factor is 1+0.33 (A/B), where A is the prognosis period and B is the original residual period. The prognosis effective date is May 1, 120 days after the case start date, January 1. The residual date is 182 days after the case start date. Accordingly, the stretch factor is 1+0.33(120/182)=1.218. Thus, the new residual date, adjusted at 216 for the prognosis, is 182*1.218=222. The model determines the prognosis severity adjustment according to the following severity curve:

| Days  | Severity           |
|-------|--------------------|
| 0     | 0                  |
| 1,100 | Total Body Part Severity |

The assumed residual date was day 182, while the actual residual date was day 222. The severity adjustment is the difference between the severities calculated on the curve for these days. Interpolating for days 222 and 182, the severity values are 2,523 and 2,068, respectively. The difference, 455, is the severity adjustment added to the total forearm severity, 12,500, resulting in a final forearm severity of 12,955.

The initial left arm severity is determined in the same manner as any other body part. Since there is only one medical condition, the initial total severity for the left arm is simply the severity for the medical condition, 1,000. There is, however, an adjustment to the left arm's severity for the "healing slowly" prognosis. This is not an adjustment to the left arm's dysfunction profile. As discussed above, composite prognoses that are passed to components are not applied to the composite's dysfunction profile since the composite profile itself would have been passed to the components (in a workers' compensation case). Thus, the prognosis's effect on the composite profile is applied at the component level. Composite severities, however, are not inherited to components. The composite prognosis is, therefore, applied to the composite severity.

The severity adjustment does, however, use the profile stretch equations to determine the difference between assumed and actual stabilization. The "healing slowly" algorithm stretches the left arm profile from 112 to 161 days. Since the prognosis applies to both the left arm and the left forearm, however, the routine looks to the duration of both curves after adjustment for the prognosis. Both start on January 1.

The left arm profile ends at 161 days, but the left forearm curve ends in 222 days. Thus, the latest date to which the prognosis stretches a curve to which it applies is 222 days. If the composite's stretched profile ends before this date, the model assumes that the effect of the prognosis on the composite should also extend to this date, and the composite's profile is stretched accordingly. Thus, since the forearm and arm profiles start on the same date, the arm's profile is stretched to 222 days.

Applying the stretch from 112 days to 222 days to the following linear severity adjustment curve:

| Days  | Severity |
|-------|----------|
| 0     | 0        |
| 1,100 | 1,000    | the severity on day 222 is 202, and the severity on day 112 is 102. Accordingly, the severity adjustment is 100, and the final severity for the left arm composite prior to consideration of the component severities is 1,100.

To combine the severities for the composite and its components, the model again uses a variation of the gravity routine discussed above. In combining the severities for a single body part, the spatial location of the severities was the same, and the determinative factor for the combination was the time duration of the severities. As a result of the body part combinations, each body part has a severity value on a scale that is comparable to that of each other body part with respect to time. In combining the severities from one body part to another, the determinative factor is spatial distance.

The gravity algorithm applies to all composite/component severity combinations, and the model therefore considers the three-dimensional position of the body parts with respect to each other. Accordingly, in determining the location of each body part, the model refers to its coordinates as described with respect to a three-dimensional Cartesian space centered at the base of the spine. That is, the Little Man is mapped so that each body part has X, Y and Z coordinates in a space defined such that the 0,0,0 position is at the base of the spine. The mapping describes the body in a sitting position with its parallel legs extending straight from the torso. The arms are also parallel and extend straight forward from the torso, parallel to the legs. The palms of the hands and the soles of the feet face forward, so that the fingers and toes point upward. The coordinates of each body part are listed in columns 8, 9 and 10 of the file Body_Part.rpt of the electronic appendices.

The coordinates of the left arm and its five components, and the coordinates for two of the left arm components that are themselves composites, are set forth below.

|                     | X   | Y | Z  |
|---------------------|-----|---|----|
| Arm Composite       |     |   |    |
| left arm            | 3   | 9 | −3 |
| left shoulder       | 1   | 7 | −3 |
| left upper arm      | 2   | 7 | −3 |
| left elbow          | 3   | 7 | −3 |
| left forearm        | 4   | 7 | −3 |
| left wrist and hand | 5.5 | 7 | −3 |
| Wrist and Hand Composite |     |   |    |
| left wrist and hand | 5.5 | 7 | −3 |
| left wrist          | 5   | 7 | −3 |
| left hand           | 6   | 7 | −3 |
| Hand Composite      |     |   |    |
| left hand           | 6   | 7 | −3 |
| left palmer hand    | 7   | 7 | −4 |
| left dorsal hand    | 6   | 8 | −4 |
| left thumb          | 6   | 9 | −2 |
| left index          | 6   | 9 | −3 |
| left middle         | 6   | 9 | −4 |
| left ring           | 6   | 9 | −5 |
| left little         | 6   | 9 | −6 |

Referring to the arm composite, the components extend linearly along the X axis but are in the same position on the Y and Z axes. The coordinates for the arm composite, however, do not lie at the center of the component coordinates. That is, while the composite's X coordinate is approximately centered within the range of component X coordinates, and while the composite's Z coordinate is the same as each of the component coordinates, the Y coordinate is offset from the component Y coordinates. Thus, the position given for the arm as a whole is offset from the collective positions of its components. The offset tunes the distance between the arm composite and each component so that they have an appropriate effect on each other during the build-up described below. Component values may also be adjusted to achieve an appropriate relationship.

There are only two components in the wrist and hand composite, and the appropriate position for the composite is midway between the two.

Accordingly, while body part positions in the Little Man are based on the actual positions of body parts in the human body, the mapping does not exactly correspond to the human body. Relatively slight variations are included to facilitate assessment of the effects of body part medical conditions among each other.

The gravity algorithm that combines component severities with composite severities is similar to the gravity algorithms described above, primarily except for the distance calculation, which relies on Euclidean distance rather than one-dimensional linear distance or the difference between time-based location values. This "three-dimensional" gravity routine is described by the equations below:

Loc $Abs$ Mass$(j)=((100-\text{valuelist}(j))/100)^k$, where valuelist(j) is the severity value (divided by 3,000) for component j and where k=1.

Mass Diff$(j,k)=(\min(\text{valuelist}(j),\text{valuelist}(h))/\max(\text{valuelist}(j),\text{valuelist}(h)))^g$, where g=1.

Distance$(j,k)=(X(j)-X(k))^2+(Y(j)-Y(k))^2+(Z(j)-Z(h))^2$, where X(n), Y(n) and Z(n) are the X, Y and Z coordinates, respectively, of body part n.

Distance Effect$(j,k)=(1/\max(\text{Distance}(j,k)+5),2)^d$, where d=1.

Impact$(j,k)=(1-($Mass Diff$(j,k)*$Loc $Abs$ Mass$(j)*$ Distance Effect$(j,k)))^2$.

Loc New Mass$(j,k)=$Loc New Mass$(j,k-1)*(1-((1-$Impact$(j,k))/k)$, for k=1 to M for Loc New Mass in ascending order, where M is the number of component/composite body parts being combined, Loc New Mass(j,o)=valuelist(j), and Loc New Mass(j)=Loc New Mass(j,M).

New Mass$(j)=$Loc New Mass$(j)*100/$Bound, where Bound=$2\Sigma^M_{j=1}$, valuelist(j) and M is the number of component/composite body parts being combined.

$X(n)=X(n-1)+((1-X(n-1))*$New Mass$(n))$, for n=1 to M, where M is the number of body parts being combined, and where New Mass(n) is adjusted to decimal value.

Total Severity=$X(M)*($Bound$/100)*3,000$, where X(M) is backed out of decimal value.

Returning to the example above, the left arm composite has a total severity of 1,100, while the left elbow and left forearm components have severities of 11,734 and 12,955, respectively. Thus, the coordinates and severities for the arm and its components are as follows:

|  | X | Y | Z | Severity/3,000 |
|---|---|---|---|---|
| left arm | 3 | 9 | −3 | 0.0333 |
| left shoulder | 1 | 7 | −3 | 0 |
| left upper arm | 2 | 7 | −3 | 0 |
| left elbow | 3 | 7 | −3 | 3.911 |
| left forearm | 4 | 7 | −3 | 4.318 |
| left wrist and hand | 5.5 | 7 | −3 | 0 |

The arm severity is 0.0333, instead of 0.3667, because the treatment severity of 1,000 is not considered in this portion of the routine. The treatment at the composite body part level is not specific to the composite. The composite body part is not injured, and the treatment is actually against one of its components. Where multiple components are injured, it is unclear to which component the treatment should apply. Without knowing the proper distance relationships the engine does not apply the compressions to the treatment that would result from the gravity algorithm, and the treatment severity is therefore excluded during this portion of the buildup. Thus, the arm severity in the table above is 100/3,000. The treatment severity is included at a later step.

Executing the gravity algorithm for the left arm (A), left elbow (E) and left forearm (F), Valuelist$(A)=0.0333$ Valuelist$(E)=3.911$ Valuelist$(F)=4.318$ Loc $Abs$ Mass$(A)=(100-0.0333)/100=0.9997$ Loc $Abs$ Mass$(E)=(100-3.911)/100=0.961$ Loc $Abs$ Mass$(F)=(100-4.318)/100=0.957$ Mass Diff$(A,E)=\min(0.0333,3.911)/\max(0.0333,3.911)=8.519\times10^{-3}$ Mass Diff$(A,F)=\min(0.0333,4.318)/\max(0.0333,4.318)=7.711\times10^{-3}$ Mass Diff$(A,F)=\min(3.911,4.318)/\max(3.911,4.318)=0.9057$ Distance$(A,E)=(3-4)^2+(9-7)^2+(-3+3)^2=4$ Distance$(A,F)=(3-4)^2+(9-7)^2+(-3+3)^2=5$ Distance$(E,F)=(3-4)^2+(7-7)^2+(-3+5)^2=1$ Distance Effect$(A,E)=1/\max(4+5),2)=0.111$ Distance Effect$(A,F)=1/\max(5+5),2)=0.100$ Distance Effect$(E,F)=1/\max(1+5),2)=0.167$ Impact$(A,E)=(1-8.514\times10^{-3}*0.9997*\ 0.111)^2=0.9981$ Impact$(E,A)=(1-8.514\times10^{-3}*0.961*\ 0.111)^2=0.9982$ Impact$(A,F)=(1-7.711\times10^{-3}*0.9997*\ 0.100)^2=0.9985$ Impact$(F,A)=(1-7.711\times10^{-3}*0.957*\ 0.100)^2=0.9985$ Impact$(E,F)=(1-0.9057*0.961*\ 0.167)^2=0.7304$ Impact$(F,E)=(1-0.9057*0.957*\ 0.167)^2=0.7315$ Loc New Mass($A$)=0.0333(1−((1−0.9981)/1) (1−((1−0.9985)/2)=0.03321

Loc New Mass($E$)=3.911(1−((1−0.7304)/1) (1−((1−0.9982)/2)=2.8540

Loc New Mass($F$)=4.3183(1−((1−0.7315)/1) (1−((1−0.9985)/2)=3.1565

Bound=2(0.0333+3.911+4.318)=16.52

New Mass($A$)=0.03321*100/16.52=0.2010

New Mass($E$)=2.8540*100/16.52=17.28

New Mass($F$)=3.1565*100/16.52=19.11

$X$(1)=0+(1−0)(0.2010/100)=0.002010

$X$(2)=0.002010+(1−0.002010)(17.28/100)=0.1745

$X$(3)=0.1745+(1−0.1745)(19.11/100)=0.3323

Total Severity=0.3323(100)(16.52/100)(3,000)=16,469

Accordingly, the total severity for the arm, excluding the arm treatment, is 16,469. The arm's treatment severity is added to this, making the arm's total severity 17,469.

As noted above, the engine rolls severities up to composites according to the composite's hierarchy. That is, if a first composite is itself a component of a second composite, the engine determines the severity for the first composite before the second. For example, referring to the arm, wrist and hand, and hand composites illustrated above, assume that in addition to the injuries, treatments and complications provided in the example, the left thumb and left index finger had also been injured. The model, at 224, rolls the component severities into the composite severity for the left hand, calculating a total severity for the left hand. The model then revises the coordinates for the left hand at 228 as described below. These coordinates replace the 6, 7 and −3 coordinates for the left hand in the left wrist and hand composite. The model then rolls the left wrist and left hand severities into the left wrist and hand composite, using the coordinates and severity for the left hand determined in the prior step. At 228, the model determines new coordinates for the left wrist and hand composite that replace the 5.5, 7 and −3 coordinates for the left wrist and hand as a component in the arm composite. Returning to step 224, the model determines the total severity for the arm composite, using the previously calculated left wrist and hand severity and the revised left wrist and hand coordinates. This process continues until severities have been determined for all composites, except for the Whole Body composite.

c. Recalculate Composite Coordinates

Referring now to step 228 and the example above regarding the injuries, treatments and complications to the left arm, left elbow and left forearm, the engine recalculates the arm's coordinates based on a combination of individual body part vectors, where the vectors are defined by the body part coordinates and severities. Continuing the example, the body parts within the arm composite have the following coordinates and severities:

| Body Part | X | Y | Z | Severity/3,000 |
|---|---|---|---|---|
| left arm | 3 | 9 | −3 | 0.0333 |
| left shoulder | 1 | 7 | −3 | 0 |
| left upper arm | 2 | 7 | −3 | 0 |

-continued

| Body Part | X | Y | Z | Severity/3,000 |
|---|---|---|---|---|
| left elbow | 3 | 7 | −3 | 3.911 |
| left forearm | 4 | 7 | −3 | 4.318 |
| left wrist and hand | 5.5 | 7 | −3 | 0 |
| | | | | 8.262 |

Again, the 1,000 severity for the left arm treatment is not considered since it is not properly allocated to the component to which it applies.

Determining the percentage of the total severity contributed by each body part, the arm, left elbow and left forearm contribute, in decimal format, 0.004, 0.523 and 0.473, respectively, of the whole. Each body part's contribution to the total severity is projected onto its position vector as defined by its coordinates. That is, the X, Y and Z components for each body part are multiplied by the body part's severity contribution, resulting in the weighted body part coordinates below:

| Body Part | X | Y | Z | Severity Contribution |
|---|---|---|---|---|
| left arm | 0.012 | 0.036 | −0.012 | 0.004 |
| left shoulder | 0 | 0 | 0 | 0 |
| left upper arm | 0 | 0 | 0 | 0 |
| left elbow | 1.419 | 3.311 | −1.419 | 0.473 |
| left forearm | 2.092 | 3.661 | −1.569 | 0.523 |
| left wrist and hand | 0 | 0 | 0 | 0 |

The weighted coordinates can be considered vectors representing the contribution of each body part to the total severity. The sum of these vectors produces the revised coordinates for the arm, as set forth below.

X: 0.012+1.419+2.092=3.523

Y: 0.036+3.311+3.661=7.008

Z: −0.012−1.419−1.569=−3.000

Thus, in subsequent combinations in which the arm is a component, the arm coordinates are 3.523, 7.008 and −3.000.

d. Derive Whole Body Pain and Suffering Severity

At the conclusion of step 228, the engine has combined composite body part severities up to the level immediately below the final combination to the Whole Body composite level. If there are any medical conditions applicable at the Whole Body level (at present, only ICD9 code 958.4 for traumatic shock is associated with the Whole Body), those medical conditions are combined for the Whole Body as for any other body part, as described above. The engine then, at 232, combines the severity for the whole body with the severities for its components using a gravity algorithm similar to that described above with respect to step 224.

To continue the example, assume the left elbow, left forearm and arm medical conditions described above, resulting in a left arm severity of 17,469, and also assume a right femur injury and treatment that result in a right leg severity of 19,000 and coordinates of 1, 0, 3. Thus, at the level immediately below whole body, there are two components that have severities, the left arm and the right leg:

| Body Part | X | X | Z | Severity/3,000 |
|---|---|---|---|---|
| whole body | | | | 0 |
| spine | 3 | 6 | 0 | 0 |
| right leg | 1 | 0 | 3 | 6.333 |
| left leg | 3 | 2 | −3 | 0 |
| right arm | 3 | 9 | 3 | 0 |
| left arm | 3.523 | 7.008 | −3 | 5.823 |
| trunk | −2 | 3 | 0 | 0 |
| head | 0 | 14 | 0 | 0 |
| brain | 0 | 15 | 0 | 0 |

The gravity algorithm executed at 232 is the same as that executed at 224 for the lower-level composites, except for the distance calculation. If both the left arm and right arm, or both the left leg and right leg, have severities, the distance between the left arm and right arm, or between the left leg and right leg, is calculated as follows:

$$\text{Distance}(j,k) = (X(j)^2 + Y(j)^2 + Z(j)^2)^{0.5} + (X(k)^2 + Y(k)^2 + Z(k)^2)^{0.5}$$

The distance between any other component pair combination is:

$$\text{Distance}(j,k) = ((X(j) - X(k))^2 + (Y(j) - Y(k))^2 + (Z(j) - Z(h))^2)^{0.5}$$

The distance formula for the dual leg and dual arm combinations results in a greater severity for those injury combinations. That is, the increased distance reflects the relatively greater severity impact of those particular combinations.

The calculations for the whole body severity, given the above example, are as follows:

$\text{valuelist}(L) = 6.333$ $\text{valuelist}(A) = 5.823$ $\text{Loc Abs Mass}(L) = (100 - 6.333)/100 = 0.9367$ $\text{Loc Abs Mass}(A) = (100 - 5.823)/100 = 0.9418$ $\text{Mass Diff}(L,A) = \min(6.333, 5.823)/\max(6.333, 5.823) = 0.9195$ $\text{Distance}(L,A) = (6.366 + 49.112 + 36)^{0.5} = 9.564$ $\text{Distance Effect}(L,A) = (1/\max(9.564 + 5, 2)^1 = 1/14.564 = 0.06866$ $\text{Impact}(L,A) = (1 - 0.9195 * 0.9367 * 0.06866)^2 = 0.8853$ $\text{Impact}(A,L) = (1 - 0.9195 * 0.9418 * 0.06866)^2 = 0.8846$ $\text{Loc New Mass}(L) = 6.333(1 - ((1 - 0.8853)/1) = 5.607$ $\text{Loc New Mass}(A) = 5.823(1 - ((1 - 0.8846)/1) = 5.151$ $\text{Bound} = 2(6.333 + 5.823) = 24.312$ $\text{New Mass}(L) = 5.607 * 100/24.312 = 23.063$ $\text{New Mass}(A) = 5.151 * 100/24.312 = 21.187$ $x(n) = 0 + (1 - 0)0.23063 + (1 - 0.23063)0.21187 = 0.3936$ Total severity = 39.36(24.312/100)3,000 = 28,708

Thus, the total severity for the whole body is 28,708.

e. Whiplash

The engine applies additional processing to whiplash severities before they are applied in the body part severity combination and the composite severity buildup described above. The following ICD9 codes correspond to non-demonstrable whiplash injuries:

| Body Part | Whiplash Codes |
|---|---|
| Sacral area | 846.0, 846.1, 846.2, 846.3, 846.8, 846.9, 847.3, 847.4 |
| Lumbar Spine | 847.2 |
| Cervical Spine | 847.0 |
| Thoracic Spine | 847.1 |

The thoracic spine, cervical spine, lumbar spine and sacral area are components of the soft tissue spine composite. The spine, a separate composite, has the same components. Thus, ICD9 codes that relate to demonstrable injuries may be applied to the spine body parts, while codes relating to whiplash injuries are applied to the soft tissue spine body parts. Unlike the profiles for demonstrable injuries, the engine does not stretch the profile residual dates for whiplash profiles for differences between the original residual date and assumed stabilization days. Prognoses, however, apply to whiplash profiles as for any other profile. The whiplash profiles and their severities are combined up to the soft tissue spine composite body part severities in the same manner as discussed above with respect to steps 224 and 228, except for the distance calculation. Prior to combining the severities for the body parts, however, the engine derives the whiplash severities according to the procedure discussed below.

Whiplash is a common complaint among claimants involved in automobile accidents. Unfortunately, such injuries are difficult to diagnose, and the engine therefore adjusts whiplash severities according to the external factors that tend to indicate the existence or absence of the injury. These factors include the existence of other injuries, the length of treatment, the type of treating practitioner, the number of visits to treating practitioners and delay in seeking treatment.

Figure 19:
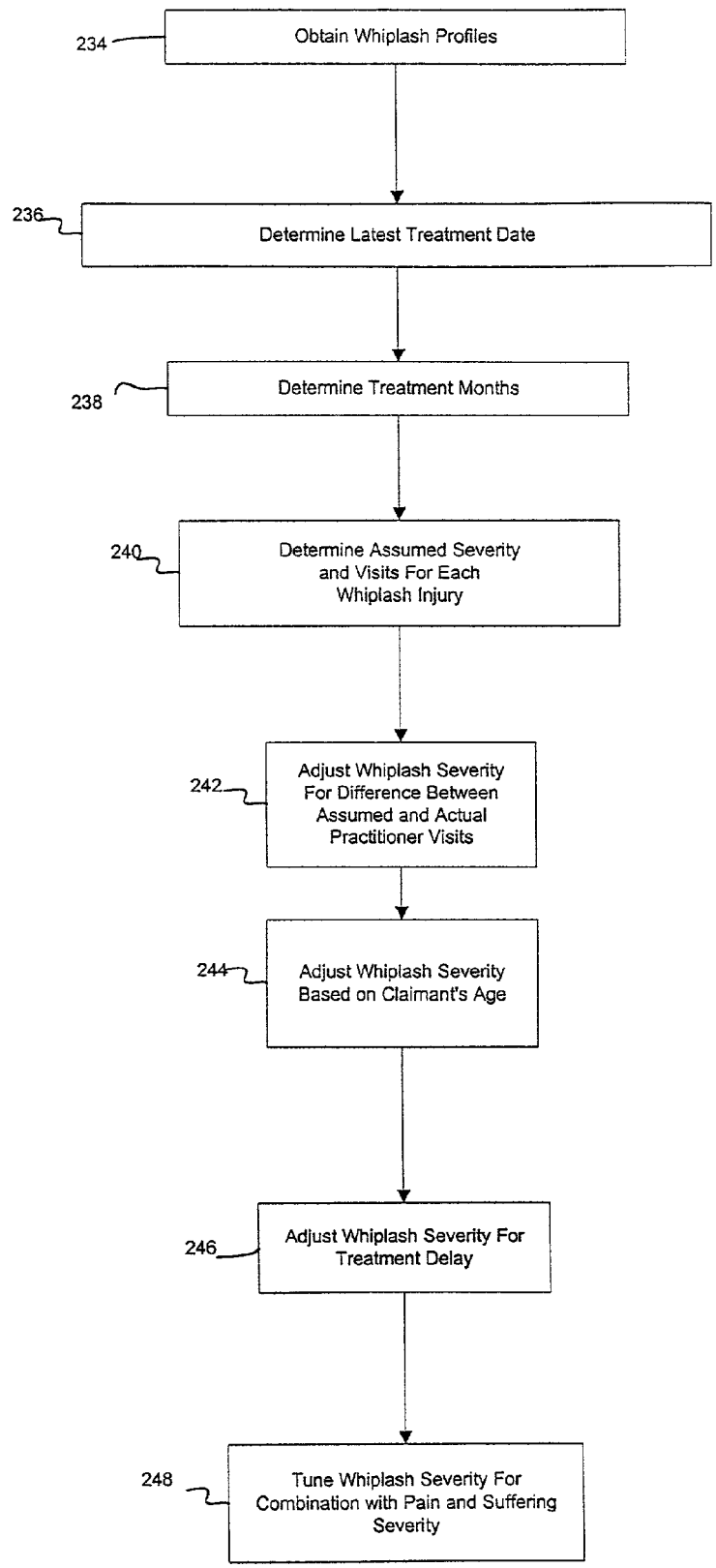
FIG. 19 is a flow chart illustrating the whiplash severity portion of the whole body pain and suffering step of FIG. 17.

FIG. 19 illustrates the whiplash procedure. At 234, the engine obtains the whiplash profiles and adjusts the profiles for prognoses and profile adjustment rules. It then determines the treatment time, an indicator of the period in which the claimant received treatment for whiplash. This period is positively related to the likelihood that the whiplash injury exists.

The model includes two methods of indicating treatment for whiplash injuries. First, the user may indicate physiotherapy, chiropractic and/or osteopath treatments that relate to whiplash by entering the appropriate ICD9 codes in the medical details input data (FIG. 1). That is, the user enters the code for the type of treatment received, along with the period over which such treatments were received and the number of visits provided during the period. Each code is tied to the type of practitioner, whether physiotherapist, chiropractor or osteopath. Second, medical prognoses applied to the affected body parts indicate that the claimant has been examined by the medical practitioner that issued the prognosis. Accordingly, the engine looks both to treatment codes and prognoses to determine the period over which the claimant received treatments for the whiplash injuries.

At 236, the engine finds the last treatment date associated with the treatment codes and determines the difference between that date and the whiplash injury date. For example, assuming that the claimant received physiotherapy treatments over the periods from February 5 through February 10, with five visits, February 20 through February 28, with four visits and April 4 through April 9, with four visits, the latest treatment date is April 9. Assume that there are no other whiplash-related treatment codes. If the whiplash injury occurs on January 1, the difference between April 9 and January 1 is 99 days.

At 238, the engine determines the treatment period based on the recovery prognoses. First, the engine compares the effective date of the latest prognosis to the latest treatment date, April 9 in the above example. If the latest prognosis is a non-MMI prognosis, and if the prognosis date is later than the latest treatment date, the prognosis date becomes the "latest treatment" date. If the latest prognosis effective date is prior to the latest treatment date, or if the latest prognosis is an MMI prognosis, the latest treatment date is not changed. An MMI prognosis is any of the group of prognoses that indicate that maximum medical improvement has been achieved. For these prognoses, the date at which treatment for the injury ended occurred sometime in the past and is, therefore, not reflected by the prognosis date. Accordingly, the engine does not replace the latest treatment date. If, however, the latest recovery prognosis is one that indicates maximum medical improvement has not occurred, the prognosis date is an indication that treatment is continuing at least as of that date. Thus, the prognosis date is compared to the latest treatment code date to determine the treatment period. For example, if the latest treatment code date is April 9 as above, and a single non-MMI recovery prognosis was provided on April 28, the treatment period extends from January 1 to April 28, or 118 days.

If there are multiple recovery prognoses, the engine may also adjust the latest treatment date based on a combination of the predicted recovery dates for all prognoses. The combination proceeds according to several rules. First, the engine considers only the latest prognosis provided by any given medical practitioner. If, after this elimination, there are still multiple recovery prognoses, the engine determines the stabilization date predicted by each prognosis. For each non-MMI prognosis, the stabilization date is determined as follows:

"Heal in Months"

Stab. Date=Prognosis Date+#months–start date+1.

"Healing Satisfactorily"

Stab. Date=Max(7+Prognosis Period, 1.11* Prognosis Period)

"Healing Slowly"

Stab. Date=Max(14+Prognosis Period, 1.33* Prognosis Period)

"Will Heal in Weeks"

Stab. Date=14+Prognosis Period

"Will Heal Eventually"

Stab. Date=Min(182+Prognosis Period, 2* Prognosis Period)

For all other recovery Prognoses:

Stab. Date=MMI Date–Case Start Date+1, where the MMI date for most prognoses is the prognosis date.

Once the stabilization dates have been determined, the routine ignores those prognoses having a stabilization date before the latest treatment date. The routine assumes that the later treatment accounts for those prognoses. The remaining stabilization dates are weighted based on the order of their effective dates and on the medical practitioner that provided the prognosis. First, each stabilization date is assigned a weight equal to the ratio of its prognosis effective date to the latest prognosis date. Thus, the weights are between 0 and 1, where the latest stabilization date has a weight of 1. If, however, any of the earlier prognoses is marked as preferred, it is assigned a weight of 1. The time weights reflect that the later prognoses are considered more accurate.

A second weighting reflects relative confidence among medical practitioners as defined by the user. A weight is defined for each type of practitioner. For example, a user may have a 30° s confidence level in a prognosis provided by a chiropractor as compared to that provided by a treating specialist. Accordingly, assuming that the treating specialist receives the highest confidence level, the treating specialist factor is 1, and the chiropractor's weighting factor is 0.3.

The routine applies the weighting factors against the predicted stabilization dates, sums the results and divides by the sum of the weights to determine the treatment period resulting from the multiple prognoses.

For example, assume that a treating specialist provided a "will heal eventually" prognosis on March 15 and that a chiropractor provided a "will heal in 3 months" prognosis on April 28. The predicted stabilization period for the treating specialist's prognosis is Min(182+74, 2(74))=Min(256, 148) =148. The predicted stabilization period for the chiropractor's prognosis is ((April 28-January 1)+90)–start date+ 1=118+90–January 1+1=208.

Assume also the physiotherapist treatments described in the example above. The latest treatment has an effective date of April 9, but the latest treatment date was changed to 118 due to a final non-MMI recovery prognosis. Since January 1+148 and January 1+208 are both beyond April 28, 118 days after the case start date, both prognoses are considered in the weighted combination.

The chiropractor's prognosis is later than that of the treating specialist, and its time weight is, therefore, 1. The treating specialist's prognosis is not marked as preferred. It was provided on March 15. The period of March 15-January 1, divided by the period of April 28-January 1, is 0.6271. Thus, the time weights for the chiropractor prognosis and the specialist prognosis are 1 and 0.6271, respectively.

Assuming that the chiropractor's practitioner weighting factor is 0.3, the final weighting for the chiropractor prognosis is 1(0.3)=0.3. If the practitioner weighting for treating specialists is 1, the final weighting for the treating specialist's prognosis is 1(0.6271)=0.6271. The treatment period is determined as follows:

$$(0.6271 * 148 + 0.30 * 208) / (0.6271 + 0.3) =$$

$$(92.81 + 62.4) / 0.9271 = 167.41$$

Accordingly, the treatment period resulting from the multiple prognoses is 167.41 days, or 5.4 months. Since 167.41 days is greater than 118, the latest treatment date is changed to 167.41.

Referring again to FIG. 19, the model determines at 240 an assumed severity, assumed number of specialist visits, assumed number of general practitioner visits and assumed number of physiotherapist visits for each whiplash injury, based on the following table:

| Treatment Months | Spec. Visits | GP Visits | Phys. Visits | Severity |
| --- | --- | --- | --- | --- |
| 0 | 0 | 0 | 0 | 0 |
| 3 | 0 | 3 | 5 | 2,000 |
| 6 | 0 | 4 | 8 | 4,500 |
| 12 | 2 | 7 | 15 | 10,000 |
| 18 | 3 | 9 | 20 | 15,000 |
| 24 | 4 | 12 | 25 | 16,000 |
| 36 | 6 | 12 | 30 | 17,000 |
| 999 | 6 | 12 | 30 | 18,000 |

In another preferred embodiment, the severities in column 5 corresponding to 6, 12 and 18 treatment months in column 1 are 5,000, 9,000 and 13,000, respectively.

Referring again to the example, the treatment months is 5.4. The specialist visits, general practitioner visits, physiotherapist visits and severity value are determined using a linear interpolation between the values given in the above table between 3 months and 6 months. Solving for the assumed severity:

$$\text{Severity} = (5.4 - 3)(4{,}500 - 2{,}000) / (6 - 3) + 2{,}000 = 4{,}000.$$

Using a similar interpolation, the assumed specialist visits is 0, the assumed general practitioner visits is 3.8, and the assumed physiotherapy visits is 7.4.

At 242, the model adjusts the assumed severity for differences between the actual and assumed number of practitioner visits. For example, assume that the claimant made three specialist visits, three general practitioner visits and fourteen physiotherapist visits. Chiropractor and osteopath visits may be incorporated into general practitioner visits or physiotherapist visits. The user, via switches in the database, indicates whether osteopaths and chiropractors are to be considered general practitioners. If the switches are set to "yes", the number of general practitioner visits equals the actual general practitioner visits, plus one-half the number of osteopath visits rounded to the nearest whole number, plus one-half the number of chiropractor visits rounded to the nearest whole number. If the switches are set to "no", the whole number of osteopath visits and chiropractor visits are included as physiotherapist visits.

As indicated above, chiropractic, physiotherapy and osteopath visits may be reflected both by treatment codes tied to those practitioners and by recovery prognoses for which visits are entered. Because these numbers may be redundant, the model considers the number of visits from each source during the prognosis period and chooses the greater. If the recovery is an MMI recovery, the model reduces the number of visits entered with the recovery by one, since the last visit concerned the MMI opinion rather than a treatment. General practitioner and specialist visits are entered through prognosis.

The engine adjusts the assumed severity based on the following tables:

| Specialist Visits | Severity |
| --- | --- |
| 0 | 0 |
| 1 | 500 |
| 2 | 1,000 |
| 3 | 1,500 |
| 4 | 2,000 |
| 5 | 2,500 |
| 10 | 4,000 |
| 999 | 10,000 |

| GP Visits | Severity |
| --- | --- |
| 0 | 0 |
| 3 | 300 |
| 4 | 400 |
| 7 | 700 |
| 9 | 900 |
| 12 | 1,200 |
| 20 | 2,000 |
| 999 | 5,000 |

| Phys. Visits | Severity |
| --- | --- |
| 0 | 0 |
| 5 | 350 |
| 8 | 500 |
| 15 | 750 |
| 20 | 1,000 |
| 25 | 1,200 |
| 30 | 1,300 |
| 50 | 1,500 |
| 999 | 5,000 |

Turning first to the specialist adjustment, the model determines the difference between the actual specialist visits, 3 in the above example, and the assumed specialist visits, 0. A difference less than −2 indicates a lack of treatment, and a more severe adjustment is made as discussed below. In this case, the difference, 3, is greater than −2, and the severity adjustment is determined according to the table above. Referring to the table, the severity for 3 visits is 1,500. The severity for 0 visits is 0. The difference between these severities is 1,500, and the assumed severity of 4,000 is therefore increased to 5,500.

If the difference between the actual and assumed visits is between 0 and −2, the model still determines the difference between the severity for the actual visits and the assumed visits, but multiplies by a reduction factor that may be set by the user prior to adjusting the original assumed severity. The factor defaults to 1000. For example, if the difference between the actual severity and assumed severity was −1,000, and the reduction factor is 0.5, the assumed severity of 4,000 would be reduced by 500.

The difference between the actual and assumed general practitioner visits is −0.8. If the difference had been less than −5, the model would have adjusted the severity according to the rules discussed below regarding lack of treatment. Since the difference is equal to or greater than −5, the adjustment is made according to the above table for general practitioner visits. Referring to the table, the severity for the actual number of visits, 3, is 300. The severity for the assumed number of visits, 3.8, falls between 300 and 400. Using a linear interpolation, the severity for 3.8 visits is 380. The difference between the severity for the actual visits, 300, and the severity for the assumed visits, 380, is −80. Since this results in a severity reduction, the adjustment value is multiplied by the whiplash reduction factor discussed above regarding specialist visits. Assuming that the reduction factor is 100%, the severity adjustment remains −80, changing the whiplash severity from 5,500 to 5,420.

The difference between the actual and assumed physiotherapist visits is 6.6. Had this difference been less than −15, the model would have adjusted the severity according to the rules described below regarding lack of treatment. Referring to the physiotherapist table above, the severity for 14 visits is between 500 and 750. Using a linear interpolation, the severity is 714.29. Similarly, the severity for 7.4 visits is 470. The difference between the actual visit severity and the assumed visit severity is 244.29, increasing the severity of 5,420 to 5,664.29.

Referring again to FIG. 19, the model adjusts the severity for the claimant's age at 244 according to the following table:

| Age | Adjustment Factor |
|---|---|
| 0 | 0.5 |
| 3 | 0.5 |
| 15 | 1.0 |
| 200 | 1.0 |

For example, if the claimant is 3 years old, and the whiplash severity is 5,664.29, the severity is multiplied by a factor of 0.5, resulting in a severity of 2,832.15.

The engine reduces the calculated whiplash severity at 246 if conditions exist indicating that the claimant has delayed seeking treatment for the whiplash or has had insufficient treatment. In the former case, a treatment delay may indicate that the claimant sought treatment later in an effort to drive up the value of general damages. In the latter, fewer practitioner visits than would normally be expected may indicate that the whiplash injury does not exist.

To determine treatment delay, the engine examines the time between the injury date and the first treatment date. As described above, treatments may be reflected through treatment ICD9 codes or through recovery prognoses that indicate the number of visits to a medical practitioner. If, however, there is a recovery prognosis with multiple visits, the model cannot determine when the first visit occurred and therefore makes no adjustment for treatment delay. If there are no recovery prognoses with multiple visits, the delay period is the time between the injury start date and the effective date of the first single-visit recovery prognosis or whiplash treatment.

If the period between the injury start date and the first of these dates is beyond a predefined grace period, the engine determines a severity reduction factor as discussed below. If the first of these dates is beyond the grace period, and if there are any recovery prognoses having multiple visits, the engine prompts the user to examine the number of visits applicable to the recovery prognosis to determine whether a delay has occurred, but does not execute a reduction factor.

The grace period is the minimum of (1) 30 days and (2) the maximum of 3 days and 30X/15,000, where X is the sum of the severities for demonstrable injuries, treatments and complications assigned for all body parts. Thus, the existence of other, demonstrable injuries prolongs the grace period and, therefore, reduces the probability that the whiplash severity will be reduced.

The reduction factor is a percentage multiplied against the calculated whiplash severity. The engine determines the reduction factor for a given case by linear interpolation using the table below. The table is user-defined; thus, the table values below are provided for purposes of explanation.

| Delay (days) | Reduction Factor |
|---|---|
| 0 | 1.00 |
| 10 | 0.75 |
| 50 | 0.10 |

The delay column refers to the number of days between the end of the grace period and the end of the treatment delay period. For example, assume that the whiplash injury date is January 1, that the earliest treatment date is January 8, and that the grace period is 3 days. The period between the injury start date and the first treatment date is greater than the grace period. The delay period is the difference between 7 days and 3 days, or 4 days. Using a linear interpolation, the reduction factor calculated from the table above is 0.90. Assuming that the calculated whiplash severity for this body part is 6,064.29 and that the claimant is 3 years old, the final severity is.

$$6,064.29(0.50)(0.90)=2,728.94.$$

The reduction factor for insufficient medical practitioner visits is derived from the following tables:

| Specialist Visits | Specialist Contribution |
|---|---|
| 0 | 0 |
| 1 | 5 |
| 2 | 10 |
| 3 | 20 |
| 4 | 30 |
| 5 | 40 |
| 10 | 90 |
| 999 | 99 |

| GP Visits | GP Contribution |
|---|---|
| 0 | 0 |
| 3 | 10 |
| 4 | 15 |
| 7 | 20 |
| 9 | 30 |
| 12 | 40 |
| 20 | 60 |
| 999 | 99 |

| Phys. Visits | Phys. Contribution |
|---|---|
| 0 | 0 |
| 5 | 5 |
| 8 | 10 |
| 15 | 20 |
| 20 | 30 |
| 25 | 40 |
| 30 | 50 |

-continued

| | |
|---|---|
| 50 | 80 |
| 999 | 99 |

For each table, the left hand column refers to the difference between the actual and assumed number of visits. The contribution in a given case is determined through a linear interpolation, and the engine combines the contribution from each practitioner type through a gravity algorithm to determine the severity reduction.

For example, assume that for a given case, the assumed specialist, general practitioner and physiotherapist visits are 2, 7 and 15, respectively. Assume also that the respective actual number of visits are 0, 1 and 0. Regarding the specialist visits, the difference between assumed and actual is −2, which is less than or equal to the threshold amount required to call for a reduction factor. The absolute value of the difference is 2. Referring to the specialist table above, the specialist contribution is 10.

The model includes a factor that can be set by the user to scale the contribution for each medical practitioner type. The factor may be used in countries in which adjusters do not have access to treatment information. Where treatment information is not provided, even if it actually occurred, the model could reduce whiplash severity even though there had been no lack of treatment. In such jurisdictions, this factor can be set to a value between 0 and 1 that is multiplied against the contribution number. If this factor is set to 0, the contribution numbers are eliminated, and the model does not reduce the severity for lack of treatment. The default value for this parameter is 1.

Regarding general practitioner visits, the difference between assumed visits and actual visits is −6, which is beyond the threshold. Using a linear interpolation for the absolute value, 6, the GP contribution is 18.33.

Regarding physiotherapist visits, the difference between actual and assumed visits is −15, which is equal to or less than the threshold. The absolute value of the difference is 15. Referring to the table, the physiotherapist contribution corresponding to 15 visits is 20.

The engine applies a gravity algorithm to combine the contribution for specialists (S), general practitioners (GP) and physiotherapists (P) as set forth below. The "distance" value between 2 entities is the absolute value of the difference between the locations for those entities.

| | |
|---|---|
| valuelist (S) = 10 | location (S) = 1 |
| valuelist (GP) = 18.33 | location (GP) = 1 |
| valuelist (P) = 20 | location (P) = 1 | k,g=1 d=2

Loc Abs Mass($S$)=(100−10)/100=0.90

Loc Abs Mass($GP$)=(100−18.33)/100=0.8167

Loc Abs Mass($P$)=(100−20)/100=0.80

Mass Diff($S,GP$)=min(10,18.33)/max(10,18.33)
=0.5456

Mass Diff($S,P$)=min(10,20)/max(10,20)=0.500

Mass Diff($GP,P$)=min(18.33,0)/max(18.33,20)=0.9165

Distance($S,GP$)=(1−1)=0

Distance($S,P$)=(1−1)=0

Distance($GP,P$)=(1−1)=0

Distance Effect($S,GP$)=(1/max(0+1,2))$^2$=0.25

Distance Effect($S,P$)=(1/max(0+1,2))$^2$=0.25

Distance Effect($GP,P$)=(1/max(0+1,2))$^2$=0.25

Impact($S,GP$)=(1−0.5456*0.90*0.25)$^2$=0.7696

Impact($S,P$)=(1−0.5000*0.90*0.25)$^2$=0.7877

Impact($GP,S$)=(1−0.5456*0.8167*0.25)$^2$=0.7896

Impact($GP,P$)=(1−0.9165*0.8167*0.25)$^2$=0.6608

Impact($P,S$)=(1−0.5000*0.80*0.25)$^2$=0.8100

Impact($P,GP$)=(1−0.9165*0.80*0.25)$^2$=0.6670

New Mass($S$)=Loc New Mass($S$,2)=10(1−(1−0.7696)/1)(1−(1−0.7877)/2)=6.8791

New Mass($GP$)=Loc New Mass($GP$,2)=18.33(1−(1−0.6608)/1)(1−(1−0.7896)/2)=10.838

New Mass($P$)=Loc New Mass($P$,2)=20(1−(1−0.6670)/1)(1−(1−0.8100)/2)=12.073

Reduction/100=0+(1−0)(6.8791/100)+(1−0.068791)(10.838/100)

Reduction=26.99

Thus, the reduction resulting from the combination of medical practitioner visit reductions is 26.990. If the original calculated severity for whiplash for this body part is 10,000, the reduction by 26.99% leaves a severity of 7,301.

The above routines derive and modify whiplash severities for each body part. In addition, referring again to FIG. 19, the user may discount whiplash severity at 248, before it is rolled into whole body pain and suffering severity, by a tuning variable multiplied against the calculated severity. In one embodiment, the default is 0.8, although the user may set the variable through the Tuning Wizard (FIG. 1) to any value between 0 and 1. Assuming that the variable is 0.8, the calculated severity of 7,301 above becomes 5,841.

If a claimant has multiple whiplash injuries, their severities are combined using the gravity routines as described above for non-whiplash injuries, except for the distance and distance effect equations in three-dimensional gravity. Specifically, Distance($j,k$)=(($X_j−X_k$)2+($Y_j−Y_k$)$^2$+($Z_j−Z_k$)$^2$)$^{0.5}$ where $X_j$, $Y_j$, $Z_j$ and $X_k$, $Y_k$, $Z_k$ are the coordinates for body parts j and k. The engine determines a "denominator" value by linear interpolation of the distance value calculated above against the following table:

| Distance | Denominator |
|---|---|
| 0 | 3.7 |
| 2 | 3.7 |

-continued

| Distance | Denominator |
|---|---|
| 5 | 4.5 |
| 9 | 8.0 |
| 50 | 15.0 |

For example, where the calculated distance value is 1, the denominator value is 3.7. Distance effect is:

Distance Effect$(j,k)$=1/Denominator$(j,k)$.

Finally, if a radiculitis complication (ICD9 codes 724.4.br, 724.4.bl, 724.4.ar, 724.4.al, 734.4.r and 734.4.1) applies to the sacral area, lumbar spine or cervical spine soft tissue body parts, where there is no demonstrable injury applied to that body part, the number of profile days for the radiculitis complication is reduced by 25%.

2. Determine Hospital/Convalescent Care Severity

Referring again to FIG. 17, the engine determines at 250 a severity value at 250 relating to the period of time a claimant spent in a hospital and/or received convalescent care. The user enters start and end dates for hospital stays and convalescent periods associated with injuries, treatments and complications. The time periods these dates reflect are used against the following table to determine a severity to assign for hospital stays and convalescent care periods:

| Days | Severity |
|---|---|
| 1 | 250 |
| 2 | 500 |
| 6 | 750 |
| 10 | 1,000 |
| 30 | 5,000 |
| 365 | 10,000 |
| 3,650 | 20,000 |

The same table is used both for hospital stays and convalescent care. Convalescent care is considered to be less traumatic than hospital stays. Thus convalescent care severities calculated from the table are multiplied by a factor of 0.7. Furthermore, the table covers up to a 10 year period, and the engine will calculate a severity based on an actual number of days, up to 10 years. The user has the option, however, to enter "permanent" for either hospital stay or convalescent care. For "permanent" hospital stays or convalescent care periods, the engine calculates the severity from the table based on 90 days. The engine assumes that other methods of compensating the claimant, for example loss of amenities as discussed below, will be used to compensate the claimant for the extended hospital stay or convalescent care period.

As an example, assume that the claimant entered the hospital on January 1 and was discharged on January 14. The overall period, 14 days, is reduced by 1 to account for a 1 day assumption for admittance and discharge time, leaving a hospital stay period of 13 days. Using a linear interpolation, the severity assigned by the table above for 13 days is 1,600.

In one embodiment, the model does not allow overlapping hospital and convalescent periods. Thus, continuing the example, assume that on January 15, the claimant begins receiving permanent convalescent care. By linear interpolation, the severity for 90 days assigned by the above table is 5,895.52. Applying the 70% multiplier, the convalescent severity is 4,126.87. Adding the 1,600 hospital severity, the total hospital and convalescent severity is 5,726.87.

In the above-described embodiment, the engine does not accept overlapping hospital stays. Thus, if there are multiple injuries that require hospitalization, the user enters the actual number of days spent by the claimant in the hospital. The same rule applies to convalescent care.

The model now adjusts the hospital/convalescent severity to back out the assumed severity already present in the injury, treatment and complication severities determined above for pain and suffering. That is, the assumed severity associated with each injury, treatment and complication ICD9 code includes a consideration for any hospital stay that would normally be expected for that medical condition. The assumption for each medical condition is reflected by the assumed number of hospital days associated with each ICD9 code. For one presently preferred embodiment, the assumed hospital days are found in column 9 of the file Medical Attributes.zip in the electronic appendices.

To determine the assumed hospital time, the model determines the assumed hospital stay for each ICD9 code entered for the case, beginning at the effective date for each code. Again, overlapping days are counted only once. Thus, the model determines the total number of days the claimant would be assumed to spend in the hospital if each medical condition had occurred on its assigned effective date.

As an example, assume that five ICD9 codes have been assigned to the case and that these medical conditions result in the hospital/convalescent care severity in the example above. The medical conditions have the same effective dates and have respective assumed hospital days of 3, 4, 5, 15 and 12. Since their effective dates are the same, they all overlap, and the assumed hospital days is the maximum, 15. Applying the linear interpolation algorithm to the hospital/convalescent care severity table above, the severity for the assumed number of hospital days is 2,000. Subtracting from the 5,726.87 severity determined above, the hospital/convalescent care severity determined at 250 is 3,727.87.

3. Determine Future Treatment/Complication Severity

The model also considers, at 252, preferred prognoses indicating that the claimant may have to endure future treatments and complications as a result of present medical conditions. As with present medical conditions, future treatments and complications are defined by reference to ICD9 codes. That is, if a medical practitioner provides a prognosis that includes a future treatment or complication, the user enters the ICD9 code corresponding to the treatment or complication. The code is entered, however, as part of the prognosis information rather than the medical details information (FIG. 1). Since there may be multiple medical practitioners, the model considers only a future treatment/complication prognosis that is marked as "preferred." To avoid consideration of redundant prognoses, only one such prognosis may be preferred, although multiple future treatments and complications may be entered on the preferred prognosis.

The user enters a probability ("definite," "probable" or "possible") that reflects the likelihood that the treatment or complication will occur. These probabilities are, in turn, associated with multipliers (definite=1.00, probable=0.60 and possible=0.25) that are multiplied against the severities assigned to the ICD9 codes for the treatments and complications. For example, assume that a future treatment/complication prognosis includes a probable bone graft (78.05.r), a possible stim insertion (78.95.r) and a possible osteomyelitis (730.05.ar). The assumed severity for the bone graft is 2,500. Its probability is "probable." The severity associated with the future treatment is, therefore, 1,500. The assumed severities for the stim insertion and the osteomyelitis are 1,000 and 8,000, respectively. Each has a "possible" probability, and the respective severities therefore become 250 and 2,000. Thus the total severity attributable to future treatments/complications is 3,750.

At 264 (FIG. 17), the engine sums (1) whole body pain and suffering severity, (2) hospital/convalescent care severity and (3) future treatment/complication severity.

4. Determine Post Traumatic Stress Syndrome Severity

At 254, the engine determines a severity for post traumatic stress disorder (PTSD) diagnoses in a manner similar to the processing for whiplash diagnoses described above. The engine determines the total time period during which the claimant received treatment for the PTSD and the period between the diagnosis and the point at which the claimant recovers or is predicted to recover. It then determines an assumed severity, taking into consideration these time periods, and adjusts the assumed severity based on any difference between the actual treatment period and an assumed treatment period. Like whiplash, PTSD is a non-demonstrable injury.

Its ICD9 code (308.3.a) is directed to the PTSD body part, which is a component of the composite body part "psyche." Although the PTSD body part does have a dysfunction-v-time profile, it is not included as a body part in the conjunction records or the loss of amenity function described below and, therefore, does not affect workers' compensation or loss of amenity calculations. It should be understood, however, that the model could be set up to include such considerations.

The user enters the PTSD ICD9 code with other medical details (FIG. 1) applicable for the claimant. Upon entering the PTSD code, a sub-panel is available to the user to enter the symptoms that may be exhibited by the claimant to indicate the PTSD condition. These include gastrointestinal disorders, flashbacks, eneuresis, nightmares, insomnia, heart palpitations, excessive sweating, panic attacks, fear of travel, reactive depression, aggressive outbursts, social withdrawal, general fatigue and psychogenic amnesia.

To determine a PTSD severity in the present embodiment, the user must enter evidence that the claimant has received treatment for the disorder. As with whiplash, treatment may be indicated by treatment ICD9 codes or by recovery prognoses. The prognoses are, generally, the same as described above. Treatment ICD9 codes applicable to PTSD are as follows:

| ICD9 Code | Description |
| --- | --- |
| 94.25.(a,b, . . . ,g) | drug therapy for a period of time indicated by suffix (a,b, . . . ,g), where (b,c, . . . ,g) represent incrementing number of weeks and where a represents unknown duration. |
| 94.31.(a,b, . . . ,g) | psychotherapy for period of weeks (b,c, . . . ,g) or unknown duration (a) |
| 94.32.(a,b, . . . ,g) | hypnotherapy for period of weeks (b,c, . . . ,g) or unknown duration (a) |

-continued

| ICD9 Code | Description |
| --- | --- |
| 94.33.(a,b, . . . ,g) | behavior therapy for period of weeks (b,c, . . . ,g) or unknown duration (a) |
| 94.42.(a,b, . . . g) | family therapy for period of weeks (b,c, . . . ,g) or unknown duration (a) |
| 94.44.(a,b, . . . ,g) | group therapy for period of weeks (b,c, . . . ,g) or unknown duration (a) |
| 94.49.(a,b, . . . ,g) | other counseling for period of weeks (b,c, . . . ,g) or unknown duration (a) |

The severity calculation depends on treatment received by the claimant. If the case includes no treatment, either through codes or recovery prognoses, the model adds no severity for PTSD.

Figure 20:
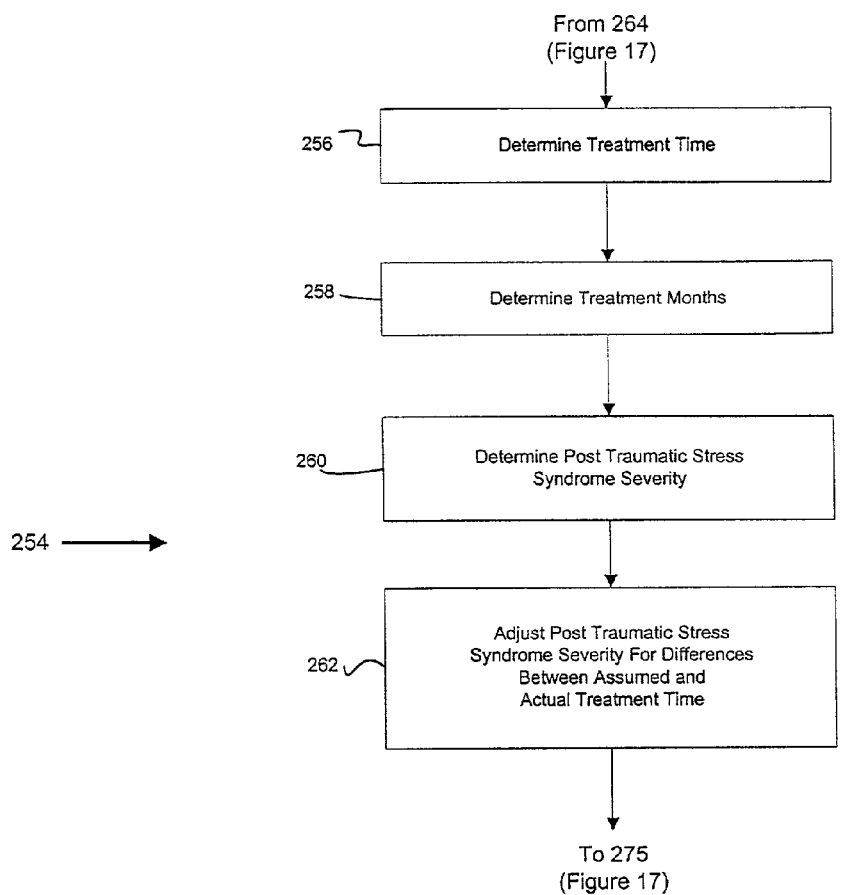
FIG. 20 is a flow chart illustrating the post traumatic stress syndrome severity step of FIG. 17.

The actual time period during which the claimant receives treatment is referred to herein as "treatment time." "Treatment months" is the overall period between the PTSD diagnosis and the point at which the claimant recovers or is predicted to recover. Referring to FIG. 20, the model determines treatment time at 256 by summing the periods covered by any of the treatment ICD9 codes listed above that are entered for the claimant. The engine counts overlapping periods only once.

For example, assume that a claimant with a PTSD diagnosis on May 1 receives drug therapy and psychotherapy treatments as follows:

| Treatment | Period (Days) | Start | End |
| --- | --- | --- | --- |
| 94.25.b | 28 | May 28, 1998 | Jun. 29, 1998 |
| 94.31.b | 28 | May 28, 1998 | Jun. 25, 1998 |
| 94.25.c | 63 | Aug. 1, 1998 | Oct. 3, 1998 |
| 94.31.c | 63 | Aug. 1, 1998 | Oct. 3, 1998 |

Here, the two treatments starting on May 28 overlap, and the two treatments starting on August 1 overlap. The total treatment time is 28+63=91 days, or 13 weeks. For codes ending in "a" (unknown duration), the period is assumed to be 63 days.

At 258, treatment months is the period between the PTSD diagnosis date and the latest treatment code ending date, or the period between the PTSD diagnosis date and the prognosis ending date as described below, whichever is greater.

For the above example, the latest treatment end date is October 3. This is referred to herein as the "maximum treatment date." The PTSD diagnosis date is May 1, resulting in a difference of 156 days.

The engine determines the recovery prognosis ending date through a combination algorithm similar to that described above regarding whiplash prognoses. The engine first determines the latest effective date of the recovery prognoses applicable to PTSD and determines the difference between the PTSD diagnosis date and this date. For example, if the last recovery prognosis for the PTSD condition was provided on November 1, and the condition was diagnosed on May 1, the "latest recovery" value is 185. The engine then determines a weight for each PTSD recovery prognosis equal to the difference between the prognosis effective date and the PTSD diagnosis date, divided by the latest recovery value. Thus, the weight for each recovery prognosis is between 0 and 1, and the weight for the latest recovery prognosis is 1.0. However, if one of the earlier recovery prognoses is marked as preferred, it receives a weight of 1.0 regardless of the calculated ratio. Furthermore, the engine considers only the latest recovery prognosis provided by a given medical practitioner.

As in whiplash processing, the prognosis weights are further manipulated by weighting factors applicable to medical practitioners. For example, the weighting for a treating specialist might be 1.0, whereas the weighting for a chiropractor might be 0.3.

Continuing the example above, assume that a treating specialist provides a "will heal eventually" prognosis on May 15 and that the same treating specialist provides a "will heal in months" prognosis on November 1. The latest recovery prognosis is the "will heal in months" on November 1. Thus, its time weight is 1.0. Since it was provided by a treating specialist, its medical practitioner weighting is also 1.0. The "will heal eventually" recovery prognosis was provided by the same treating specialist and is, therefore, ignored.

Each recovery prognosis has a predicted date of stabilization. These are calculated as described above with respect to whiplash.

Returning to the example, the only remaining recovery prognosis is the November 1 "will heal in months." The PTSD start date is May 1. Assuming that the prognosis predicts MMI in two months and that the case start date is January 1, the predicted stabilization period is:

Prognosis date+months−PTSD date+1, i.e.

(Nov. 1−Jan. 1)+2−(May 1−Jan. 1)+1, i.e.

304+2−120+1=245.

Thus, the predicted stabilization period for the November 1 "will heal in months" prognosis is 245 days. Because each of the time and medical practitioner weights is 1.0, the predicted period remains 245 days.

Had other recovery prognoses been considered, their predicted stabilization periods would have been modified by their time weights and medical practitioner weights. The model would have summed the resulting modified stabilization period for all prognoses and divided by the sum of the weights. In the example, with only one prognosis, the sum of the weighted stabilization days is 245. Dividing by the sum of the weights for each prognosis, in this case 1.0, the result is still 245 days.

Treatment months is the greater of the maximum treatment date, 156 days and the combined prognosis date, 245 days.

Continuing the example, the treatment time is 13 weeks, and the treatments months is 245 days, or 7.87 months. To determine the PTSD severity at 260, the engine first applies the treatment months to the table below to determine an assumed severity.

| Months | Treatment | Treatment | Depression | Time | Limits |
| --- | --- | --- | --- | --- | --- |
| 1 | 300 | 300 | 500 | 0 | 1,000 |
| 3 | 600 | 600 | 1,500 | 0 | 1,500 |
| 6 | 1,000 | 2,000 | 3,000 | 6 | 2,000 |
| 12 | 1,500 | 3,000 | 4,500 | 12 | 2,000 |
| 18 | 2,000 | 4,500 | 6,500 | 16 | 1,500 |
| 24 | 2,500 | 6,500 | 9,000 | 20 | 1,000 |
| 99 | 2,800 | 7,000 | 10,000 | 25.9 | 1,000 |

Column 1 is the treatment months. Column 2 is the assumed severity where the claimant has received recovery prognoses without other evidence of treatment. Column 3 is the severity where such evidence exists but where there is no depression diagnosis. Column 4 is the severity with treatment evidence and depression. Column 5 identifies the assumed treatment time for the corresponding treatment months, and column 6 represents limits on severity increases due to differences between actual and assumed treatment periods.

If recovery prognoses have been defined, but no treatment codes have been entered, the engine determines the assumed severity by column 2.

The use of column 4 depends upon the treatment months and the existence of a depression symptom. If no treatment codes have been entered, the engine refers to column 2, regardless of any depression diagnosis. If (1) treatment codes have been entered, (2) the claimant has depression and (3) treatment months is less than six months, the engine determines assumed severity from column 4. If (1) treatment codes have been entered, (2) the claimant has depression, (3) treatment months is less than 12 and (4) at least one of the treatment codes is among the group: 94.25, 94.31, 94.32, 94.33, 94.42, 94.44 and 94.49, the engine determines assumed severity from column 4. If (1) the claimant has had depression for more than 12 months, and (2) at least one of the treatment codes is among the group: 94.25 and 94.31, the engine determines assumed severity from column 4.

If the claimant has had depression for more than 12 months without seeking psychiatric drug therapy or psychotherapy treatments (ICD9 codes 94.25 and 94.31), the engine determines severity from column 3. If treatment codes have been entered and the claimant does not have depression, the engine determines assumed severity from column 3.

Recalling the example, treatment months is 7.87. The claimant has depression. The treatment months is less than 12, and the treatment codes are from the group of 94.25 and 94.31 codes. Accordingly, the engine determines assumed severity from column 4. Applying a linear interpolation for 7.87 months in column 1 to the assumed severities in column 4, the assumed severity is 3,467.74.

At 262, the engine compares the actual treatment time to the assumed treatment time in column 5 and adjusts the assumed severity for any difference. Applying a linear interpolation for 7.87 months to the assumed treatment time in column 5, the assumed treatment time, in weeks, is 7.87.

If the actual treatment time is less than the assumed treatment time, the engine first determines the severity that would have been assigned if no treatment codes had been provided in the case. It then determines the severity that would have been assigned if the actual treatment time had equaled the assumed treatment time. This creates a linear scale used to determine the final reduction value.

For example, assume that the actual treatment time for the above example was 3 weeks instead of 13 weeks. The calculated assumed treatment time is 7.87 weeks. Had no treatment codes been provided in the case, the assumed severity would have been determined from column 2 rather than column 3. Accordingly, in the first step, the engine employs a linear interpolation for the treatment months, 7.87, against the severities in column 2 to derive a "no treatment" severity of 1,155.83.

In step 2, the engine assumes that the actual treatment equals the assumed treatment time (7.87 weeks) and determines the severity against column 3. Applying a linear interpolation for 7.87 weeks against column 3, the "equal treatment" severity is 2311.67.

In step 3, the engine determines a severity for the actual treatment time between these extremes. In this example, the interpolation is between the "no treatment" and "equal treatment" treatment weeks and severities:

| Treatment Time (Weeks) | Severity |
| --- | --- |
| 0 | 1,155.83 |
| 7.87 | 2,311.67 |

Applying a linear interpolation for three weeks against the severity column, the "actual treatment" severity is 1,595.66. The severity adjustment is the "assumed treatment" severity, 2,311.67, minus the "actual treatment" severity, 1,595.66, or 716.01. Subtracting this from the calculated assumed severity, 3,476.74, the PTSD severity is 2,760.73.

Returning to the original example, the actual treatment time, 13 weeks, is greater than the assumed treatment time, 7.87 weeks. In this case, the engine determines a "maximum treatment time" according to the following:

min(min(A,B),C)—assumed treatment time, where
A=26,
B=Treatment Time, and
C=Treatment Months * (30/7)

Continuing the example, minimum treatment time is:

min(min(26,13),7.87(30/7))−7.87=5.13

Next, the engine determines the treatment limit based on column 6 of the table above. Applying a linear interpolation for 7.87 months against column 6, the treatment limit is 2,000.

The engine then determines the result of the following equation:

Min(26,treatment months(30/7))−assumed treatment time

In this example, treatment months is 7.87, and the assumed treatment time is 7.87 weeks. Thus, the result of the above equation is 18.13.

The severity adjustment is determined by finding the severity that corresponds to the result of the first step, 5.13, on a scale defined by the results of the second and third steps. That is, assuming that 5.13 weeks falls between 0 weeks and 18.13 weeks, and assuming that the severity for 0 weeks is 0 and that the severity for 18.13 weeks is 2,000, the severity value for 5.13 weeks is, by linear interpolation, 565.91. Adding to the calculated assumed severity, 3,467.74, the PTSD severity is 4,033.58.

5. Combine Severities

Referring again to FIG. 17, the engine combines the whole body pain and suffering from 264 with the PTSD severity through an amalgamate function at 275. If, however, the claimant is older than 10, and the PTSD severity is more than 2½ times the whole body severity from 264, the PTSD severity is reduced to 2½ times the value calculated at 264.

As an example, assume that the combined value at 264 is 3,066.58 and that the PTSD severity is 4,033.48. The engine determines a bound value as follows:

Bound=Min(300,000, 2(Whole Body Severity+PTSD severity))

For the above example,

Bound=Min(300,000, 2(3,066.58+4,033.48))=14,200.32

The whole body severity and the PTSD severity are divided by the bound prior to the amalgamate function. Thus, the amalgamate function combines values of 0.215951 and 0.284049 as follows:

Result=0+(1−0)0.215951+(1−0.215951) 0.284049=0.438659

Multiplying by the bound value, 14,200.32, the final severity is 6,229.10. This value is on the 0 to 300,000 scale and may therefore be divided by 3,000 in future calculations.

6. Determine Permanent Dysfunction

The pain and suffering, hospital/convalescent care, future treatment/complication and PTSD severities discussed thus far generally reflect the impact of the medical conditions on a claimant from their start dates to the point at which MMI is reached. As described above, however, some medical conditions never reach a zero dysfunction MMI. The claimant may, therefore, suffer some permanent dysfunction for which he may be compensated in general damages.

The engine assumes dysfunction at 266. The engine combines the profiles for the ICD9 codes entered for the case up to the whole body level, including the effect of prognoses, under the "second option" described above with respect to workers' compensation. That is, assuming that ICD9 codes have been defined for various body parts within the Little Man, the engine combines profiles at the body part level so that each body part has at most one profile. The engine then amalgamates component profiles with each other, and with their composite's profile, to determine a single profile for the composite. The composite's profile is, in turn, amalgamated with the component body part profiles for the higher-order composite of which it is itself a component. The combination continues until a profile is determined for the whole Body body part. Along the way, the engine modifies body part profiles as appropriate for prognoses applicable to the body parts.

As an example, assume that the left elbow has been dislocated and that the left forearm has a third-degree compression to the ulna nerve. The dislocation profile has a 0% residual dysfunction level, while the compression profile has a 30% residual level. A 15% AMA impairment prognosis has been applied to the left arm, and a future treatment (amputation—possible) has been applied to the left forearm.

Because each of the elbow and forearm has only one profile, and there is no profile assigned directly to the arm composite body part, there are no profile combinations at the body part level. To combine the elbow and forearm curves up to the arm level, the engine multiplies the dysfunction level for each day in each profile by the respective grouping value applicable to the arm and forearm. Since the residual level for the arm profile is 0, it remains 0 after application of its grouping value. The forearm, however, has a 30% residual level. Its grouping value, for combination up to the arm level, is 70%. Thus, at the arm level, the residual level contributed by the forearm is 0.3(0.7)=0.21. Because the arm's residual level is 0, the amalgamation of the arm and forearm curves results in a 21% residual level for the arm.

This residual level may be affected by prognoses. In the present example, no recovery prognoses are applied to the arm and forearm, and the engine therefore did not apply prognosis modifications to their curves. The arm composite, however, is assigned a 15% AMA impairment level. Assuming that this translates to a 15% dysfunction level, the engine changes the 21% residual level to 15%. The application of prognoses to body part profiles is described in detail above regarding workers' compensation processing.

Once the composite profile, including consideration for prognoses, has been determined, the engine considers the effect of future treatments and complications. In this case, the forearm has a "possible" amputation. The dysfunction level associated with an amputation is 100%. The factor associated with a probability of "possible" is 25%. Thus, the forearm dysfunction value associated with the future treatment is 25%. Applying the forearm's grouping value, 70%, the future treatment contributes a 17.5% dysfunction to the arm composite.

The engine chooses the larger of the amalgamated residual level, 15%, and the future treatment residual level, 17.5%, in this case 17.5%.

The left arm is a component of the "upper extremities" composite body part. The arm's grouping value to this composite is 60%. Thus, the arm passes a residual dysfunction of 0.175(0.6), or 10.5%, to the upper extremities body part. Assuming that there are no other medical conditions, and therefore no other profiles, applicable to the Little Man, the residual dysfunction level for the upper extremities body part is 10.5%. The grouping value for the upper extremities body part to its composite, the Whole Body, is 1.0. Thus, the Whole Body residual dysfunction level is 10.5%.

The engine adjusts the Whole Body dysfunction value based on the claimant's age as of the case start date, i.e. the date the initial injury occurred or was diagnosed. The engine determines a multiplying factor by linear interpolation of the claimant's age against the second column of the following table:

| Age (years) | Factor |
| --- | --- |
| 0 | 1.0 |
| 40 | 1.0 |
| 80 | 0.6 |
| 200 | 0.6 |

Assuming that the claimant in the above example is 40 or younger, the factor is 1.0, and the whole body dysfunction remains 10.5%.

At this point, permanent dysfunction is represented by a percent dysfunction value. The engine applies this dysfunction as a severity value in conjunction with permanent loss of amenities. The determination of loss of amenity severities is discussed in detail below.

7. Determine Temporary and Permanent Loss of Amenity Severity

The engine determines temporary and permanent loss of amenity severities at 268 and 270, respectively. FIG. 17 illustrates determination of the two severity types as separate steps because the two severity values are treated separately in conversion to general damages. As indicated below, however, these values are determined in parallel. Thus, it should be understood that the depiction of separate steps 268 and 270 in FIG. 17 is for purposes of clarity with respect to downstream processing.

Loss of amenities refers to the loss of the claimant's ability to enjoy life in the manner as if the claimant's injuries had not occurred. This is a loss separate from the pain and suffering, hospital/convalescent care, future treatment, complication, PTSD and permanent dysfunction severities described above. Those losses refer to the physical impact of medical conditions suffered by the claimant. Loss of amenities refers to the loss of ability to enjoy life that results from the physical impact. Temporary severity relates to temporary loss of capacity. The temporary period is equal to the injury, treatment or complication stabilization period. Permanent severity relates to permanent loss of capacity resulting from the injury, treatment or complication.

The engine considers the effect of the claimant's medical conditions on the following amenities:

Dexterity Capacity
Upper Extremity Capacity
Mobility Capacity
Personal Care Capacity
Hearing Capacity
Sight Capacity
Smell Capacity
Taste Capacity A group of body parts is associated with each of the above amenities. The engine determines the residual, permanent and/or future dysfunction levels for the body parts under each amenity and correlates these values to a severity for the amenity. It then combines the amenity severities for a total loss of amenity severity. The body parts for each amenity are listed below.

| Dexterity | Upper Extremities |
| --- | --- |
| R. Wrist and Hand | R. Arm |
| L. Wrist and Hand | L. Arm |
|  | Cervical Spine |
| Mobility | Personal Care |
| R. Leg | Trunk |
| L. Leg | Sight |
| Thoracic Spine | Consciousness |
| Lumbosacral Spine | Lymphatic System |
| Pelvis | Endocrine System |
| Loin/Groin | Urinary System |
| Buttocks | Behavior |
| Genitals | Communication |
| Abdomen | Reasoning/Memory |
| Balance | Balance |
| Cardiovascular System | Respiratory System |
| Respiratory System | Digestive System |
|  | Cardiovascular System |
|  | Circulatory System |
| Hearing | Sight |
| Hearing | Sight |

-continued

| Smell | Taste |
|---|---|
| Smell Nose | Taste |

For purposes of this discussion regarding loss of amenities, "residual dysfunction" refers to the final dysfunction level of an injury, complication or treatment profile that does not reach 0% dysfunction. "Permanent dysfunction" refers to the dysfunction level associated with a "loss of function," "disability rating" or "AMA" impairments entered through the prognosis data (FIG. 1). "Future dysfunction" refers to the residual dysfunction level of a future treatment or complication.

Although a severity is developed for each amenity, the severities are not equally weighted. The engine provides a greater weight to severities related to more significant amenities. The amenities, in order of significance are (1) sight, (2) dexterity, (3) care, (4) hearing, (5) upper extremities, (6) mobility, (7) taste and (8) smell.

a. Sight

Figure 21:
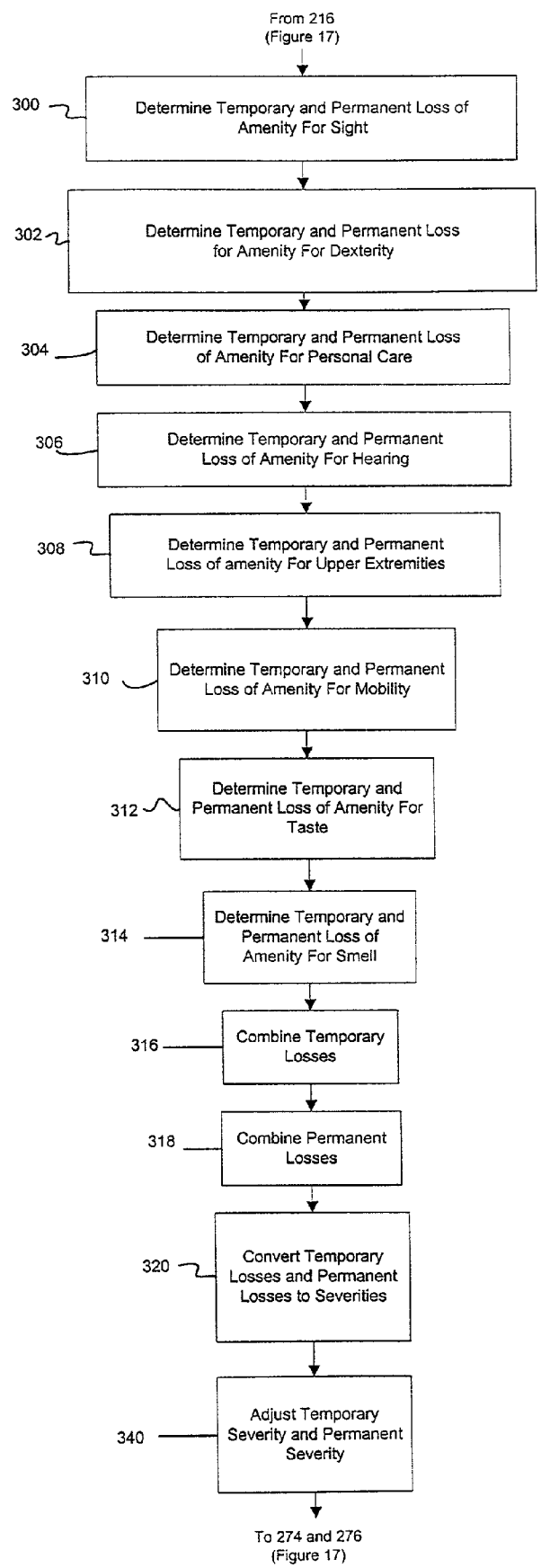
FIG. 21 is a flow chart illustrating the temporary and permanent loss of amenities steps of FIG. 17.

Referring to FIG. 21, the engine determines the temporary loss of amenity value for sight at 300. Initially, the engine determines the dysfunction curve for the sight composite body part by combining curves for its component body parts according to the "second option" build up procedure described above with respect to workers' compensation. This is similar to the amalgamation procedure described above with respect to permanent dysfunction. The temporary sight value is the area of the resulting profile for the sight body part, divided by 1,100, the approximate number of days in a three-year period. For example, assume that the profile for the sight body part derived by the amalgamation function is:

| Days | Dysfunction |
|---|---|
| 0 | 100 |
| 1 | 100 |
| 2 | 100 |
| 4 | 50 |
| 5 | 40 |
| 6 | 20 |
| 7 | 15 |
| 8 | 10 |
| 9 | 5 |
| 10 | 5 |

The temporary sight value is 445\1100=0.4045. The permanent sight value is the maximum of the residual dysfunction percentage, permanent severity value and future dysfunction value. Assuming that there are no impairment prognoses or future treatments/complications, the permanent sight value is 5.

b. Dexterity

The dexterity amenity includes 2 body parts: the left wrist and hand and the right wrist and hand. For each claimant, one of these body parts is preferred and one non-preferred. That is, the claimant is either left-handed or right-handed. At 302, the temporary dexterity value is (1) the sum of the preferred wrist and hand daily dysfunction levels, multiplied by 0.7, plus (2) the sum of the non-preferred wrist and hand daily dysfunction levels, multiplied by 0.3, divided by 1,100. Again, the profile for each of the two body parts is determined through the "second option" buildup routine of all profiles applicable to the left and right wrist and hand body parts and their components. Prognoses, including impairments, are considered. For simplicity, assume that the amalgamation routine results in the same profile for each of the two body parts. In the table below, column 2 represents the profile for the wrist and hand body part that is identified as preferred. Column 3 describes the dysfunction values of column 2, weighted by 0.7. Column 4 is the dysfunction profile for the wrist and hand identified as non-preferred, and column 5 describes those dysfunction levels weighted by 0.3.

| Days | Preferred Profile | Preferred Weights | Non-Preferred Profile | Non-Preferred Weighted |
|---|---|---|---|---|
| 0 | 100 | 70 | 100 | 30 |
| 1 | 100 | 70 | 100 | 30 |
| 2 | 100 | 70 | 100 | 30 |
| 4 | 50 | 35 | 50 | 15 |
| 5 | 40 | 28 | 40 | 12 |
| 6 | 20 | 14 | 20 | 6 |
| 7 | 15 | 10.5 | 15 | 4.5 |
| 8 | 10 | 7 | 10 | 3 |
| 9 | 5 | 3.5 | 5 | 1.5 |
| 10 | 5 | 3.5 | 5 | 1.5 |
| | | 311.5 | | 133.5 |

The temporary dexterity value is 445/1,100, or 0.4045.

The permanent dexterity value is the maximum of the preferred wrist and hand residual dysfunction percentage, permanent severity value and future dysfunction value, multiplied by 0.7, plus the maximum of the non-preferred wrist and hand residual dysfunction value, permanent severity value and future dysfunction value, multiplied by 0.3. Assuming no impairments or future treatment/complications, the permanent dexterity value is 5(0.7)+5(0.3)=5 c. Personal Care

The engine determines personal care amenities at 304. The table below describes weights applied to the dysfunction level for each day in the profile curve for each body part under the personal care amenity. Again, the profile for each body part is the "second option" buildup of the profiles for the components of each body part. Once each body part profile has been determined, the engine applies the function in the right-hand column of the table below to modify the dysfunction level for each day in the profile.

| Body Part | Weighted Dysfunction |
|---|---|
| Trunk | 0.4 (Dysfunction Level) |
| Sight | 1.6 (Max(Dysfunction Level − 50, 0)) |
| Consciousness | 1.0 (Dysfunction Level) |
| Lymph System | 2.0 (Max(Dysfunction Level − 50.0) |
| End. System | 1.6 (Max(Dysfunction Level − 50, 0)) |
| Urin. System | 0.4 (Dysfunction Level) |
| Behavior | 2.0 (Max(Dysfunction Level − 50, 0)) |
| Communication | 2.0 (Max(Dysfunction Level − 50, 0)) |
| Reasoning/Memory | 2.0 (Max(Dysfunction Level − 50, 0)) |
| Balance | 2.0 (Max(Dysfunction Level − 50, 0)) |

-continued

| Body Part | Weighted Dysfunction |
| --- | --- |
| Resp. System | 2.0 (Max(Dysfunction Level - 50, 0)) |
| Dig. System | 0.4 (Dysfunction Level) |
| Card. System | 2.0 (Max(Dysfunction Level - 50, 0)) |
| Circ. System | 2.0 (Max(Dysfunction Level - 50, 0)) |

For example, if each body part has the same profile as in the example above regarding sight and dexterity, the modified dysfunction level for the sight body part under personal care on day 0 is 80. On day 5, the modified dysfunction level for the communication body part is 0. On day 7, the modified dysfunction level for the digestive system is 6.

The engine then amalgamates the modified dysfunction levels for the personal care body parts, by day. For example, still assuming the same dysfunction curve for each body part as used in the above example, the dysfunction level for each personal care body part on day 0, modified according to the rules above, is:

| Body Part | Day 0 Modified Dysfunction |
| --- | --- |
| Trunk | 40 |
| Sight | 80 |
| Consciousness | 100 |
| Lymph System | 100 |
| Endocrine System | 80 |
| Urinary System | 40 |
| Behavior | 100 |
| Communication | 100 |
| Reasoning/Memory | 100 |
| Balance | 100 |
| Respiratory System | 100 |
| Digestive System | 40 |
| Cardio. System | 100 |
| Circulatory System | 100 |

Changing each dysfunction level to a decimal form (i.e. dividing by 100) and amalgamating the values for day 0 provides a result of 1.0. Multiplying by 100 to remove the decimal format, the amalgamated result is 100. The engine repeats this procedure for each day for which a modified profile dysfunction value exists. It then sums the amalgamated results and divides by 1,100. For the example above, the result is 0.58863.

Personal care is also affected by dexterity capacity and upper extremity capacity. Thus, in determining a temporary personal care value, the engine combines the temporary dexterity value, as discussed above, and the temporary upper extremity value, as discussed below, with the personal care result. First, however, the temporary dexterity value is multiplied by 0.7, and the temporary upper extremity value is multiplied by 0.6. These three values are amalgamated. Thus, assuming a temporary dexterity value of 0.4045 and a temporary upper extremity value of 0.4045, the engine amalgamates 0.58863, 0.28315 and 0.24270, for a result of 0.7767.

To determine the permanent personal care value, the engine finds, for each body part under personal care, (1) the residual dysfunction (i.e. the dysfunction level on the last day of the profile), modified by the applicable rule in the table above, (2) the permanent impairment, modified by the applicable rule in the above table, and (3) the future treatment/complication dysfunction level, modified by the applicable rule from the above table. The engine then finds, for each personal care body part, the maximum of these three numbers.

Assuming that the example does not include a permanent impairment or a future treatment/complication dysfunction level, the residual dysfunction level for each body part is 5%. Applying the rules above, the permanent level, by body part, is:

| | |
| --- | --- |
| Trunk | 2.0 |
| Sight | 0 |
| Consciousness | 5 |
| Lymphatic | 0 |
| Endocrine | 0 |
| Urinary | 2.0 |
| Behavior | 0 |
| Communication | 0 |
| Reasoning/Memory | 0 |
| Balance | 0 |
| Respiratory | 0 |
| Digestive | 2.0 |
| Cardiovascular | 0 |
| Circulatory | 0 |

Dexterity and upper extremity capacities are also considered. Assuming that the permanent values for both dexterity and upper extremities is 5, the contribution for dexterity is 0.7(5)=3.5, and the contribution from permanent upper extremity is 0.6(5)=3.0. The engine amalgamates these values, converted to decimal form (i.e. divided by 100), to determine a permanent personal care value. Amalgamating the values for the example above, the permanent personal care value is 16.305.

d. Hearing

Like sight, the hearing amenity has only one body part. At 306, the engine determines the temporary hearing value and permanent hearing value in the same manner as it determines the sight values described above. For example, assuming that the hearing body part has the same dysfunction profile as the sight body part in the above example, the temporary hearing value is 0.4045, and the permanent hearing value is 5.

e. Upper Extremities

The upper extremities amenity includes the right arm, left arm and cervical spine. To determine the temporary upper extremity value at 308, the engine first determines the dysfunction profile for each of these body parts. Again, the "second option" buildup routine is used, including prognoses. For each body part, the dysfunction level in the profile for each day is multiplied by a factor peculiar to that body part, producing a modified body part dysfunction profile. As with the wrist and hand body parts, one arm is preferred, and the other is non-preferred. The factor for the preferred arm is 0.55. The factor for the non-preferred arm is 0.45. The factor for the cervical spine is 0.3. For each day on which a dysfunction value exists, the engine determines a total dysfunction level according to the following equation:

$$\text{Combination} = 0.7(A+B)+C,$$

where
  A=modified dysfunction level for preferred arm,
  B=modified dysfunction level for non-preferred arm, and
  C=modified dysfunction level for cervical spine Accordingly, the combination value includes the effect of the preferred arm, non-preferred arm and cervical spine dysfunctions. The engine sums the combination values for all days and divides by 1,100 to arrive at the temporary upper extremity value.

For example, assuming that each of the left arm, right arm and cervical spine have the dysfunction profile shown in columns 1 and 2 of the table below, the modified dysfunction profiles are described in columns 3, 4 and 5. Column 6 describes the combination values determined according to the above equation.

| Days | Dysfunction | Preferred Arm Dysfunction | Non-Preferred Arm Dysfunction | Cervical Dysfunction | Combination |
|---|---|---|---|---|---|
| 0 | 100 | 55 | 45 | 30 | 100 |
| 1 | 100 | 55 | 45 | 30 | 100 |
| 2 | 100 | 55 | 45 | 30 | 100 |
| 4 | 50 | 27.5 | 22.5 | 15 | 50 |
| 5 | 40 | 22 | 18 | 12 | 40 |
| 6 | 20 | 11 | 9 | 6 | 20 |
| 7 | 15 | 8.25 | 6.75 | 4.5 | 15 |
| 8 | 10 | 5.5 | 4.5 | 3 | 10 |
| 9 | 5 | 2.75 | 2.25 | 1.5 | 5 |
| 10 | 5 | 2.75 | 2.25 | 1.5 | 5 |

Summing the combination values, and dividing by 1,100, the temporary upper extremity value is 0.4045.

In determining the permanent upper extremity value, the engine again finds the residual dysfunction, permanent severity and future dysfunction values for each of the three body parts. For each body part, the engine chooses the maximum value. Assuming that, for the above example, there are no impairments or future treatments or complications, the value for each of the three body parts is 5. The value for the preferred arm is multiplied by 0.55, and the value for the non-preferred arm is multiplied by 0.45. The sum of these modified values is multiplied by 0.7 and added to the cervical spine value, multiplied by 0.3. Thus, for the example above, the permanent upper extremity value is $0.7(0.55(5)+0.45(5))+0.3(5)=5.0$.

f. Mobility

The mobility processing at 310 is similar to personal care. In solving for the temporary mobility value, the engine determines the dysfunction curve for each body part. The dysfunction level at each day for each body part profile is modified according to the following weighting rules:

| Body Part | Weighted Dysfunction |
|---|---|
| Right Leg/ Left Leg | 0.7(larger dysfunction) + 0.3(lesser dysfunction) |
| Thoracic spine | 0.4(dysfunction level) |
| Lumbosacral spine | 0.6(dysfunction level) |
| Pelvis | 1.0(dysfunction level) |
| Loin/Groin | 0.5(dysfunction level) |
| Buttocks | 0.2(dysfunction level) |
| Genital organs | 0.5(dysfunction level) |
| Abdomen | 0.4(dysfunction level) |
| Balance | 1.0(dysfunction level) |
| Card. system | 2.0(Max(Dysfunction level − 50,0)) |
| Resp. system | 2.0(Max(Dysfunction level − 50,0)) |

As indicated in the table, the right and left legs are considered together. For each day that either the right leg or the left leg has a dysfunction level value, the engine selects the larger of the right leg and left leg values, multiplies by 0.7 and adds the result to the lesser value, multiplied by 0.3.

For example, assume that all mobility body parts, except for the left leg, have the dysfunction profile described below at columns 1 and 2. The left leg dysfunction profile is described by columns 1 and 3.

| Days | Body Part Dysfunction | Left Leg Dysfunction |
|---|---|---|
| 0 | 100 | 70 |
| 1 | 100 | 70 |
| 2 | 100 | 70 |
| 3 | 80 | 60 |
| 4 | 50 | 50 |
| 5 | 40 | 45 |
| 6 | 20 | 40 |
| 7 | 15 | 30 |
| 8 | 10 | 20 |
| 9 | 5 | 10 |
| 10 | 5 | 5 |

The modified dysfunction levels for the leg combinations on days 0 and 7 are 91 and 25.5, respectively. The modified dysfunction level for the abdomen on day 5 is 16.

The remaining routine for the temporary mobility value parallels the routine for temporary personal care. For each day, the engine amalgamates the modified dysfunction values for the mobility body parts. The amalgamated results for each day are summed, multiplied by 100 (to back out the decimal conversion done prior to the amalgamation), and divided by 1,100. For the above example, the temporary mobility value is 0.7557.

The calculation for the permanent mobility value parallels that of the permanent personal care value. For each mobility body part, the engine determines (1) the residual dysfunction of the body part's dysfunction curve, modified by the applicable rule above, (2) the permanent impairment level, modified by the applicable rule above and (3) the future treatment/complication dysfunction level, modified by the applicable rule above. Assuming that there are no impairments or future treatments/complications, the residual dysfunction for each body part is 5%. Applying the rules, the permanent values for each body part are:

| | |
|---|---|
| Legs | 5 |
| Thoracic | 2 |
| Lumbosacral | 3 |
| Pelvis | 5 |
| Loin/Groin | 2.5 |
| Buttocks | 1.0 |
| Genital Organs | 2.5 |
| Abdomen | 2 |
| Balance | 5 |
| Cardio. System | 0 |
| Respiratory System | 0 |

Amalgamating the above values, divided by 100, the permanent mobility value is 24.83.

g. Taste

Like hearing and sight, the taste amenity has a single body part. The temporary taste value and permanent taste value are determined at 312 in the same manner as are the temporary and permanent sight and hearing values, except that the permanent taste value is additionally multiplied by a factor of 0.4. For example, assuming that the taste body part has the same dysfunction profile as used above in the sight and hearing examples, the temporary taste value is 0.4045. The permanent taste value is 0.4(5)=2.

h. Smell

To determine the temporary smell value at 314, the engine first determines the dysfunction profile for the smell and nose body parts, again using the "second option" buildup procedure, including prognoses. The dysfunction level for each day in the nose profile is multiplied by 0.2. For each day, the engine amalgamates the smell dysfunction level and the modified nose dysfunction level. The engine sums the amalgamated results for each day and divides the result by 1,100.

For example, assume that the smell body part has the dysfunction profile described by columns 1 and 2 below, and that the nose body part has the dysfunction profile defined by columns 1 and 3. The modified nose dysfunction profile is described by columns 1 and 4. Column 5 is the amalgamated combination of columns 2 and 4.

| Days | Smell Dysfunction | Nose Dysfunction | Modified Dysfunction | Combination |
|---|---|---|---|---|
| 0 | 100 | 60 | 12 | 100 |
| 1 | 100 | 60 | 12 | 100 |
| 2 | 100 | 60 | 12 | 100 |
| 4 | 50 | 40 | 8 | 54 |
| 5 | 40 | 40 | 8 | 44.80 |
| 6 | 20 | 20 | 4 | 23.2 |
| 7 | 15 | 20 | 4 | 18.4 |
| 8 | 10 | 20 | 4 | 13.6 |
| 9 | 5 | 10 | 2 | 6.9 |
| 10 | 5 | 5 | 1 | 5.95 |

Summing column 5, and dividing by 1,100, the temporary smell value is 0.4244.

To determine the permanent smell value, the engine finds the residual dysfunction value, impairment value and future treatment/complication value for the smell body part and the nose body part. For each body part, it selects the maximum value, multiplying the nose value by 0.2. The two values are amalgamated to arrive at the permanent smell value. For the example above, assuming that there are no impairments or permanent treatments or complications, the permanent smell value is 5.95.

The engine finds the combined temporary loss of amenity value and the combined permanent loss of amenity value at 316 and 318. Referring to the table below, columns 2 and 3 describe the temporary and permanent amenity values for the amenities described above. Dexterity and upper extremities are included in the personal care values and are, therefore, omitted.

| | Adjusted Temp. | Adjusted Perm. | Rate | Temp. | Perm. |
|---|---|---|---|---|---|
| Sight | 0.4045 | 5 | 1 | 0.4045 | 5 |
| Per. Care | 0.7767 | 16.30 | 0.6 | 0.4660 | 9.783 |
| Hearing | 0.4045 | 5 | 0.6 | 0.2427 | 3.0 |
| Mobility | 0.7557 | 24.83 | 0.5 | 0.3778 | 12.42 |
| Taste | 0.4045 | 2 | 0.2 | 0.0809 | 0.4 |
| Smell | 0.4244 | 5.95 | 0.1 | 0.0424 | 0.595 |

The engine multiplies each temporary value, and each permanent value, by the rate for each amenity in column 4. These rates reflect the relative significance of each amenity.

The adjusted temporary and permanent values are provided in columns 5 and 6, respectively.

To determine the final temporary amenity value at 316, the engine amalgamates the adjusted temporary values in column 5. Prior to the amalgamation, the temporary values are divided by 100. The amalgamated result, multiplied by 100, is 2.061. Repeating the procedure for the adjusted permanent amenity values at 318, the amalgamated permanent amenity value is 31.995.

To convert the temporary amenity value to a severity at 320, the engine applies the amalgamated temporary amenity value to the following table:

| Temporary Amenity | Severity |
|---|---|
| 0 | 0 |
| 10 | 2,000 |
| 20 | 4,000 |
| 30 | 6,000 |
| 40 | 7,500 |
| 50 | 9,000 |
| 100 | 0,000 |

Interpolating for the amalgamated temporary amenity value of the above example, 2.061, the temporary amenity severity is 412.29.

The permanent amenity severity value is calculated at 320 from the following table:

| Permanent Amenity | Severity |
|---|---|
| 0 | 0 |
| 10 | 8,000 |
| 20 | 16,000 |
| 30 | 24,000 |
| 40 | 30,000 |
| 50 | 36,000 |
| 100 | 40,000 |

Interpolating for the amalgamated permanent value for the above example, 31.995, the permanent severity is 25,196.98.

Permanent severity is defined on a scale from 0 to 150,000, whereas temporary severity is defined on a scale from 0 to 300,000. For ease of computation at 340, the temporary severity may be divided by 3,000, and the permanent severity may be divided by 1,500, providing final temporary and permanent loss of amenity severities of 0.1374 and 16.798, respectively.

8. Combined Severities

The engine has now calculated the following: (1) whole body pain and suffering severity, including injuries, treatments, complications, hospital/convalescent care, future treatments/complications and PTSD (2) temporary loss of amenity severity, (3) permanent dysfunction, and (4) permanent loss of amenity severity. The engine recognizes a distinction between present and future conditions in converting from severity values to general damage values, and, therefore, maintains the distinction as it combines severity values. Accordingly, the engine amalgamates whole body pain and suffering with temporary loss of amenities at 274 and then separately amalgamates permanent dysfunction and permanent loss of amenities at 276.

For example, assume that whole body pain and suffering severity is 35,678.4 on a 0-300,000 scale. Assume also that the temporary amenity severity is the value calculated above, 0.1374313. Bringing the pain and suffering severity to the same scale as the temporary amenity severity, the whole body value is divided by 3,000, resulting in 11.8928. After dividing these values by 100 and amalgamating, the combined value is 0.1201388. Multiplying by 100 to back out the decimal format, the combined severity value is 12.01388.

Assume that the whole body permanent dysfunction value is 10.50 and that the permanent loss of amenity severity is 16.797984. The engine treats the dysfunction value as a severity and amalgamates the two values. After dividing by 100, the amalgamated result is 0.2553419. Multiplying by 100, the total dysfunction severity is 25.53419.

The engine also combines whole body pain and suffering severity from 275, temporary loss of amenity severity from 268, permanent loss of amenity severity at 270, permanent dysfunction severity from 266 and additional allowances (described below) from 282 into a combined case level severity at 277. Prior to the combination, each of whole body pain and suffering severity, temporary amenity severity and permanent amenity severity is divided by 100. The model modifies the permanent dysfunction severity from 266 (PDS) according to the following equation:

$$\text{mod. per. dys. sev.} = PDS + (PDS^2/100)(1/2)$$

Additional allowances from 282 is a monetary value. The model converts to a severity:

$$\text{Allowance severity} = \text{Allowance/multiplier}$$

where "multiplier" is the user-defined general damages conversion multiplier described below with respect to step 278. The model divides the resulting five values by 100, amalgamates and multiplies the amalgamated result by 100 to produce the combined case level severity, which is reported to the user on the general damages assessment at 206 (FIG. 16).

9. Conversion to General Damages

Because general damages awards may vary from jurisdiction to jurisdiction, the engine's determination of the impact of present and future medical conditions center on severity values rather than monetary values. Accordingly, the Tuning Wizard (FIG. 1) includes two user-definable multipliers that enable the engine to convert total pain and suffering and total dysfunction severity values to monetary values at 278 and 280. Prior to applying the multipliers, however, the model applies a pre-conversion factor defined by the user. The severity values from steps 274 and 276 are on a 0-100 scale. Accordingly, for both total pain and suffering and total dysfunction, the user enters pre-conversion factors, in %, for steps within the 0-100 severity scale. The default tables are:

| Total Pain and Suffering | | Total Dysfunction | |
|---|---|---|---|
| Severity | Pre-Conv. Factor | Severity | Pre-Conv. Factor |
| 0 | 100 | 0 | 100 |
| 100 | 100 | 100 | 100 |

That is, the pre-conversion factor is 1 for all severities. Assume, however, that the initial pre-conversion factor is set to 0 in the total dysfunction table. By linear interpolation, the total dysfunction severity calculated above, 25.53419, is multiplied by 0.2553419 before application of the general damages multiplier.

The user may define the pain and suffering multiplier, and the dysfunction multiplier, through the Tuning Wizard (FIG. 1). The model provides 32 example medical conditions. The user, preferably through an assessment expert in the region for which the model is used, enters his assessment of the pain and suffering damages, and the dysfunction damages, for each example condition. The model also has a severity value for each condition. Thus, both for pain and suffering and for dysfunction, the model has a plot of monetary damages v. severity. The Tuning Wizard applies a least squares average to each plot, thereby determining linear relationships between monetary damages and severity for pain and suffering and for dysfunction. These linear relationships define the conversion multipliers used at steps 278 and 280.

Continuing the above example, and assuming the default pre-conversion tables, assume that the user operates in the United States and has determined a total pain and suffering multiplier through Tuning Wizard of 3,000. The total pain and suffering severity, 12.01388, multiplied at 278 by 3,000, provides a pain and suffering contribution to general damages of $36,041.64. Assume also that the user has determined a total dysfunction severity multiplier through Tuning Wizard of 1,500. The total dysfunction severity, 25.53419, multiplied at 280 by 1,500, provides a dysfunction portion contribution to general damages of $38,301.29.

In determining general damages, the engine also considers a monetary allowance entered by the user for additional compensation, for example due to disfigurements resulting from scars and plastic surgery. The user determines this allowance externally of the engine and enters a monetary value through the Case Notebook (FIG. 1). The engine, however, scales the entered allowance based on the dysfunction severity. In general, the greater the dysfunction suffered by the claimant, the less the impact of a disfigurement. Accordingly, the engine determines a multiplier equal to (1−(dysfunction severity/100)) that it applies to the user-defined allowance. For example, assume that the dysfunction level is 10.5 from the example above and that the user has entered a $500 allowance. At 282, the engine determines the allowance contribution to general damages, in this case $447.50.

At 284, the engine determines a likely range of general damages for the case. The high end of the range is equal to the sum of the total pain and suffering general damages contribution, the total dysfunction general damages contribution, and the allowance general damages contribution, rounded to the nearest 100. For the above example, the general damage's high end is $36,041.64+$38,301.29+$447.50, rounded to nearest $100, or $74,800.

The low end of the general damages range is derived from discount percentages entered by the user. The user may enter a discount percentage for successive monetary ranges, for example 15% for the first $1,000,000, 20% for the next $500,000, etc. The user defines both the monetary ranges and the discount percentages. The engine sums the total pain and suffering and total dysfunction general damages contributions, discounts by the appropriate percentage and adds to the adjusted disfigurement allowance. Continuing the example, assume that the user has entered a 15% discount percentage for a 0-$1,000,000 range. The sum of the total pain and suffering and total dysfunction general damages contributions is $74,037.70. Multiplying by 0.85, adding the adjusted additional allowance amount, $447.50, and rounding to the nearest $100 (to nearest $10 if less than or equal to $1,000 or to nearest $1,000 if above $100,000), the general damages low end is $62,900.00. Accordingly, the engine assesses a range for a general damages award to this claimant of $62,900.00-$74,800.00.

D. Determine Past Economic Loss

Returning to FIG. 16, the engine also assesses salary lost by the claimant due to the claimant's injuries at 202. Although this is referred to as "past" economic loss, the user may define salary loss into the future where loss periods are predictable. Accordingly, the engine determines past economic loss based on defined time periods and salary rates applicable to those periods. Multiple salary periods may be defined.

The user may define the time-off-work periods and/or may define a start date and allow the engine to derive an end date. The user also enters the salary applicable to the time-off-work period and the salary frequency, for example weekly, bi-weekly, monthly or bi-monthly.

For example, if the claimant has been out of work for a period of time prior to the time at which the user enters the case information, and is expected to remain out of work until a known date in the future, the user enters the date the claimant stops working and the date the claimant is expected to return to work. If the claimant is paid $800 per week, the user enters $800 and enters a code that corresponds to a weekly pay period. The engine then determines the number of weeks the claimant is out of work and multiplies by the salary to determine past economic loss attributable to this time period.

If the claimant is unable to work, and there is no estimate of the date on which he will be able to return to work, the engine determines a return-to-work date using the workers' compensation processing described above. This requires that the user enter occupation data or point to an occupation in the dictionary of occupational titles. In estimating a time-off-work period, the engine stretches all applicable dysfunction profiles to their stabilization days as in common law processing. It does not consider the possibility of alternate occupations. Assuming that the user enters a start date for the time-off-work period, the engine determines the end date as the latest task date for the Task Wizard occupation or as the latest DOT occupation activity date. The engine then calculates the past economic loss value for the period, based on the entered salary and pay period information.

If it is expected that the claimant will never return to work, or if in executing the time-off-work estimate the engine determines that the claimant will never return to work, the engine provides past economic loss up to the case run date and prompts the user to enter sufficient information for an assessment of future economic loss, as described below. The user may also directly define a past economic loss period extending from the earliest injury date to present and allocate later salary loss to the future economic loss assessment.

E. Determine Future Economic Loss

The engine determines future economic loss at 204. Generally, future economic loss is an assessment of the likelihood that the claimant will not be able to work in the same occupation, or will not be able to work at all, for some period in the future. The user enters start and end dates for the future economic loss period, the loss amount and the applicable salary frequency, a capitalization rate and a vicissitudes rate.

The start and end dates depend on the type of loss that the claimant is expected to suffer. For example, the claimant may be able to continue his occupation at present but, due to the injury, is expected to work 10 fewer years than he would if the injury had not occurred. Assuming that the claimant would normally expect to work 35 years from the present, the start and end dates would be 25 years and 35 years, respectively, from the present day.

The loss amount is the difference between what the claimant would be expected to earn during the loss period if the injury had not occurred and what the claimant is expected to earn during the loss period after the injury has occurred. For example, if the claimant is expected to be able to earn $600 per week after the injury, but would have been expected to earn $800 a week if the injury had not occurred, the loss amount is $200. The pay period would be weekly. The capitalization rate is a discount rate used to bring the future loss to a present value. The vicissitudes rate reflects the likelihood that the claimant would have lived long enough to attain his expected income had the injury not occurred.

The user also enters a code that reflects the likelihood that the claimant will suffer the future economic loss. In one embodiment, the options are "possible," "probable" and "definite." These likelihoods correspond to probability rates of 0.25, 0.6 and 1.0, respectively.

As an example, assume that the loss amount is $100 for a weekly pay period, the loss start date is March 27, the loss end date is April 6, the capital rate is 5%, the vicissitudes rate is 15% and the case run date is March 27. The daily loss amount is $14.29. The daily capitalization rate is (1+(5/100))**(1/365)=1.0001336806. There are 10 days in the payment period.

The engine determines an annuity rate for each day in the loss period. The annuity rate for each day k is.

$$\text{annuity rate}(k) = \text{annuity rate}(k-1) + 1/(\text{daily capitalization rate})^k,$$

where annuity rate (0)=0.

The engine multiplies the daily loss amount by the annuity value for the last day in the period, day 10, in this case 9.9926515. The result is 142.75.

If the future economic loss start date is greater than the case run date, the result of the previous step is multiplied by a factor of:

$$(1/\text{daily capitalization rate})**(\text{future economic loss start date}-\text{case run date}).$$

In this case, the future economic loss start date and the case run date are the same, and the annuity value therefore remains 142.75.

The engine then discounts the annuity value based on the probability that the future economic loss will occur. Assume that the user has entered a "definite" probability. The annuity value therefore remains 142.75.

The engine then discounts the annuity value by the vicissitudes rate. Here, the vicissitudes rate is equal to 15%, and the engine therefore multiplies the annuity value by 0.85. Rounding to the nearest dollar, the annuity value is 121. Thus, the future economic loss amount for this assessment is $121.

The engine has now determined a general damages range and assessments for past and future economic loss. These assessments are displayed to the user at 206, for example through a computer screen display or through a printed report. At 208, the engine displays the case information, medical details, claimant details and prognoses entered for the case so that the user may confirm the accuracy of the assessment.

While preferred embodiments of the invention have been described above, it should be understood that any and all equivalent realizations of the present invention are included within the scope and spirit thereof. For example, it should be understood that there can be other suitable capacity level profile definitions, prognoses algorithms and criteria, and severity computations. Thus, the embodiments are presented by way of example only and are not intended as limitations upon the present invention, and those of ordinary skill in this art should understand that many modifications may be made. Therefore, it is contemplated that any and all such embodiments are included in the present invention as may fall within the literal or equivalent scope of the appended claims.

What is claimed is:

1. A computerized method for assessing medical conditions affecting medically impaired person, said method comprising the steps of:
   a) inputting into a computer a plurality of profiles relating predetermined transient medical conditions to human body parts, each said profile estimating a time progression of a dysfunction level or a capacity of at least one said body part from a time of injury over a specific progressive time scale into the future, due to at least one said condition;
   b) identifying one or more said predetermined transient medical conditions that currently affect said person;
   c) selecting a said profile corresponding to each said transient medical condition;
   d) relating said selected profile's time dimension to an occurrence of its said transient medical condition; and
   e) generating and outputting on an output device an assessment of an impact of said medical conditions on said person, wherein said assessment is based on said profiles related to said medical conditions at step (d).

2. The method as in claim 1, wherein said human body parts are classified into a multi-level hierarchy, each said body part in each level of said hierarchy below a highest level of said hierarchy being a component body part of a composite body part in a higher level in said hierarchy.

3. The method as in claim 2, including the steps
   e) for at least one said composite body part having a said selected profile, allocating said estimated capacity of said selected profile among said component body parts of said composite body part, and
   f) creating an inherited profile for each said component body part of said composite body part of step (e), said inherited profile describing said estimated capacity allocated to said component body part from said composite body part over time,
   wherein said assessment is based on any said inherited profiles at step (f).

4. The method as in claim 3, including the step
   g) for each said component body part having multiple said selected profiles and/or said inherited profiles, combining said multiple profiles so that each said component body part has at most one profile that describes an estimated capacity of said component body part over time,
   wherein said assessment is based on any said at most one profile at step (g).

5. The method as in claim 4, including, following step (g), the step
   h) combining, up to each said composite body part, said at most one profile of each said component body part of said composite body part so that each said composite body part has at most one profile that describes an estimated capacity of said composite body part over time,
   wherein said assessment is based on any said at most one profile at step (h).

6. The method as in claim 5, wherein said combining step (h) includes combining said profiles of said component body parts of at least one said composite body part based on the spatial relationship among said component body parts within the human body.

7. The method as in claim 5, wherein the magnitude of said estimated capacity contributed to said composite profile by a said component profile combined at step (h) is positively related to the spatial distance between said component body part and other said component body parts of said composite body part.

8. The method as in claim 5, wherein said combining step (h) combines estimated capacities D(i) for each profile day among said profiles of said component body parts up to an estimated capacity X(M) for said profile day for at least one said composite body part, where $X(i)=X(i-1)+(1-X(i-1))D(i)$, for i=1 to M, where M is the number of profiles being combined, D(i) is in decimal format, and X(0)=0.

9. The method as in claim 5, wherein, for each said component of said composite of step (h), the magnitude of the estimated capacity contributed to said composite profile by said profile of said component body part is modified by a scaling factor that relates said component body part's contribution to the capacity of said composite body part.

10. The method as in claim 9, wherein said scaling factor includes a first part that relates said component body part's contribution to the capacity of a group of said components and a second part that relates said group's contribution to the capacity of said composite body part.

11. The method as in claim 1, including the step
    e) modifying at least one said selected profile based on an assessment by a medical practitioner of said medical condition to which said selected profile corresponds,
    wherein said assessment is based on any said profiles modified at step (e).

12. The method as in claim 11, wherein step (e) includes comparing said assessment to said selected profile,
    determining whether said assessment at step (e) agrees with said selected profile according to first predetermined criteria dependent upon said assessment,
    leaving said selected profile unchanged with respect to said assessment if said assessment agrees with said selected profile according to said first predetermined criteria, and
    changing said profile according to second predetermined criteria dependent upon said assessment if said assessment does not agree with said selected profile according to said first predetermined criteria.

13. The method as in claim 1, wherein said estimated capacity is related to a dysfunction level.

14. The method as in claim 1, wherein step (c) includes modifying said selected profiles according to predetermined rules based on one or more characteristics of said medical condition and/or said person.

15. A computerized method for assessing an impact of medical conditions and impairments affecting a person, said method comprising the steps of:
    a) inputting into a computer a plurality of profiles relating predetermined transient medical conditions to human body parts, each said profile estimating a time progression of a dysfunction level or a capacity of at least one said body part from a time of injury over a specific progressive time scale into the future, due to at least one said condition;

b) identifying one or more said body parts that affect performance of a job by said person;

c) determining what capacity level of each said one or more body parts inhibits said person from performing said job;

d) identifying one or more said predetermined transient medical conditions that currently affect said person;

e) selecting a said profile corresponding to each said one or more transient medical conditions;

f) relating each said selected profile's time dimension to an occurrence of its said transient medical condition;

g) for each said selected profile applicable to a said body part determined at step (b), determining a date for said applicable selected profile upon which said estimated capacity profiled by said applicable selected profile first moves beyond said capacity level determined at step (c) for its said body part so that said transient medical condition to which said applicable selected profile corresponds does not inhibit said job;

h) determining the latest said date determined at step (g); and i) generating and outputting said latest date on an output device.

16. The method as in claim 15, wherein said estimated capacity is related to a dysfunction level and wherein step (g) includes determining said date from said applicable selected profile upon which said dysfunction level profiled by said applicable selected profile falls below said dysfunction level determined at step (c) for its said body part.

17. The method as in claim 16, wherein, where said estimated capacity of said applicable selected profile fails to move beyond said capacity level determined at step (c) for its said body part so that said medical condition to which said applicable selected profile corresponds does not inhibit said job, said date determined at step (g) indicates that said condition always inhibits said job.

18. The method as in claim 15, including, following step (f) and prior to step (g), the step i) for each said body part determined at step (b) having multiple said selected profiles, combining said multiple profiles so that said body part has one profile that describes an estimated capacity of said body part over time, and wherein said combined profile from step (i) is said applicable selected profile at step (g) for said body part to which said combined profile applies.

19. The method as in claim 15, wherein said human body parts are classified into a multi-level hierarchy, each said body part in each level of said hierarchy below a highest level of said hierarchy being a component body part of a composite body part in a higher level in said hierarchy.

20. The method as in claim 19, including, following step (f) and prior to step (g), the steps i) for at least one said composite body part having a said selected profile, allocating said estimated capacity of said selected profile among said component body parts of said composite body part, and j) creating an inherited profile for each said component body part of said composite body part of step (i), said inherited profile describing said estimated capacity allocated to said component body part from said composite body part over time.

21. The method as in claim 20, including, following step (j) and prior to step (g), the step k) for each said body part that is a said body part determined at step (b) or a lower-level component body part of a said body part determined at step (b) and that has multiple said selected profiles and/or said inherited profiles, combining said multiple profiles so that said body part has one profile that describes an estimated capacity of said body part over time, and wherein said combined profile from step (k) is said applicable selected profile at step (g) for said body part to which said combined profile applies.

22. The method as in claim 21, including, following step (k) and prior to step (g) the step l) combining, up to each composite body part that is a said body part determined at step (b) or a lower-level component body part of a said body part determined at step (b), said profile of each said component body part of said composite body part so that said composite body part has at most one profile that describes an estimated capacity of said composite body part over time, and wherein said combined profile from step (l) is said applicable selected profile at step (g) for said composite body part to which said combined profile applies.

23. The method as in claim 15, including, following step (f) and prior to step (g) the step i) modifying at least one said selected profile based on an assessment by a medical practitioner of said medical condition to which said selected profile corresponds.

24. The method as in claim 15, wherein step (g) includes modifying said date based on an assessment by a medical practitioner of said person's ability to perform an act used in performing said job.

25. The method as in claim 24, wherein said modifying step of step (g) includes comparing said assessment to said date;

determining whether said assessment agrees with said date according to first predetermined criteria dependent upon said assessment, leaving said date unchanged with respect to said assessment if said assessment agrees with said date according to said first predetermined criteria, and changing said date according to second predetermined criteria dependent upon said assessment if said assessment does not agree with said date according to said first predetermined criteria.

26. The method as in claim 15, wherein step (h) includes modifying said latest date based on an assessment by a medical practitioner of said person's ability to perform said job.

27. The method as in claim 26, wherein said modifying step of step (h) includes comparing said assessment to said latest date;

determining whether said assessment agrees with said latest date according to first predetermined criteria dependent upon said assessment, leaving said latest date unchanged with respect to said assessment if said assessment agrees with said latest date according to said first predetermined criteria, and changing said latest date according to second predetermined criteria dependent upon said assessment if said assessment does not agree with said latest date according to said first predetermined criteria.

28. The method as in claim 15, wherein step (e) includes modifying said selected profiles according to predetermined rules based on one or more characteristics of said medical condition and/or said person.

29. A computerized method for assessing an impact of medical conditions and impairments affecting a person, said method comprising the steps of:

a) inputting into a computer a model of a human body, said model including multi-level hierarchy of body parts that, in combination with each other, form the human body;

b) inputting into a computer, for each transient medical condition of a plurality of predetermined transient medical conditions, a severity value that estimates a time progression of a dysfunction level produced by said transient medical condition on at least one said body part from a time of injury over a specific progressive time scale into the future;

c) identifying one or more said predetermined transient medical conditions that currently affect said person;

d) combining said severity values for said transient medical conditions identified at step (c) to a combined severity value; and e) generating and outputting on an output device an assessment an assessment of an impact of said medical conditions on said person, wherein said assessment is based on said combined severity value.

30. The method as in claim 29, wherein said severity values are non-monetary values, and wherein step (d) includes converting said combined severity value to a monetary value, and
wherein said assessment is based on said monetary value.

31. The method as in claim 30, wherein step (b) includes providing a plurality of profiles relating said predetermined medical conditions to said body parts, each said profile describing an estimated capacity of at least one said body part, due to at least one said condition, over time, wherein each said profile is assigned a said severity value.

32. The method as in claim 31, wherein step (d) includes the step
e) for each said body part having multiple said medical conditions identified at step (c), prior to combining said severity values to said combined severity value, combining said severity values corresponding to said identified medical conditions to a total severity value for said body part, and
f) combining body part severity values up to said combined severity value.

33. The method as in claim 32, wherein said combining step (e) includes combining said multiple severity values based on the time at which said medical conditions to which said multiple severity values correspond occur and on the length of said profiles corresponding to said body parts.

34. The method as in claim 33, wherein said human body parts are classified into a multi-level hierarchy, each said body part in each level of said hierarchy below a highest level of said hierarchy being a component body part of a composite body part in a higher level in said hierarchy.

35. The method as in claim 34, wherein step (f) includes, for each said composite body part prior to combining up to said combined severity value, combining said severity value of each said component body part of said composite body part up to a composite body part severity value for said composite body part.

36. The method as in claim 35, wherein said combining step (f) includes combining said severity values of said component body parts of at least one said composite body part based on the spatial relationship among said component body parts within the human body.

37. The method as in claim 31, wherein step (d) includes the step
e) for each said body part having multiple said medical conditions identified at step (c), prior to combining said severity values to said combined severity value, combining said severity values corresponding to said identified medical conditions to a total severity value for said body part, and
f) combining body part severity values up to said combined severity value.

38. The method as in claim 37, wherein said combining step (e) includes combining said multiple severity values based on the time at which said medical conditions to which said multiple severity values correspond occurred.

39. The method as in claim 37, wherein said human body parts are classified into a multi-level hierarchy, each said body part in each level of said hierarchy below a highest level of said hierarchy being a component body part of a composite body part in a higher level in said hierarchy.

40. The method as in claim 39, wherein step (f) includes, for each said composite body part prior to combining up to said combined severity value, combining said severity value of each said component body part of said composite body part up to a composite body part severity value for said composite body part.

41. The method as in claim 40, wherein said combining step (f) includes combining said severity values of said component body parts of at least one said composite body part based on the spatial relationship among said component body parts within the human body.

42. The method as in claim 41, wherein step (f) includes combining said severity values of said component body parts and said composite body parts up to said combined severity value so that said combined severity value corresponds to the whole human body.

43. The method as in claim 42, wherein said severity values are non-monetary values and wherein step (d) includes converting said combined severity value to a monetary value.

44. The method as in claim 29, including, prior to combining said severity values to said combined severity value, the step
e) modifying at least one said severity value based on an assessment by a medical practitioner of said medical condition to which said severity value corresponds.

45. The method as in claim 31, including, prior to combining said severity values to said combined severity value, the steps
f) modifying at least one said selected profile based on an assessment by a medical practitioner of said medical condition to which said, selected profile corresponds, and
g) for each said selected profile modified at step (f), modifying said severity value corresponding to said selected profile based on the modification to said selected profile at step (f).

46. The method as in claim 29, wherein, for a said medical condition corresponding to a whiplash injury, step (b) includes deriving said severity value for said injury based on treatment applied to said whiplash injury.

47. The method as in claim 46, wherein said deriving step includes deriving said severity value for said whiplash injury based on treatment applied to said whiplash injury and on the type of medical practitioner that provided said treatment.

48. The method as in claim 29, including the step
e) where said person has spent time in a hospital as a patient, providing a severity value that describes the impact on said person of said time,
wherein said assessment is based on any said severity provided at step (e).

49. The method as in claim 29, including the step
e) where said person has received convalescent care, providing a severity value that describes the impact on said person of time spent by said person under said convalescent care,
wherein said assessment is based on any said severity provided at step (e).

50. The method as in claim 29, including the step
e) where said person is predicted to suffer a medical condition in the future, providing a severity value that describes the impact on said person of said medical condition,
wherein said assessment is based on any said severity provided at step (e).

51. The method as in claim 50, including scaling said severity value provided at step (e) by a factor corresponding to a predicted likelihood that said future medical condition will occur.

52. The method as in claim 29, wherein, for a said medical condition corresponding to a post traumatic stress disorder, step (b) includes deriving said severity value for said medical condition based on treatment applied to said post traumatic stress disorder.

53. The method as in claim 52, wherein said deriving step includes deriving said severity value for said post traumatic stress disorder based on treatment applied to said post traumatic stress disorder and on the type of medical practitioner that provided said treatment.

54. The method as in claim 29, including the step
e) where said person has suffered a loss of ability to enjoy life, providing at least one severity value that describes the impact on said person of said loss of ability to enjoy life,
wherein said assessment is based on any said severity provided at step (e).

55. The method as in claim 54, wherein step (e) includes providing a said at least one severity value that describes the impact on said person of temporary loss of ability to enjoy life.

56. The method as in claim 54, wherein step (e) includes providing a said at least one severity value that describes the impact on said person of permanent loss of ability to enjoy life.

57. The method as in claim 29, including the step
e) where said person has suffered a permanent dysfunction, providing a severity value that describes the impact on said person of said permanent dysfunction, and
wherein said assessment is based on any said severity provided at step (e).

58. The method as in claim 29, including the steps
e) where said person has spent time in a hospital as a patient, providing a severity value that describes the impact on said person of said time,
f) where said person has received convalescent care, providing a severity value that describes the impact on said person of time spent by said person under convalescent care,
g) where said person is predicted to suffer a medical condition in the future, providing a severity value that describes the impact on said person of said medical condition,
h) where said person has suffered post traumatic stress syndrome, providing a severity value that describes the impact on said person of said post traumatic stress syndrome,
i) where said person has suffered a temporary loss of ability to enjoy life, providing at least one severity value that describes the impact on said person of said loss,
j) where said person has suffered a permanent loss of ability to enjoy life, providing at least one severity value that describes the impact on said person of said loss, and
k) where said person has suffered a permanent dysfunction, providing a severity value that describes the impact on said person of said permanent dysfunction,
wherein said assessment is based on any said severities provided at steps (e)-(k).

59. The method as in claim 58, including the step
l) combining any said severity values provided at steps (e)-(k) with said combined severity value, wherein said assessment is based on a combined severity value from step (l).

60. The method as in claim 59, wherein said severity values are non-monetary values,
wherein step (l) includes converting any said
severity values provided at steps (e)-(k) and said combined severity value to a monetary value, and
wherein said assessment is based on said monetary value.

61. The method as in claim 60, wherein step (l) includes expressing said monetary value as a range of expected monetary values.

62. The method as in claim 60, wherein step (l) includes the steps
m) combining any said severity values provided at steps (e)-(i) with said combined severity value,
n) combining any said severity values provided at steps (j) and (k) with each other,
o) converting said severity value as combined at step (m) to a first monetary value,
p) converting said severity value as combined at step (n) to a second monetary value, and
q) combining said first and second monetary values.

63. The method as in claim 62, wherein step (q) includes expressing said combined first and second monetary values as a range of expected monetary values.

64. The method as in claim 29, including the step
e) where said person has lost, and/or will lose in the future, wages due to said medical conditions identified at step (c), assessing a monetary amount for said lost wages.

65. The method as in claim 29, including the step
f) where said person is predicted to lose wages due to said medical conditions identified at step (c), assessing a monetary amount for said lost wages.

66. A method for assessing an impact of medical conditions and impairments affecting a person, said method comprising the steps of
a) inputting into a computer a model of a human body, said model including body parts that, in combination with each other, form the human body, wherein said human body parts are classified into a multi-level hierarchy, each said body part in each level of said hierarchy below a highest level of said hierarchy being a component body part of a composite body part in a higher level in said hierarchy;
b) inputting into a computer, for each transient medical condition of a plurality of predetermined transient medical conditions, a severity value that estimates a time progression of a dysfunction level produced by said transient medical condition on at least one said body part;

c) identifying one or more said predetermined transient medical conditions that currently affect said person;

d) for each said body part having multiple said transient medical conditions identified at step (c), combining said severity values corresponding to said identified transient medical conditions to a total severity value for said body part based on a time at which said transient medical conditions to which said severity values correspond occurred;

e) for each said composite body part up to a composite body part corresponding to the human body as a whole, combining said severity value of each said component body part of said composite body part up to a composite body part severity value for said composite body part based on a spatial relationship among said component body parts within the human body;

f) where said person has spent time in a hospital as a patient, providing a severity value that describes an impact on said person from a time of injury over a specific progressive time scale into the future;

g) where said person has received convalescent care, providing a severity value that describes an impact on said person of time spent by said person under convalescent care;

h) where said person is predicted to suffer a transient medical condition in the future, providing a severity value, arranged in a progressive time line into the future, that describes an impact on said person of said transient medical condition;

i) where said person has suffered post traumatic stress syndrome, providing a severity value that describes an impact on said person of said post traumatic stress syndrome;

j) where said person has suffered a temporary loss of ability to enjoy life, providing at least one severity value that describes an impact on said person of said loss;

k) where said person has suffered a permanent loss of ability to enjoy life, providing at least one severity value that describes an impact on said person of said loss;

l) where said person has suffered a permanent dysfunction, providing a severity value that describes an impact on said person of said permanent dysfunction; and m) generating and outputting an assessment of the impact of said medical conditions on said person, wherein said assessment is based on said whole body severity value determined at step (e) and on any said severity values provided at steps (f)-(l).

67. The method as in claim 66, wherein said severity values are non-monetary values, including the step m) converting said whole body severity of step (e) and any said severities provided at steps (f)-(l) to a monetary value, and wherein said assessment is based on said monetary value.

68. The method as in claim 67, wherein step (m) includes the steps n) combining any said severity values provided at steps (f)-(j) with said whole body severity value of step (e), o) combining any said severity values provided at steps (k) and (l) with each other, p) converting said severity value as combined at step (n) to a first monetary value, q) converting said severity value as combined at step (m) to a second monetary value, and r) combining said first and second monetary values.

69. The method as in claim 68, wherein step (r) includes expressing said combined first and second monetary values as a range of expected monetary values.

70. The method as in claim 66, including the step m) where said person has lost, and/or will lose in the future, wages due to said medical conditions identified at step (c), assessing a monetary amount for said lost wages.

71. The method as in claim 66, including the step m) where said person is predicted to lose wages due to said medical conditions identified at step (c), assessing a monetary amount for said lost wages, and wherein said assessment is based on any said monetary amount provided at step m).

72. The method as in claim 66, wherein, for a said medical condition corresponding to a whiplash injury, step (b) includes deriving said severity value for said injury based on treatment applied to said whiplash injury.

73. A method for modeling medical conditions and impairments affecting a person, said method comprising the steps of:

a) where said person is subject to a workers' compensation system, i) providing a plurality of profiles relating predetermined transient medical conditions to human body parts, each said profile estimating a time progression of a dysfunction level or a capacity of at least one said body part from a time of injury over a specific progressive time scale into the future, due to at least one said condition;

ii) identifying one or more said predetermined transient medical conditions that currently affect said person, iii) selecting a said profile corresponding to each said transient medical condition, and iv) relating said selected profile's time dimension to an occurrence of its said transient medical condition;

b) where said person is subject to a common law compensation system, i) providing a model of a human body, said model including body parts that, in combination with each other, form the human body, ii) providing, for each transient medical condition of a plurality of predetermined transient medical conditions, a severity value that estimates the dysfunction level produced by said transient medical condition on at least one said body part, iii) identifying one or more said predetermined transient medical conditions that affect said person, and iv) combining said severity values for said transient medical conditions identified at step (b,iii) to a combined severity value; and c) displaying an assessment of an impact of said transient medical condition identified at steps (a,ii) or (b,iii) on said person, wherein said assessment is based on said profiles related to said transient medical conditions at step (d) or on said combined severity value at step (b,iv), respectively.

74. A method for assessing an impact of medical conditions and impairments affecting a person, said method comprising the steps of:

a) where said person is subject to a workers' compensation system, i) providing a plurality of profiles relating predetermined transient medical conditions to human body parts, each said profile estimating a time progression of a dysfunction level or a capacity of at least one said body part from a time of injury over a specific progressive time scale into the future, due to at least one said condition;

ii) identifying one or more said body parts that affect performance of a job by said person, iii) determining what capacity level of each said one or more body parts inhibits said person from performing said job, iv) identifying one or more said predetermined transient medical conditions that currently affect said person, v) selecting a said profile corresponding to each said one or more transient medical conditions, vi) relating each said selected profile's time dimension to an occurrence of its said transient medical condition, vii) for each said selected profile applicable to a said body part determined at step (a,ii), determining a date for said applicable selected profile upon which said estimated capacity profiled by said applicable selected profile first moves beyond said capacity level determined at step (a,iii) for its said body part so that said transient medical condition to which said applicable selected profile corresponds does not inhibit said job, and viii) determining a latest said date determined at step (a,vii);

b) where said person is subject to a common law compensation system, i) providing a model of a human body, said model including body parts that, in combination with each other, form the human body, wherein said human body parts are classified into a multi-level hierarchy, each said body part in each level of said hierarchy below a highest level of said hierarchy being a component body part of a composite body part in a higher level in said hierarchy, ii) providing, for each transient medical condition of a plurality of predetermined transient medical conditions, a severity value that estimates a dysfunction level produced by said transient medical condition on at least one said body part, iii) identifying one or more said predetermined transient medical conditions that currently affect said person, iv) for each said body part having multiple said transient medical conditions identified at step (b,iii), combining said severity values corresponding to said identified transient medical conditions to a total severity value for said body part based on a time at which said transient medical conditions to which said severity values correspond occurred, v) for each said composite body part up to a composite body part corresponding to the human body as a whole, combining said severity value of each said component body part of said composite body part up to a composite body part severity value for said composite body part based on a spatial relationship among said component body parts within the human body, vi) where said person has spent time in a hospital as a patient, providing a severity value that describes an impact on said person from a time of injury in a progressive time line into the future, vii) where said person has received convalescent care, providing a severity value that describes an impact on said person of time spent by said person under convalescent care, viii) where said person is predicted to suffer a transient medical condition in the future, providing a severity value that describes an impact on said person of said transient medical condition, ix) where said person has suffered post traumatic stress syndrome, providing a severity value that describes an impact on said person of said post traumatic stress syndrome, x) where said person has suffered a temporary loss of ability to enjoy life, providing at least one severity value that describes an impact on said person of said loss, xi) where said person has suffered a permanent loss of ability to enjoy life, providing at least one severity value that describes an impact on said person of said loss, and xii) where said person has suffered a permanent dysfunction, providing a severity value that describes an impact on said person of said permanent dysfunction; and c) displaying an assessment of an impact of said transient medical conditions identified at steps (a,ii) or (b,iii) on said person, wherein said assessment is based on said latest date at step (a,viii) or on said whole body severity at step (b,v) and any said severities provided at steps (b,vi)-(b,xii), respectively.

75. The method as in claim 74, wherein said severity values are non-monetary values, and including the step b,xiii) converting said whole body severity of step (b,v) and any said severities provided at steps (b,vi)-(b,xii) to a monetary value, and wherein said assessment is based on said monetary value.

76. The method as in claim 75, wherein said estimated capacity is described as a dysfunction level and wherein step (a,vii) includes determining said date from said applicable selected profile upon which said dysfunction level profiled by said applicable selected profile falls below said dysfunction level determined at step (a,iii) for its said body part.

77. The method as in claim 76, wherein, where said estimated capacity of said applicable selected profile fails to move beyond said, capacity level determined at step (a,iii) for its said body part so that said medical condition to which said applicable selected profile corresponds does not inhibit said job, said date determined at step (a,vii) indicates that said condition always inhibits said job.

78. The method as in claim 75, including, following step (a,vi) and prior to step (a,vii), the step (a,ix) for each said body part determined at step (a,ii) having multiple said selected profiles, combining said multiple profiles so that said body part has one profile that describes an estimated capacity of said body part over time, and wherein said combined profile from step (a,ix) is said applicable selected profile at step (a,vii) for said body part to which said combined profile applies.

79. The method as in claim 78, wherein said human body parts are classified into a multi-level hierarchy, each said body part in each level of said hierarchy below a highest level of said hierarchy being a component body part of a composite body part in a higher level in said hierarchy.

80. The method as in claim 79, including, following step (a,vi) and prior to step (a,vii), the steps a,ix) for at least one said composite body part having a said selected profile, allocating said estimated capacity of said selected profile among said component body parts of said composite body part, and a,x) creating an inherited profile for each said component body part of said composite body part of step (a,ix), said inherited profile describing said estimated capacity allocated to said component body part from said composite body part over time.

81. The method as in claim 80, including, following step (a,x) and prior to step (a,vii), the step a,xi) for each said body part that is a said body part determined at step (a,ii) or a lower-level component body part of a said body part determined at step (a,ii) and that has multiple said selected profiles and/or said inherited profiles, combining said multiple profiles so that said body part has one profile that describes an estimated capacity of said body part over time, and wherein said combined profile from step (a,xi) is said applicable selected profile at step (a,vii) for said body part to which said combined profile applies.

82. The method as in claim 81, including, following step (a,xi) and prior to step (a,vii) the step a,xii) combining, up to each composite body part that is a said body part determined at step (a,ii) or a lower-level component body part of a said body part determined at step (a,ii), said profile of each said component body part of said composite body part so that said composite body part has at most one profile that describes an estimated capacity of said composite body part over time, and wherein said combined profile from step (a,xii) is said applicable selected profile at step (a,vii) for said composite body part to which said combined profile applies.

83. A method for assessing insurance compensation stemming from medical conditions affecting a medically impaired person, said method comprising:

a) connecting to one or more databases comprising:

i) a multiple-level hierarchical model of the human body, including a plurality of body parts that make up the human body, wherein each body part is associated as a component of one or more other body parts and wherein each body part has associated component functionality values that indicate the body parts' importance to each of the one or more other body parts of which the body part is a component; and ii) a plurality of medical condition profiles each medical condition profile associating a transient medical condition, one or more body parts affected by the transient medical condition and one or more temporally variable dysfunction values indicating the relative affect of the transient medical condition on each of the one or more body parts over a range of times into the future;

b) receiving information indicating one or more patient transient medical conditions affecting the medically impaired person;

c) searching the one or more databases to identify medical condition profiles that associate transient medical conditions matching each of the one or more patient transient medical conditions received in step (b);

d) for each medical condition profile identified in step (c):

i) identifying the one or more body parts associated with the medical condition profile;

ii) identifying the temporally variable dysfunction value associated with each of the one or more body parts associated with the medical condition profile; and iii) using the model of (a, i) identify any body parts for which the one or more body parts of identified in (d, i) are a component;

e) generating a first capacity level for each of the one or more body parts of identified in (d, i) based on the associated temporally variable dysfunction value identified in (d, ii);

f) generating a second capacity level for any of the body parts identified in (d, iii) based on the capacity levels generated in (e) and the associated component functionality values; and g) generating and outputting an insurance compensation value based on the results of steps (e) and/or (f).

* * * * *